US006844366B2

(12) United States Patent
Billledeau et al.

(10) Patent No.: US 6,844,366 B2
(45) Date of Patent: Jan. 18, 2005

(54) SULFONAMIDE HYDROXAMATES

(75) Inventors: Roland Joseph Billledeau, Santa Clara, CA (US); Chris Allen Broka, Foster City, CA (US); Jeffrey Allen Campbell, Fremont, CA (US); Jian Jeffrey Chen, Santa Clara, CA (US); Sharon Marie Dankwardt, Foster City, CA (US); Nancy Delaet, San Diego, CA (US); Leslie Ann Robinson, Los Altos, CA (US); Keith Adrian Murray Walker, Los Altos, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/267,292

(22) Filed: Oct. 9, 2002

(65) Prior Publication Data

US 2003/0199520 A1 Oct. 23, 2003

Related U.S. Application Data

(62) Division of application No. 09/469,660, filed on Dec. 22, 1999, now Pat. No. 6,492,394.
(60) Provisional application No. 60/113,311, filed on Dec. 22, 1998, provisional application No. 60/147,053, filed on Aug. 3, 1999, and provisional application No. 60/164,138, filed on Nov. 8, 1999.

(51) Int. Cl.$^7$ .................. A61K 31/165; C07C 259/04
(52) U.S. Cl. ............... 514/575; 514/222.2; 514/237.8; 514/255; 514/331; 514/357; 514/438; 544/59; 544/106; 544/398; 546/229; 546/266; 549/74; 549/623
(58) Field of Search .................. 514/222.2, 237.8, 514/255, 331, 357, 438, 575, 227.5, 227.8, 228.5, 331.2, 233.8, 234.5, 235.2, 235.5, 311, 314, 318, 321, 322, 323, 326, 337, 338, 339, 394, 412, 419, 432, 443, 464, 228.2, 231.2; 544/59, 106, 398, 58.4, 124, 128, 139, 143, 153, 159, 363, 370, 373, 377, 386; 546/229, 266; 549/74; 562/623

(56) References Cited

U.S. PATENT DOCUMENTS

| 5,455,258 A | 10/1995 | MacPherson et al. ....... 514/357 |
| 5,506,242 A | 4/1996 | MacPherson et al. ....... 514/336 |
| 5,552,419 A | 9/1996 | MacPherson et al. ....... 514/357 |
| 5,646,167 A | * 7/1997 | MacPherson et al. ....... 514/357 |
| 5,753,653 A | 5/1998 | Bender et al. ............. 514/357 |
| 5,770,624 A | 6/1998 | Parker ........................ 514/575 |

FOREIGN PATENT DOCUMENTS

| EP | 0 606 046 A1 | 7/1994 |
| EP | 0 915 086 | 12/1997 |
| JP | 10204054 A | 8/1998 |
| WO | WO 97/05865 | 2/1997 |
| WO | WO 98/43963 | 10/1998 |
| WO | WO 98/50348 | 11/1998 |

OTHER PUBLICATIONS

McCullough "Bleomycin–induced diffuse interstitial pulmonary fibrosis in baboons" CA 88:146753 (1978).*
Raghow et al. "Profiles of steady state . . . " CA 104:15995 (1986).*
Watanabe et al. "Type Ili procollage . . . " CA 104:32553 (1986).*
Kato et al. "Bleomycin–induced arthritis . . . " CA 128:162624 (1998).*
Parizada et al. "Protective effects of . . . " CA 116:192043 (1992).*
Gonnella et al. "Bioactive conformation . . . " CA 122:177675 (1995).*
Gonnella et al. "Bioactive conformation of . . . " CA 124:224712 (1996).*
MacPherson et al. "Preparation of heteroaryl–sulfonamido . . . " CA 124:289286 (1996).*
Watanabe et al. "Preparation of N–sulfonylaminl . . . " CA 127:162119 (1997).*
Clare et al. "Protease inhibitors . . . " CA 135:133815 (2001).*
MacPherson, et al., *Journal of Medicinal Chemistry*, vol. 40:16 (1997) pp 2525–2532, "Discovery of CGS 27023A, a Non–Peptidic, Potent, and Orally Active Stromelysin Inhibitor That Blocks Cartilage Degradation in Rabbits".
Jeng, et al., *Bioorganic and Medicinal Chemistry Letter*, vol. 8:8 (1998) pp 897–902, "Sulphonamide–based hydroxamic acids as potent inhibitors of mouse macrophase metalloelastase".
Fish r, t al., *B richt d r Deutsch n Chemisch n G s llschaft*, vol. 49 (1916) pp 1355–1366, "Bildung aktiver, sekunärer Aminosaurenaus Halogenaäuren und primären Aminen".
Chemical Abstract No. No. 6563F (XP–002135506), vol. 54:7 (Apr. 10, 1960) for Budeskinsky, et al., Ceskoslov, Farm., vol. 8 (1959) pp 161–166 "Synthetic antidiabetics. II. N–Tosylated amino acids and their N–alkyl derivatives".
Gellert, et al., *Australian Journal of Chemistry*, vol. 37:4 (1984) pp 819–829, "Stereospecific synthesis of hexahydrobenzopyrroloisoquinoline and tetrahydrobenzisoquinoline derivatives".
Gonzales–Cameno, et al., *Tetrahedron*, vol. 50:37 (1994) pp 10971–10982, "Preparation of a 3–Phenyl–4(3H)–isoquinolinone and its transformation in 12(11H)–Benzo[c] phenanthridinone Derivatives. Crystal structure determinations".
Jurczak, et al., *Tetrahedron*, vol. 54:22 (1998) pp 6051–6064, "Effective and Mild Method for Preparation of Optically Active α–Amino Aldehydes via TEMPO Oxidation".
Dankwardt, et al., *Synlett*, No. 7 (Jul. 1997) pp 854–856, Solid phase synthesis of N–alkyl sulphonamides.

* cited by examiner

*Primary Examiner*—Celia Chang
(74) *Attorney, Agent, or Firm*—Robert C. Hall

(57) ABSTRACT

This invention relates to certain sulfonamide derivatives that are inhibitors of procollagen C–proteinase, pharmaceutical compositions containing them, methods for their use and methods for preparing these compounds.

11 Claims, No Drawings

SULFONAMIDE HYDROXAMATES

CROSS-REFERENCE TO RELATED APPLICATION

This application is a divisional of U.S. application Ser. No. 09/469,660 filed date Dec. 22, 1999 now U.S. Pat. No. 6,492,394.

This application claims the benefit under 35 U.S.C. 119(e) of U.S. Provisional Application Ser. No. 60/113,311, filed Dec. 22, 1998; U.S. Provisional Application Ser. No. 60/147,053, filed Aug. 3, 1999; and U.S. Provisional Application Ser. No. 60/164,138, filed Nov. 8, 1999. All of the foregoing are hereby incorporated by reference in their entirety.

BACKGROUND OF THE INVENTION

1. Field of the Invention

The present invention relates to certain sufonamide derivatives that inhibit procollagen C-proteinase, pharmaceutical compositions containing them, methods for their use, and methods for preparing these compounds.

2. Background Information and Related Disclosures

The collagens are integral components of connective tissue. At present nineteen types of collagens have been identified. The interstitial collagen types I, II, and III are the major collagen components of tissue. These collagens are synthesized as procollagen precursor molecules having amino- and carboxy-terminal peptide extensions also known as pro-regions. These pro-regions are typically cleaved upon secretion of the procollagen molecule to give a mature collagen molecule which is capable of association into highly structured collagen fibers, ((see, e.g., Fessler and Fessler, *Annu. Rev. Biochem.* 47, 129, (1978); Kivirikko et al., *Extracellular Matrix Biochemistry* (1984) and Kuhn, *Structure and Function of Collagen Types* (eds. Mayne, R and Burgeson, R. E.), Academic Press, Inc., Orlando, Fla., pp. 1–42 (1987)). It is well established that excessive collagen deposition is associated with a variety of fibrotic diseases such as interstitial pulmonary fibrosis, pericentral fibrosis, Symmers' fibrosis, perimuscular fibrosis, kidney fibrosis, endocardial sclerosis, hepatitis, acute respiratory distress syndrome, arthritis, cystic fibrosis, tendon surgery, corneal scarring, surgical adhesions, scleroderma, chronic allograft rejection, hemodialysis shunt fibrosis, liver fibrosis and restenosis. These diseases are chatacterized by excessive deposits of fibrillar interstitial collagens that are resistant to proteolytic degradation thus leading to the symptoms of fibrosis. Therefore, inhibition of the pathological deposition of these collagens should help in the treatment of these diseases.

Recent studies suggest that C-proteinase is the essential enzyme that catalyzes the cleavage of the C-propeptide of types I, II, and III collagens and is therefore instrumental in the formation of functional collagen fibers ((see, Fertala et al., *J. Biol. Chem.*, 269, 11584, (1994)). It would therefore be desirable to provide procollagen C-proteinase inhibitors and thereby provide a means of combating diseases mediated by excessive deposition of these collagens. The compounds of this invention fulfill this and related needs.

SUMMARY OF THE INVENTION

In a first aspect, this invention provides sulfonamide derivatives selected from the group of compounds represented by Formula (I):

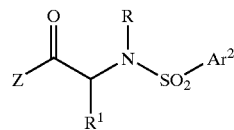

(I)

wherein:

Z is —OH, —NHOH, or $OR^{12}$ wherein $R^{12}$ is alkyl;

$R^1$ is alkyl, haloalkyl, heteroalkyl, cycloalkyl, aryl, aralkyl, aralkenyl, heteroaryl, heteroaralkyl, heteroaralkenyl, heterocyclylalkyl, cycloalkylalkyl, -(alkylene)-C(O)—X where X is alkyl, haloalkyl, cycloalkyl, cycloalkylalkyl, amino, monosubstituted amino, disubstituted amino, aryl, aralkyl, heteroaryl, heteroaralkyl, heterocyclyl, heterocyclylalkyl, hydroxy, alkoxy, cycloalkoxy, cycloalkylalkoxy, heteroalkyloxy, aralkyloxy, or heteroaralkyloxy), or —C(=NR')NHSO$_2$R" (where R' is hydrogen or alkyl, and R" is alkyl, haloalkyl, cycloalkyl, cycloalkylalkyl, aryl, aralkyl, heteroaryl, heteroaralkyl, or heterocyclylalkyl);

R is —CH($R^2$)Ar$^1$ or —CH($R^2$)CH=CHAr$^1$ where $R^2$ is hydrogen or alkyl; and Ar$^1$ is aryl or heteroaryl;

Ar$^2$ is either:

(i) a phenyl ring of formula (a):

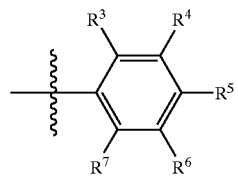

(a)

wherein:

$R^3$ and $R^7$ are, independently of each other, hydrogen, alkyl, alkylthio, or halo;

$R^4$ and $R^6$ are, independently of each other, hydrogen, alkyl, or halo;

$R^5$ is alkyl, haloalkyl, heterocyclyl, alkylthio, arylthio, aralkylthio, heteroarylthio, heteroaralkylthio, cycloalkylthio, cycloalkylalkylthio, alkoxy, aryloxy, aralkoxy, heteroaryloxy, heteroaralkyloxy, cycloalkoxy, cycloalkylalkoxy, alkyloxycarbonyl, hydroxy, halo, cyano, carboxy, nitro, amino, monoalkylamino, dialkylamino, alkylsulfonyl, arylsulfonyl, aralkylsulfonyl, heteroarylsulfonyl, heteroaralkylsulfonyl, cycloalkylsulfonyl, cycloalkylalkylsulfonyl, or —Y-(alkylene)-C(O)—Z [where Y is a bond, —NR$^a$—, —O—, or —S(O)$_n$— (where n is 0 to 2), R$^a$ is hydrogen or alkyl, and Z is alkoxy, hydroxy, amino, monosubstituted amino, or disubstituted amino]; or $R^5$ together with $R^4$ forms —O—(CR$^8$R$^9$)$_n$— where n is 2 or 3 and each $R^8$ and $R^9$ are, independently of each other, hydrogen or alkyl; or the carbon atoms to which $R^5$ and $R^4$ are attached are fused to the C2–C3 carbons of a benzofuran ring;

provided that at least two of $R^3$, $R^4$, $R^6$, and $R^7$ are not hydrogen at the same time; or (ii) a naphthyl ring of formula (b):

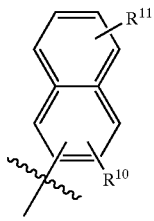

wherein:

R$^{10}$ is hydrogen, alkyl, alkoxy, or halo; and

R$^{11}$ is hydrogen, alkyl, haloalkyl, alkylthio, alkoxy, alkyloxycarbonyl, aryloxy, hydroxy, halo, cyano, carboxy, nitro, amino, monoalkylamino, dialkylamino or alkylsulfonyl provided that both R$^{10}$ and R$^{11}$ are not hydrogen at the same time; and their pharmaceutically acceptable salts, prodrugs, individual isomers, and mixtures of isomers.

Within the group of compounds represented by Formula (I), sulfonamide derivatives of this invention wherein Z is NHOH are represented by Formula (Ia):

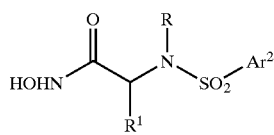

In a second aspect, this invention provides a method of treatment of a disease treatable by administration of a therapeutically effective amount of a procollagen C-proteinase inhibitor of Formula (Ib) wherein:

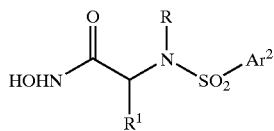

wherein:

R$^1$ is alkyl, haloalkyl, heteroalkyl, cycloalkyl, aryl, aralkyl, aralkenyl, heteroaryl, heteroaralkyl, heteroaralkenyl, heterocyclylalkyl, cycloalkylalkyl, -(alkylene)-C(O)—X (where X is alkyl, haloalkyl, cycloalkyl, cycloalkylalkyl, amino, monosubstituted amino, disubstituted amino, aryl, aralkyl, heteroaryl, heteroaralkyl, heterocyclyl, heterocyclylalkyl, hydroxy, alkoxy, cycloalkoxy, cycloalkylalkoxy, heteroalkyloxy, aralkyloxy, or heteroaralkyloxy), or —C(=NR')NHSO$_2$R" (where R' is hydrogen or alkyl, and R" is alkyl, haloalkyl, cycloalkyl, cycloalkylalkyl, aryl, aralkyl, heteroaryl, heteroaralkyl, or heterocyclylalkyl);

R is —CH(R$^2$)Ar$^1$ or —CH(R$^2$)CH=CHAr$^1$ where R$^2$ is hydrogen or alkyl; and Ar$^1$ is aryl or heteroaryl;

Ar$^2$ is either:

(i) a phenyl ring of formula (a):

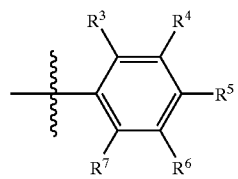

wherein:

R$^3$ and R$^7$ are, independently of each other, hydrogen, alkyl, alkylthio, or halo;

R$^4$ and R$^6$ are, independently of each other, hydrogen, alkyl, or halo;

R$^5$ is alkyl, haloalkyl, heterocyclyl, alkylthio, arylthio, aralkylthio, heteroarylthio, heteroaralkylthio, cycloalkylthio, cycloalkylalkylthio, alkoxy, aryloxy, aralkoxy, heteroaryloxy, heteroaralkyloxy, cycloalkoxy, cycloalkylalkoxy, alkyloxycarbonyl, hydroxy, halo, cyano, carboxy, nitro, amino, monoalkylamino, dialkylamino, alkylsulfonyl, arylsulfonyl, aralkylsulfonyl, heteroarylsulfonyl, heteroaralkylsulfonyl, cycloalkylsulfonyl, cycloalkylalkylsulfonyl, or —Y-(alkylene)-C(O)—Z [where Y is a bond, —NR$^a$—, —O—, or —S(O)$_n$— (where n is 0 to 2), R$^a$ is hydrogen or alkyl, and Z is alkoxy, hydroxy, amino, monosubstituted amino, or disubstituted amino]; or R$^5$ together with R$^4$ forms —O—(CR$^8$R$^9$)$_n$— where n is 2 or 3 and each R$^8$ and R$^9$ are, independently of each other, hydrogen or alkyl; or the carbon atoms to which R$^5$ and R$^4$ are attached are fused to the C2–C3 carbons of a benzofuran ring; or (ii) a naphthyl ring of formula (b):

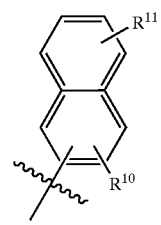

wherein:

R$^{10}$ is hydrogen, alkyl, alkoxy, or halo; and

R$^{11}$ is hydrogen, alkyl, haloalkyl, alkylthio, alkoxy, alkyloxycarbonyl, aryloxy, hydroxy, halo, cyano, carboxy, nitro, amino, monoalkylamino, dialkylamino or alkylsulfonyl; and their pharmaceutically acceptable salts, prodrugs, individual isomers, and mixtures of isomers.

In a third aspect, this invention provides pharmaceutical compositions containing a therapeutically effective amount of a compound of Formula (Ia) or (Ib) or its pharmaceutically acceptable salt and a pharmaceutically acceptable excipient.

In a fourth aspect, this invention provides a process for preparing compounds of Formula (Ia) or (Ib).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Halo" means fluoro, chloro, bromo, or iodo, preferably fluoro and chloro.

"Haloalkyl" means alkyl substituted with one or more same or different halo atoms, e.g., $-CH_2Cl$, $-CF_3$, $-CH_2CF_3$, $-CH_2CCl_3$, and the like.

"Cycloalkyl" means a saturated monovalent cyclic hydrocarbon radical of three to seven ring carbons. The cycloalkyl may be optionally substituted independently with one, two, or three substituents selected from alkyl, haloalkyl, halo, nitro, cyano, optionally substituted phenyl, optionally substituted heteroaralkyl, $-OR$ (where R is hydrogen, alkyl, or haloalkyl, $-NRR'$ (where R and R' are independently hydrogen or alkyl), or $-C(O)R$ (where R is hydrogen, alkyl, or optionally substituted phenyl). More specifically, the term cycloalkyl includes, for example, cyclopropyl, cyclohexyl, 1,2-dihydroxycyclopropyl, and the like.

"Monosubstituted amino" means a radical $-NHR$ where R is alkyl, haloalkyl, cycloalkyl, cycloalkylalkyl, hydroxyalkyl, aryl, aralkyl, aralkenyl, heteroaryl, heteroaralkyl, heteroaralkenyl, heterocyclyl, or heterocyclylalkyl, e.g., methylamino, ethylamino, phenylamine, benzylamine, dibenzylamine, and the like.

"Disubstituted amino" means a radical $-NRR'$ where R and R' are, independently of each other, is alkyl, haloalkyl, cyanoalkyl, cycloalkyl, cycloalkylalkyl, hydroxyalkyl, aryl, aralkyl, aralkenyl, heteroaryl, heteroaralkyl, heteroaralkenyl, heterocyclyl, or heterocyclylalkyl, or R and R' together with the nitrogen atom to which they are attached form a heterocyclyl ring. Representative examples include, but are not limited to, dimethylamino, methylethylamino, di(1-methyl-ethyl)amino, piperazinyl, and the like.

"Monoalkylamino" means a radical $-NHR$ where R is alkyl, e.g., methylamino, ethylamino, and the like.

"Dialkylamino" means a radical $-NRR'$ where R and R' are independently of each other alkyl. Representative examples include, but are not limited to, dimethylamino, methylethylamino, di(1-methylethyl)amino, and the like.

"Aryl" means a monovalent monocyclic or bicyclic aromatic hydrocarbon radical of 6 to 10 ring atoms which is substituted independently with one or more substituents, preferably one, two, or three substituents selected from alkyl, haloalkyl, thioalkyl, heteroalkyl, halo, nitro, cyano, optionally substituted phenyl, heteroaryl, heterocyclyl, hydroxy, alkoxy, haloalkoxy, optionally substituted phenyloxy, heteroaryloxy, methylenedioxy, ethylenedioxy, $-COR$ (where R is alkyl or optionally substituted phenyl), $-(alkylene)_n-COOR$ (where n is 0 or 1 and R is hydrogen, alkyl, optionally substituted phenylalkyl, or heteroaralkyl), $-NR^aR^b$ (where $R^a$ and $R^b$ are independently of each other, hydrogen, alkyl, cycloalkyl, cycloalkylalkyl, hydroxyalkyl, optionally substituted phenyl, or heteroaryl), $-NR^aCOR^b$ (where $R^a$ is hydrogen or alkyl and $R^b$ is hydrogen, alkyl, haloalkyl, or optionally substituted phenyl), $-S(O)_nR$ [where n is an integer from 0 to 2 and R is hydrogen (provided that n is 0), alkyl, cycloalkyl, cycloalkylalkyl, heteroalkyl, optionally substituted phenyl, optionally substituted phenylalkyl, or heteroaryl], $-SO_2NR^aR^b$ (where $R^a$ and $R^b$ are, independently of each other hydrogen, alkyl, hydroxyalkyl, or optionally substituted phenyl, or $R^a$ and $R^b$ together with the nitrogen atom to which they are attached form a heterocyclyl ring), $-NRSO_2R'$ (where R is hydrogen or alkyl and R' is alkyl, cycloalkyl, cycloalkylalkyl, heteroalkyl, optionally substituted phenyl, optionally substituted phenylalkyl, or heteroaryl), $-NRSO_2NR'R''$ (where R is hydrogen or alkyl and R' and R'' are, independently of each other, hydrogen, alkyl, or hydroxyalkyl, or R' and R'' together with the nitrogen atom to which they are attached form a heterocyclyl ring), or $-(alkylene)_n-CONR^aR^b$ (where n is 0 or 1, and $R^a$ and $R^b$ are, independently of each other, hydrogen or alkyl, or $R^a$ and $R^b$ together with the nitrogen atom to which they are attached form a heterocyclyl ring). More specifically the term aryl includes, but is not limited to, phenyl, 1-naphthyl, and 2-naphthyl, and the derivatives thereof.

"Optionally substituted phenyl" means a phenyl ring which is optionally substituted independently with one or more substituents, preferably one or two substituents selected from alkyl, haloalkyl, thioalkyl, hydroxyalkyl, halo, nitro, cyano, hydroxy, alkoxy, carboxy, alkoxycarbonyl, amino, methylenedioxy, ethylenedioxy, $-COR$ (where R is alkyl), $-COOR$ (where R is alkyl), $-NR^aR^b$ (where $R^a$ and $R^b$ are independently of each other hydrogen or alkyl), $-NR^aCOR^b$ (where $R^a$ is hydrogen or alkyl and $R^b$ is alkyl, haloalkyl, or optionally substituted phenyl), or $-CONR^aR^b$ (where $R^a$ and $R^b$ are independently of each other hydrogen or alkyl). More specifically the term aryl includes, but is not limited to, phenyl, 1-napthyl, and 2-naphthyl, and the derivatives thereof.

"Heteroaryl" means a monovalent monocyclic or bicyclic aromatic radical of 5 to 12 ring atoms containing one, two, or three ring heteroatoms selected from N, O, or S, the remaining ring atoms being C. The heteroaryl ring is optionally substituted independently with one or more substituents, preferably one or two substituents, selected from alkyl, haloalkyl, heteroalkyl, heterocyclyl, halo, nitro, cyano, $-OR$ (where R is hydrogen, alkyl, haloalkyl, optionally substituted phenyl, or optionally substituted heteroaryl), $-NRR'$ (where R and R' are, independently of each other, hydrogen, alkyl, cycloalkyl, cycloalkylalkyl, hydroxyalkyl, or optionally substituted phenyl), $-C(O)R$ (where R is hydrogen, alkyl, or optionally substituted phenyl), $-(alkylene)_n-COOR$ (where n is 0 or 1 and R is hydrogen, alkyl, optionally substituted phenylalkyl, or optionally substituted heteroaralkyl), $-S(O)_nR$ [where n is an integer from 0 to 2 and R is hydrogen (provided that n is 0), alkyl, cycloalkyl, cycloalkylalkyl, heteroalkyl, optionally substituted phenyl, optionally substituted phenylalkyl, or optionally substituted heteroaryl], $-SO_2NR'R''$ (where R' and R'' are, independently of each other, hydrogen, alkyl, hydroxyalkyl, or optionally substituted phenyl, or R' and R'' together with the nitrogen atom to which they are attached form a heterocyclyl ring), $-NRC(O)R'$ (where R is hydrogen or alkyl and R' is alkyl, haloalkyl, or optionally substituted phenyl), $-NRSO_2R'$ (where R is hydrogen or alkyl and R' is alkyl, cycloalkyl, cycloalkylalkyl, heteroalkyl, optionally substituted phenyl, optionally substituted phenylalkyl, or optionally substituted heteroaryl), —NRSO$_2$NR'R" (where R is hydrogen or alkyl, and R' and R" are, independently of each other, hydrogen or alkyl, or R' and R" together with the nitrogen atom to which they are attached form a heterocyclyl ring), -(alkylene)$_n$—CONR'R" (where n is 0 or 1 and R' and R" are, independently of each other, hydrogen or alkyl, or R' and R" together with the nitrogen atom to which they are attached form a heterocyclyl ring), or an amino protecting group. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the derivatives thereof.

"Heterocyclyl" means a saturated cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclo ring may be optionally substituted independently with one, two, or three substituents selected from alkyl, haloalkyl, halo, nitro, cyano, optionally substituted phenyl, optionally substituted heteroaryl, optionally substituted phenylalkyl, optionally substituted heteroaralkyl, —OR (where R is hydrogen, alkyl, or haloalkyl), —NRR' (where R and R' are independently hydrogen or alkyl), —C(O)R (where R is hydrogen, alkyl, heteroalkyl, aryl, heteroaryl, or aryloxyalkyl), —COOR (where R is hydrogen, alkyl, aryl, aralkyl, heteroaralkyl), -(alkylene)-COOR (where R is hydrogen, alkyl, optionally substituted phenyl, optionally substituted phenylalkyl, or optionally substituted heteroaralkyl), —CONR'R", or -(alkylene)-COONR'R" (where R' and R" are independently selected from hydrogen, alkyl, cycloalkyl, cycloalkylalkyl, heterocyclyl, aryl, aralkyl, heteroaryl), —S(O)$_n$R (where n is an integer from 0 to 2 and R is hydrogen (provided that n is 0) or alkyl), alkoxycarbonyl, —NRC(O)R' (where R is hydrogen or alkyl and R' is hydrogen or alkyl), —NRSO$_2$R' (where R is hydrogen or alkyl and R' is alkyl), —NRSO$_2$NR'R" (where R, R' and R" are independently hydrogen or alkyl), or an amino protecting group. The heterocyclo ring also may be optionally fused with an aryl ring as defined above. More specifically the term heterocyclo includes, but is not limited to, tetrahydropyranyl, piperidino, piperazino, morpholino and thiomorpholino, thiomorpholino-1-oxide, thiomorpholino-1,1-dioxide, and the derivatives thereof.

"Heteroalkyl" means an alkyl, cycloalkyl, or cycloalkylalkyl radical as defined above, carrying a substituent selected from —NR$^a$R$^b$, —OR$^c$, or —S(O)$_n$R$^d$ wherein n is an integer from 0 to 2, R$^a$ is hydrogen, alkyl, or —COR (where R is hydrogen, alkyl, or haloalkyl); R$^b$ is hydrogen, alkyl, haloalkyl, cycloalkyl, cycloalkylalkyl, aryl, aralkyl, heteroaryl, heteroaralkyl, heterocyclyl, heterocyclylalkyl, heterocyclyhydroxyalkyl, —COR (where R is hydrogen, alkyl, haloalkyl, monosubstituted aminoalkyl, aryloxyalkyl, cycloalkyl, cycloalkylalkyl, aryl, aralkyl, heteroaryl, heteroaralkyl, heterocyclylalkyl, or -(alkylene)-C(O)—X (where X is alkyl, haloalkyl, cycloalkyl, cycloalkylalkyl, amino, monosubstituted amino, disubstituted amino, aryl, aralkyl, heteroaryl, heteroaralkyl, heterocyclyl, or heterocyclyalkyl), —SO$_2$R (where R is alkyl, haloalkyl, cycloalkyl, cycloalkylalkyl, aryl, aralkyl, heteroaryl, heteroaralkyl, heterocyclyl, heterocyclylalkyl, amino, monosubstituted amino or disubstituted amino), —COOR (where R is hydrogen, alkyl, haloalkyl, cycloalkyl, cycloalkylalkyl, aryl, aralkyl, heteroaryl, heteroaralkyl, or heterocyclylalkyl), —CONR'R", or -(alkylene)-CONR'R" [where R' and R" are independently selected from hydrogen, alkyl, cycloalkyl, cycloalkylalkyl, heterocyclyl, aryl, aralkyl, heteroaryl, heteroaralkyl, or SO$_2$R (where R is alkyl, haloalkyl, cycloalkyl, cycloalkylalkyl, aryl, aralkyl, heteroaryl, heteroaralkyl, heterocyclyl, heterocyclylalkyl, amino, monosubstituted amino or disubstituted amino), or R' and R" together with the nitrogen atom to which they are attached form a heterocyclyl ring]; R$^c$ is hydrogen, alkyl, haloalkyl, cycloalkyl, cycloalkylalkyl, aryl, aralkyl, heteroaryl, heteroaralkyl, heterocyclylalkyl, —COR (where R is alkyl, haloalkyl, or heterocyclyl), or —CONR'R" (where R' and R" are independently selected from hydrogen, alkyl, cycloalkyl, cycloalkylalkyl, aryl, aralkyl, heteroaryl, or heteroaralkyl); and R$^d$ is hydrogen (provided that n is 0), alkyl, cycloalkyl, cycloalkylalkyl, aryl, aralkyl, heteroaryl, heteroaralkyl, heterocyclyl, heterocyclylalkyl, amino, monosubstituted amino, or disubstituted amino. Representative examples include, but are not limited to hydroxymethyl, 2-hydroxyethyl, 2-methoxyethyl, benzyloxymethyl, thiophen-2-ylthiomethyl, and the like;

"Aralkyl" means a radical —R$^a$R$^b$ where R$^a$ is an alkylene group and R$^b$ is an aryl group as defined above e.g., benzyl, phenylethyl, 3-(3-chlorophenyl)-2-methylpentyl, and the like.

"Aralkenyl" means a radical —R$^a$R$^b$ where R$^a$ is an alkenyl group and R$^b$ is an aryl group as defined above e.g., 3-phenyl-2-propenyl, and the like.

"Heteroaralkyl" means a radical —R$^a$R$^b$ where R$^a$ is an alkylene group and R$^b$ is a heteroaryl group as defined above e.g., pyridin-3-ylmethyl, 3-(benzofuran-2-yl)propyl, and the like.

"Heteroaralkenyl" means a radical —R$^a$R$^b$ where R$^a$ is an alkenyl group and R$^b$ is a heteroaryl group as defined above e.g., 3-pyridin-3-ylpropen-2-yl, and the like.

"Heterocyclylalkyl" means a radical —R$^a$R$^b$ where R$^a$ is an alkylene group and R$^b$ is a heterocyclyl group as defined above e.g., tetrahydropyran-2-ylmethyl, 4-methylpiperazin-1-ylethyl, 2-, or 3-piperidinylmethyl, and the like.

"Cycloalkylalkyl" means a radical —R$^a$R$^b$ where R$^a$ is an alkylene group and R$^b$ is a cycloalkyl group as defined above e.g., cyclopropylmethyl, cyclohexylpropyl, 3-cyclohexyl-2-methylpropyl, and the like.

"Alkoxy", "aryloxy", "aralkyloxy", or "heteroaralkyloxy" means a radical —OR where R is an alkyl, aryl, aralkyl, or heteroaralkyl respectively, as defined above e.g., methoxy, phenoxy, pyridin-2-ylmethyloxy, benzyloxy, and the like.

"Hydroxyalkyl" means an alkyl radical as defined above, carrying one or more, preferably one, two or three hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Optional" or "optionally" means that the subsequently described event or circumstance may but need not occur, and that the description includes instances where the event or circumstance occurs and instances in which it does not. For example, "heterocyclo group optionally mono- or disubstituted with an alkyl group" means that the alkyl may but need not be present, and the description includes situations where the heterocyclo group is mono- or disubstituted with an alkyl group and situations where the heterocyclo group is not substituted with the alkyl group.

"Amino protecting group" refers to those organic groups intended to protect nitrogen atoms against undesirable reactions during synthetic procedures e.g., benzyl, benzyloxycarbonyl (CBZ), tert-butoxycarbonyl (Boc), trifluoroacetyl, 2-trimethylsilyl-ethanesulfonyl (SES), and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, where a carbon atom is bonded to four different groups, a pair of enantiomers is possible. An enantiomer can be characterized by the absolute configuration of its asymmetric center and is described by the R- and S-sequence rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The naming and numbering of the compounds of this invention is illustrated below.

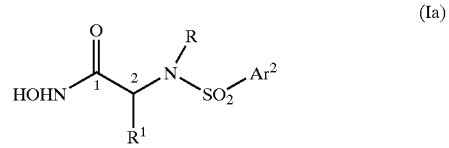

(Ia)

The nomenclature used in this application is generally based on the IUPAC recommendations, e.g., a compound of formula (Ia):

where $R^1$ is —CH(CH$_3$)$_2$, R is —CH(R$^2$)Ar$^1$ wherein $R^2$ is hydrogen, Ar$^1$ is 3,4-methylenedioxyphenyl, Ar$^2$ is 4-methoxyphenyl and the stereochemistry at the carbon to which $R^1$ is attached is (R) is named, N-hydroxy-2(R)-[(3, 4-methylenedioxybenzyl)-(4-methoxybenzenesulfonyl) amino]-3-methylbutyramide.

where $R^1$ is —CH$_2$OH, R is —CH(R$^2$)Ar$^1$ wherein $R^2$ is hydrogen, Ar$^1$ is indol-5-yl, Ar$^2$ is 2,3,6-trimethyl-4-methoxyphenyl and the stereochemistry at the carbon to which $R^1$ is attached is (R) is named, N-hydroxy-2(R)-[(1H-indol-5-ylmethyl)-(4-methoxy-2,3,6-trimethylbenzenesulfonyl)amino]-3-hydroxypropionamide.

Respresentative compounds of this invention are as follows:

I. Compounds of Formula (Ia) and (Ib) wherein R is —CH(R$^2$)Ar$^1$ and the other groups are defined as follows:

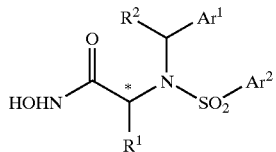

| CPD # | Stereo-chem at *C | R² | R¹ | Ar¹ | Ar² | M. Pt ° C. | Mass Spec. MH+ |
|---|---|---|---|---|---|---|---|
| 1 | (R) | H | 2-propyl | indol-5-yl | 4-methoxyphenyl | 105–107 | 439 |
| 2 | (R) | H | (CH₃)₂CHCH₂ | 3,4-methylenedioxyphenyl | 4-bromophenyl | 117.8–119.2 | 499 |
| 3 | (R) | H | 2-propyl | 3,4-methylenedioxyphenyl | 2-methoxy-6-naphthyl | 152–153 | 487 |
| 4 | (R) | H | CH₃CO₂CH₂ | 3,4-methylenedioxyphenyl | 2,3,6-trimethyl-4-methoxyphenyl | 78–81 | 547 |
| 5 | (R) | H | hydroxymethyl | 3,4-methylenedioxyphenyl | 2,3,6-trimethyl-4-methoxyphenyl | 167.3–168.1 | 467 |
| 6 | (R) | H | 2-propyl | 3,4-dihydroxyphenyl | 4-methoxyphenyl | 88.5–92 | 425 |
| 7 | (R) | H | 2-propyl | 3,4-methylenedioxyphenyl | 4-chlorophenyl | | 441 |
| 8 | (R) | H | 2-propyl | 3,4-methylenedioxyphenyl | 4-methoxyphenyl | 162.3–163.6 | 437 |
| 9 | (R) | H | 2-propyl | 3,4-methylenedioxyphenyl | 4-bromophenyl | | 485 |
| 10 | (R) | H | benzyl | 3,4-methylenedioxyphenyl | 4-methoxyphenyl | | 485 |
| 11 | (R) | H | 2-propyl | indol-5-yl | 2,3,6-trimethyl-4-methoxyphenyl | 103–106 | 474 |
| 12 | (R) | H | 2-propyl | 3,4-methylenedioxyphenyl | 2,3,6-trimethyl-4-methoxyphenyl | 129–131 | 479 |
| 13 | (R) | H | 2-propyl | 3,4-dihydroxyphenyl | 2,2,5,7,8-pentamethyl-chroman-6-yl | 144–146 | 521 |
| 14 | (R) | H | hydroxymethyl | 3,4-methylenedioxyphenyl | 2,5-dimethyl-4-chlorophenyl | | 457 |
| 15 | (R) | H | tert-butoxymethyl | indol-5-yl | 2,3,6-trimethyl-4-methoxyphenyl | | 517 |
| 16 | (R) | H | 2-propyl | 3,4-methylenedioxyphenyl | dibenzofuran-4-yl | 172.5–175 | 497 |
| 17 | (RS) | H | ethyl | 3,4-methylenedioxyphenyl | 4-bromophenyl | | 471 |
| 18 | (RS) | CH₃ | ethyl | 3,4-methylenedioxyphenyl | 4-bromophenyl | | 485 |
| 19 | (R) | H | 2-propyl | 3,4-methylenedioxyphenyl | 2,5-dimethyl-4-chlorophenyl | | 466 |
| 20 | (R) | H | 2-hydroxyethyl | 3,4-methylenedioxyphenyl | 2,3,6-trimethyl-4-methoxyphenyl | | 481 |
| 21 | (R) | H | 2-propyl | 4-(CH₃OCO)phenyl | 4-methoxyphenyl | 164–165 | 451.1 |
| 22 | (R) | H | 2-propyl | 1-(methyl)indol-5-yl | 2,3,6-trimethyl-4-methoxyphenyl | | 486 |
| 23 | (R) | H | 2-propyl | 3-nitro-4-methylphenyl | 4-methoxyphenyl | | 452 |
| 24 | (R) | H | tert-butoxymethyl | 3,4-methylenedioxyphenyl | 2,3,6-trimethyl-4-methoxyphenyl | | 523 |
| 25 | (R) | H | 2-propyl | 3-fluorophenyl | 4-methoxyphenyl | 159.8–162.8 | 411 |
| 26 | (R) | H | hydroxymethyl | indol-5-yl | 2,5-dimethyl-4-methoxyphenyl | | 448 |
| 27 | (R) | H | 2-propyl | 3-hydroxy-4-methoxy-phenyl | 4-methoxyphenyl | | 439 |
| 28 | (R) | H | 2-propyl | 4-hydroxyphenyl | 4-methoxyphenyl | | 409 |
| 29 | (R) | H | PhCONHCH₂ | 4-(CH₃OCO)phenyl | 4-methoxyphenyl | | 542 |
| 30 | (R) | H | 2-propyl | 3,4-methylenedioxyphenyl | 2-methyl-4-bromophenyl | | 499 |
| 31 | (R) | H | 2-propyl | 4-methylphenyl | 4-methoxyphenyl | 169.6–170.5 | 407 |
| 32 | (R) | H | (CH₃)₂CHCH₂ | 3,4-methylenedioxyphenyl | 2,3,6-trimethyl-4-methoxyphenyl | 137–138 | 493.21 (HRMS) |
| 33 | (R) | H | 2-propyl | 3,4-methylenedioxyphenyl | 2,3,5,6-tetramethylphenyl | | 463 |
| 34 | (R) | H | benzyl | indol-5-yl | 2,3,6-trimethyl-4-methoxyphenyl | | 522 |
| 35 | (R) | H | 2-propyl | benzimidazol-5-yl | 4-methoxyphenyl | | 433 |
| 36 | (R) | H | 2-propyl | 3,4-methylenedioxyphenyl | 2,5-dimethyl-4-methoxyphenyl | | 465 |
| 37 | (R) | H | methoxymethyl | 3,4-methylenedioxyphenyl | 2,3,6-trimethyl-4-methoxyphenyl | | 481 |
| 38 | (R) | H | 2-propyl | 2-(methyl)benzimidazol-5-yl | 4-methoxyphenyl | | 447 |
| 39 | (R) | H | 2-propyl | benzoxazol-5-yl | 4-methoxyphenyl | | 434 |
| 40 | (R) | H | 2-propyl | 3,4-methylenedioxyphenyl | 2,6-dimethyl-4-methoxyphenyl | | 465 |
| 41 | (R) | H | hydroxymethyl | indol-5-yl | 2,5-dimethyl-4-chlorophenyl | | 452 |
| 42 | (R) | H | 2-propyl | 3,4-methylenedioxyphenyl | 4-methylthiophenyl | | 453 |
| 43 | (R) | H | 2-propyl | 4-hydroxymethylphenyl | 4-methoxyphenyl | 96–100 | 423 |
| 44 | (R) | H | 2-propyl | 3-amino-4-hydroxyphenyl | 2,3,6-trimethyl-4-methoxyphenyl | 64–65.5 | 465 |
| 45 | (R) | H | C₆H₅SO₂NHCH₂ | 4-(CH₃OCO)phenyl | 4-methoxyphenyl | | 578 |
| 46 | (R) | H | 2-propyl | 4-(C₆H₅SO₂NH)phenyl | 4-methoxyphenyl | 167.2–169.1 | 548 |

-continued

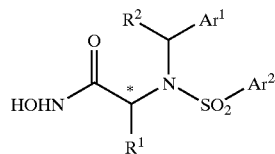

| CPD # | Stereo- chem at *C | R² | R¹ | Ar¹ | Ar² | M. Pt ° C. | Mass Spec. MH+ |
|---|---|---|---|---|---|---|---|
| 47 | (R) | H | indol-3-yl methyl | 3,4-methylenedioxyphenyl | 4-methoxyphenyl | | 524 |
| 48 | (R) | H | C₆H₅CONH CH₂ | 3-nitrophenyl | 4-methoxyphenyl | | 529 |
| 50 | (R) | H | phenyl | 3,4-methylenedioxyphenyl | 4-methoxyphenyl | | 471 |
| 51 | (R) | H | 2-propyl | 4-(CH₃CO)phenyl | 4-methoxyphenyl | 164–164.9 | 435 |
| 52 | (R) | H | 2-propyl | 3,4-ethylenedioxyphenyl | 4-methoxyphenyl | 141–144.5 | 451 |
| 53 | (R) | H | 2-[4-(benzyloxy-carbonyl)pipera zin-1-yl carbonyl]ethyl | 3,4-methylenedioxyphenyl | 2,3,6-trimethyl-4-methoxyphenyl | | 711.4 |
| 54 | (R) | H | 2-(pyridin-3-yl-methylamino-carbonyl)ethyl | 3-fluorophenyl | 4-methoxyphenyl | | 531.2 |
| 55 | (R) | H | 2-[4-phenyl-piperazin-1-yl-carbonyl]ethyl | 3-nitro-4-methylphenyl | 4-methoxyphenyl | | 626.4 |
| 56 | (R) | H | 2-[4-(methoxy-carbonyl)pipera zin-1-yl carbonyl]ethyl | 3,4-methylenedioxyphenyl | 4-methoxyphenyl | | 621.2 |
| 57 | (R) | H | 2-[4-acetyl-piperazin-1-yl carbonyl]ethyl | 3-fluorophenyl | 2,3,6-trimethyl-4-methoxyphenyl | | 593.4 |
| 58 | (R) | H | 2-[4-(ethoxy-carbonyl)pipera zin-1-yl carbonyl]ethyl | 3,4-methylenedioxyphenyl | 2,3,6-trimethyl-4-methoxyphenyl | | 649.4 |
| 59 | (R) | H | 2-[4-(ethoxy-carbonyl)pipera zin-1-yl carbonyl]ethyl | 3-fluorophenyl | 4-methoxyphenyl | | 581.2 |
| 60 | (R) | H | 2-[1-(ethoxy-carbonyl) piperidin-4-yl aminocarbonyl]-ethyl | 3,4-methylenedioxyphenyl | 4-methoxyphenyl | | 621.2 |
| 61 | (R) | H | 2-(thiomorpholin-4-ylcarbonyl) ethyl | 3,4-methylenedioxyphenyl | 4-methoxyphenyl | | 552.2 |
| 62 | (R) | H | 2-[1-(ethoxy-carbonyl) piperidin-4-yl aminocarbonyl]-ethyl | 3,4-methylenedioxyphenyl | 2,3,6-trimethyl-4-methoxyphenyl | | 663.2 |
| 63 | (R) | H | 2-(benzylamino-carbonyl)ethyl | 3,4-methylenedioxyphenyl | 2,3,6-trimethyl-4-methoxyphenyl | | 598.2 |
| 64 | (R) | H | 2-[4-phenyl)-piperazin-1-yl-carbonyl]ethyl | 3,4-methylenedioxyphenyl | 2,3,6-trimethyl-4-methoxyphenyl | | 653.4 |
| 65 | (R) | H | 2-[4-(pyridin-2-yl)-piperazin-1-yl-carbonyl]ethyl | 3-fluorophenyl | 4-methoxyphenyl | | 586.2 |
| 66 | (R) | H | 2-(4-pyridin-4-yl-methylamino-carbonyl)ethyl | 3-fluorophenyl | 4-methoxyphenyl | | 531.2 |
| 67 | (R) | H | 2-(benzylamino-carbonyl)ethyl | 3-fluorophenyl | 4-methoxyphenyl | | 530.2 |

-continued

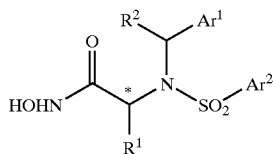

| CPD # | Stereo-chem at *C | R² | R¹ | Ar¹ | Ar² | M. Pt ° C. | Mass Spec. MH+ |
|---|---|---|---|---|---|---|---|
| 68 | (R) | H | 2-[4-(pyridin-2-yl)-piperazin-1-yl-carbonyl]ethyl | 3-fluorophenyl | 2,3,6-trimethyl-4-methoxyphenyl | | 628.4 |
| 69 | (R) | H | 2-(4-acetylpiperazin-1-ylcarbonyl)ethyl | 3-fluorophenyl | 4-methoxyphenyl | | 551.2 |
| 70 | (R) | H | 2-(4-acetylpiperazin-1-ylcarbonyl)ethyl | 3,4-methylenedioxyphenyl | 2,3,6-trimethyl-4-methoxyphenyl | | 619.4 |
| 71 | (R) | H | 2-[1-(ethoxy-carbonyl)piperidin-4-yl aminocarbonyl]ethyl | 3-fluorophenyl | 2,3,6-trimethyl-4-methoxyphenyl | | 637.4 |
| 72 | (R) | H | benzyl | 3,4-methylenedioxyphenyl | 2,3,6-trimethyl-4-methoxy-phenyl | | 493.2063 (HRMS) |
| 73 | (R) | H | 2-propyl | 3,4-methylenedioxyphenyl | 4,8-dimethoxynapth-1-yl | | 517 |
| 74 | (R) | H | 2-propyl | cinnamyl | 4-methoxyphenyl | | 419 |
| 75 | (R) | H | hydroxymethyl | indol-5-yl | 2,6-dimethyl-4-methoxyphenyl | | 448 |
| 76 | (R) | H | hydroxymethyl | 3,4-methylenedioxyphenyl | 2,6-dimethyl-4-methoxyphenyl | 164–165.9 | 453 |
| 77 | (R) | H | (CH₃)₂CH CH₂— | 3,4-methylenedioxyphenyl | 2,3,6-trimethyl-4-methoxyphenyl | 137–138 | 478.19 |
| 78 | (R) | H | 2-propyl | indol-5-yl | 2,6-dimethyl-4-methoxyphenyl | 115–121 | 460 |
| 79 | (R) | H | hydroxymethyl | 3,4-methylenedioxyphenyl | 2,5-dimethyl-4-methoxyphenyl | 135–147.2 | 433 |
| 80 | (R) | H | 1-hydroxyethyl | indo-5-yl | 2,3,6-trimethyl-4-methoxyphenyl | | 409 |
| 81 | (R) | H | 2-propyl | 3-[1-(hydroximino)propyl] indol-5-yl | 2,3,6-trimethyl-4-methoxyphenyl | | 545 |
| 82 | (R) | H | 2-propyl | benzimidazol-5-yl | 2,5,6-trimethyl-4-methoxyphenyl | | 475 |
| 83 | (R) | H | 2-[4-(4-methylphenyl-aminocarbonyl)-piperazin-1-yl-carbonyl]ethyl | 3,4-methylenedioxyphenyl | 2,3,6-trimethyl-4-methoxyphenyl | | 710.8 |
| 84 | (R) | H | 2-[4-(3-methoxyphenyl-aminocarbonyl)-piperazin-1-yl carbonyl]ethyl | 3,4-methylenedioxyphenyl | 2,3,6-trimethyl-4-methoxyphenyl | | 726.8 |
| 85 | (R) | H | benzyl | indol-5-yl | 2,3,6-trimethyl-4-methoxyphenyl | | 522.21 |
| 86 | (R) | H | hydroxymethyl | indol-5-yl | 2,3,6-trimethyl-4-methoxyphenyl | | 462.17 |
| 87 | (R) | H | 1-hydroxyethyl | 3,4-methylenedioxyphenyl | 2,3,6-trimethyl-4-methoxyphenyl | 95–105 | 481 |
| 88 | (R) | H | 2-propyl | 3-[(N-benzyloxy)methyl imidoyl]indol-5-yl | 2,3,6-trimethyl-4-methoxyphenyl | | 621 |
| 89 | (R) | H | 2-(N-methylethyl aminocarbonyl)ethyl | 3,4-methylenedioxyphenyl | 2,3,6-trimethyl-4-methoxyphenyl | | 550.6 |
| 90 | (R) | H | 2-[4-acetyl-piperazin-1-yl-carbonyl]ethyl | 3,4-methylenedioxyphenyl | 2,3,6-trimethyl-4-methoxyphenyl | | 619.7 |

-continued

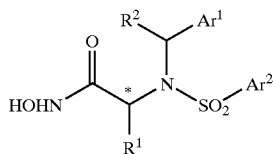

| CPD # | Stereo-chem at *C | R² | R¹ | Ar¹ | Ar² | M. Pt ° C. | Mass Spec. MH+ |
|---|---|---|---|---|---|---|---|
| 91 | (R) | H | 2-[4-(phenoxymethyl-carbonyl)-piperazin-1-yl carbonyl]ethyl | 3,4-methylenedioxyphenyl | 2,3,6-trimethyl-4-methoxyphenyl | | 711.8 |
| 92 | (R) | H | methoxymethyl | indol-5-yl | 2,3,6-trimethyl-4-methoxyphenyl | | 476 |
| 93 | (R) | H | 2[4-(methane sulfonyl)-piperazin-1-yl carbonyl]ethyl | 3,4-methylenedioxyphenyl | 2,3,6-trimethyl-4-methoxyphenyl | | 655.8 |
| 94 | (R) | H | 2-hydroxyethyl | 3,4-methylenedioxyphenyl | 2,3,6-trimethyl-4-methoxyphenyl | | 481.17 |
| 95 | (R) | H | 2-(cyclopropyl amino-carbonyl)ethyl | 3,4-methylenedioxyphenyl | 2,3,6-trimethyl-4-methoxyphenyl | | 548.6 |
| 96 | (R) | H | 2-[4-benzyloxy carbonyl-piperazin-1-yl carbonyl]ethyl | 3,4-methylenedioxyphenyl | 2,3,6-trimethyl-4-methoxyphenyl | | 711.8 |
| 97 | (R) | H | 4-(methoxy carbonyl)phenyl carbonylamino methyl | 3,4-methylenedioxyphenyl | 4-methoxyphenyl | | 586.6 |
| 98 | (R) | H | 3-(benzyloxy carbonylamino) propyl | 3,4-methylenedioxyphenyl | 4-methoxyphenyl | | 586 |
| 99 | (R) | H | 2-(pyrrol-1-yl) phenylcarbonyl aminomethyl | 3,4-methylenedioxyphenyl | 4-methoxyphenyl | | 593.6 |
| 100 | (R) | H | 2-[(diphenyl) methylamino carbonyl]ethyl | 3,4-methylenedioxyphenyl | 4-methoxyphenyl | | 632.7 |
| 101 | (R) | H | 3-cyanophenyl aminocarbonyl aminomethyl | 3,4-methylenedioxyphenyl | 4-methoxyphenyl | | 568.6 |
| 102 | (R) | H | thien-2-yl carbonyl aminomethyl | 3,4-methylenedioxyphenyl | 4-methoxyphenyl | | 534.6 |
| 103 | (R) | H | phenylcarbonyl aminomethyl | 3,4-methylenedioxyphenyl | 4-methoxyphenyl | | 528.6 |
| 104 | (R) | H | $(C_6H_5)CHCH_3N HCO(C_2H_4)CO NHCH_2$— | 3,4-methylenedioxyphenyl | 4-methoxyphenyl | | 627.7 |
| 105 | (R) | H | (4-methoxyphenyl) $COC_2H_4CONH CH_2$— | 3,4-methylenedioxyphenyl | 4-methoxyphenyl | | 614.6 |
| 106 | (R) | H | 4-chlorophenyl sulfonylamino carbonyl aminomethyl | 3,4-methylenedioxyphenyl | 4-methoxyphenyl | | 642.1 |
| 107 | (R) | H | 5-(acetyl) thien-2-yl carbonyl aminomethyl | 3,4-methylenedioxyphenyl | 4-methoxyphenyl | | 576.6 |
| 108 | (R) | H | pyridin-3-yl carbonylamino methyl | 3,4-methylenedioxyphenyl | 4-methoxyphenyl | | 529.5 |
| 109 | (R) | H | 2-[2-(methyl)butyl aminocarbonyl] ethyl | 3,4-methylenedioxyphenyl | 4-methoxyphenyl | | 536.6 |

-continued

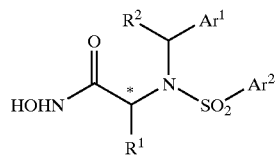

| CPD # | Stereo-chem at *C | R² | R¹ | Ar¹ | Ar² | M. Pt ° C. | Mass Spec. MH+ |
|---|---|---|---|---|---|---|---|
| 110 | (R) | H | (3,4,5-trimethoxyphenyl)C₂H₄CONHCH₂ | 3,4-methylenedioxyphenyl | 4-methoxyphenyl | | 646.7 |
| 111 | (R) | H | 3-methoxyphenylaminocarbonylaminomethyl | 3,4-methylenedioxyphenyl | 4-methoxyphenyl | | 573.6 |
| 112 | (R) | H | 2-[(C₆H₅)CHCH₃NHCO]ethyl | 3,4-methylenedioxyphenyl | 4-methoxyphenyl | | 570.6 |
| 113 | (R) | H | (phenoxy)CH(CH₂CH₃)CONHCH₂— | 3,4-methylenedioxyphenyl | 4-methoxyphenyl | | 586.6 |
| 114 | (R) | H | (3-nitrophenyl)CH₂SO₂NHCH₂ | 3,4-methylenedioxyphenyl | 4-methoxyphenyl | | 623.6 |
| 115 | (R) | H | 1-(ethoxycarbonyl)piperidin-4-yl-aminomethylcarbonylaminomethyl | 3,4-methylenedioxyphenyl | 4-methoxyphenyl | | 636.7 |
| 116 | (R) | H | 4-ethoxyphenylaminocarbonylaminomethyl | 3,4-methylenedioxyphenyl | 4-methoxyphenyl | | 587.6 |
| 117 | (R) | H | 2-chloropyridin-5-ylcarbonylaminomethyl | 3,4-methylenedioxyphenyl | 4-methoxyphenyl | | 564.0 |
| 118 | (R) | H | 2-[N,N-(ethylcyano)(benzyl)aminocarbonyl]ethyl | 3,4-methylenedioxyphenyl | 4-methoxyphenyl | | 609.7 |
| 119 | (R) | H | 4-(methylthio)phenylaminocarbonylaminomethyl | 3,4-methylenedioxyphenyl | 4-methoxyphenyl | | 589.7 |
| 120 | (R) | H | 2,4-difluorophenylcarbonylaminomethyl | 3,4-methylenedioxyphenyl | 4-methoxyphenyl | | 564.5 |
| 121 | (R) | H | 2-propyl | 3-(acetyl)indol-5-yl | 4-methoxyphenyl | | 474 |
| 122 | (R) | H | 2-[4-(phenylcarbonyl)piperazin-1-ylcarbonyl]ethyl | 3,4-methylenedioxyphenyl | 4-methoxyphenyl | | 639.7 |
| 123 | (R) | H | (4-hydroxyphenoxy)CH(CH₃)CONHCH₂— | 3,4-methylenedioxyphenyl | 4-methoxyphenyl | | 588.6 |
| 124 | (R) | H | 2-[4-(furan-2-ylcarbonyl)piperidin-1-ylcarbonyl]ethyl | 3,4-methylenedioxyphenyl | 4-methoxyphenyl | | 629.7 |
| 125 | (R) | H | N-(3,5-(dimethoxy)phenylcarbonyl)aminomethyl | 3,4-methylenedioxyphenyl | 4-methoxyphenyl | | 588.6 |
| 126 | (R) | H | 2-propyl | 3-(acetyl)indol-5-yl | 2,3,6-trimethyl-4-methoxyphenyl | 163–171 | 516 |
| 127 | (R) | H | 2-propyl | 3-(isobutyro)indol-5-yl | 2,3,6-trimethyl-4-methoxyphenyl | | 544 |

-continued

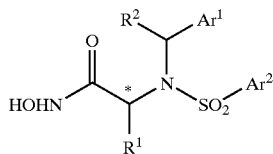

| CPD # | Stereo-chem at *C | R² | R¹ | Ar¹ | Ar² | M. Pt ° C. | Mass Spec. MH+ |
|---|---|---|---|---|---|---|---|
| 128 | (R) | H | methylsulfonyl aminomethyl | 3,4-methylenedioxyphenyl | 2,6-dimethyl-4-methoxyphenyl | 98–102 | 530 |
| 129 | (R) | H | phenylsulfonyl aminomethyl | 3,4-methylenedioxyphenyl | 2,6-dimethyl-4-methoxyphenyl | 103–107 | 592 |
| 130 | (R) | H | acetylamino methyl | 3,4-methylenedioxyphenyl | 2,6-dimethyl-4-methoxyphenyl | | 494 |
| 131 | (R) | H | methoxy carbonyl aminomethyl | 3,4-methylenedioxyphenyl | 2,6-dimethyl-4-methoxyphenyl | | 510 |
| 132 | (R) | H | 4-carboxyphenyl carbonylamino methyl | 3,4-methylenedioxyphenyl | 2,6-dimethyl-4-methoxyphenyl | 150–153 | 600 |
| 133 | (R) | H | 4-methyl benzoate carboxamido methyl | 3,4-methylenedioxyphenyl | 2,6-dimethyl-4-methoxyphenyl | 119–124 | 614 |
| 134 | (R) | H | (2-pyrrol-1-yl) phenylcarbonyl | 3,4-methylenedioxyphenyl | 2,6-dimethyl-4-methoxyphenyl | 104–108 | 621 |
| 135 | (R) | H | 4-(methoxy carbonyl)phenyl carbonyl aminomethyl | indol-5-yl | 2,6-dimethyl-4-methoxyphenyl | 122–127 | 609 |
| 136 | (R) | H | 1-hydroxyethyl | benzimidazol-5-yl | 2,3,6-trimethyl-4-methoxyphenyl | | 477 |
| 137 | (R) | H | (imidazol-4-yl) methyl | 3,4-methylenedioxyphenyl | 2,6-dimethyl-4-methoxyphenyl | | 503 |
| 138 | (R) | H | N-(phenyl carbonyl)amino methyl | 3,4-methylenedioxyphenyl | 2,6-dimethyl-4-methoxyphenyl | | 556 |
| 139 | (R) | H | 2-chlorophenyl methoxy carbonylamino methyl | 3,4-methylenedioxyphenyl | 4-methoxyphenyl | | 592 |
| 140 | (R) | H | 3-nitrophenyl methoxy carbonylamino methyl | 3,4-methylenedioxyphenyl | 4-methoxyphenyl | | 603 |
| 141 | (R) | H | 3,5-dichloro phenylmethoxy carbonylamino methyl | 3,4-methylenedioxyphenyl | 4-methoxyphenyl | | 626 |
| 142 | (R) | H | 2-propyl | benzoxazol-5-yl | 4-methoxyphenyl | | 434 |
| 143 | (R) | H | 2-(pyrrol-1-yl) benzamido methyl | 3,4-methylenedioxyphenyl | 2,6-dimethyl-4-methoxyphenyl | | 621 |
| 144 | (R) | H | 1-hydroxyethyl | 3,4-methylenedioxyphenyl | 2,6-dimethyl-4-methoxyphenyl | | 467 |
| 145 | (R) | H | 2-propyl | indol-5-yl | 2,5-dimethyl-4-methoxyphenyl | 117–121 | 460 |
| 146 | (R) | H | benzyloxy carbonylamino methyl | 3,4-methylenedioxyphenyl | 4-methoxyphenyl | | 558 |
| 147 | (R) | H | 4-methoxyaniline carbonylamino methyl | 3,4-methylenedioxyphenyl | 4-methoxyphenyl | | 573 |
| 148 | (R) | H | 4-nitrobenzyloxy carbonylamino methyl | 3,4-methylenedioxyphenyl | 4-methoxyphenyl | | 603 |
| 149 | (R) | H | 2-bromo benzyloxy carbonylamino methyl | 3,4-methylenedioxyphenyl | 4-methoxyphenyl | | 638 |

II. Compounds of the Formula (Ia) and (Ib) wherein R is —CH($R^2$)$Ar^1$, $Ar^2$ is 2,3,6 trimethyl-4-methoxyphenyl or 2,6-dimethyl-4-methoxyphenyl, $R^2$ is hydrogen, and the other groups are defined as follows:

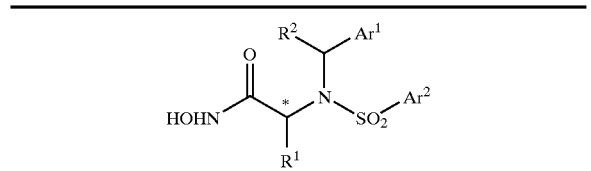

| CPD # | $R^1$ | $Ar^1$ |
|---|---|---|
| 1 | N-[4-(methoxycarbonyl)phenylcarbonyl]aminomethyl | 3,4-methylenedioxyphenyl |
| 2 | N-(benzyloxycarbonyl)aminopropyl | 3,4-methylenedioxyphenyl |
| 3 | N-[2-(pyrrol-1-yl)phenylcarbonyl]aminomethyl | 3,4-methylenedioxyphenyl |
| 4 | 2-[(diphenyl)methylaminocarbonyl]ethyl | 3,4-methylenedioxyphenyl |
| 5 | N-[3-(cyano)phenylaminocarbonyl]aminomethyl | 3,4-methylenedioxyphenyl |
| 6 | N-(thien-2-ylcarbonyl)aminomethyl | 3,4-methylenedioxyphenyl |
| 7 | N-(phenylcarbonyl)aminomethyl | 3,4-methylenedioxyphenyl |
| 8 | ($C_6H_5$)$CHCH_3$NHCO($C_2H_4$)$CONHCH_2$— | 3,4-methylenedioxyphenyl |
| 9 | (4-methoxyphenyl)$COC_2H_4CONHCH_2$— | 3,4-methylenedioxyphenyl |
| 10 | N-(4-chlorophenylsulfonylaminocarbonyl)aminomethyl | 3,4-methylenedioxyphenyl |
| 11 | N-(5-(acetyl)thien-2-ylcarbonyl)aminomethyl | 3,4-methylenedioxyphenyl |
| 12 | N-(pyridin-3-ylcarbonyl)aminomethyl | 3,4-methylenedioxyphenyl |
| 13 | 2-[2-(methyl)butylaminocarbonyl]ethyl | 3,4-methylenedioxyphenyl |
| 14 | (3,4,5-trimethoxyphenyl)$C_2H_4CONHCH_2$— | 3,4-methylenedioxyphenyl |
| 15 | N-(3-(methoxy)phenylaminocarbonyl)aminomethyl | 3,4-methylenedioxyphenyl |
| 16 | 2-[($C_6H_5$)$CHCH_3$NHCO]ethyl | 3,4-methylenedioxyphenyl |
| 17 | (phenoxy)CH($CH_2CH_3$)$CONHCH_2$— | 3,4-methylenedioxyphenyl |
| 18 | (3-nitrophenyl)$CH_2SO_2NHCH_2$— | 3,4-methylenedioxyphenyl |
| 19 | N-[1-(ethoxycarbonyl)-piperidin-4-yl-aminomethylcarbonyl)aminomethyl | 3,4-methylenedioxyphenyl |
| 20 | N-(4-(ethoxy)phenylaminocarbonyl)aminomethyl | 3,4-methylenedioxyphenyl |
| 21 | N-(2-chloropyridin-5-ylcarbonyl)aminomethyl | 3,4-methylenedioxyphenyl |
| 22 | 2-[N,N-(ethylcyano)(benzyl)aminocarbonyl]ethyl | 3,4-methylenedioxyphenyl |
| 23 | N-(4-(methylthio)anilinocarbonyl)aminomethyl | 3,4-methylenedioxyphenyl |
| 24 | N-(2,4-difluorophenylcarbonyl)aminomethyl | 3,4-methylenedioxyphenyl |
| 25 | 2-propyl | (3-acetyl)indol-5-yl |
| 26 | 2-[4-(phenylcarbonyl)piperazin-1-ylcarbonyl]ethyl | 3,4-methylenedioxyphenyl |
| 27 | (4-hydroxyphenoxy)CH($CH_3$)$CONHCH_2$— | 3,4-methylenedioxyphenyl |
| 28 | 2-[4-(furan-2-ylcarbonyl)piperidin-1-ylcarbonyl]ethyl | 3,4-methylenedioxyphenyl |
| 29 | N-(3,5-(dimethoxy)phenylcarbonyl)aminomethyl | 3,4-methylenedioxyphenyl |
| 30 | N-(benzyloxycarbonyl)aminopropyl | benzoxazol-6-yl |
| 31 | N-(benzyloxycarbonyl)aminopropyl | benzofuran-5-yl |

PREFERRES EMBODIMENTS

While the broadest definition of this invention is set forth in the Summary of the Invention, certain compounds of Formula (Ia) wherein Z is NHOH are preferred.

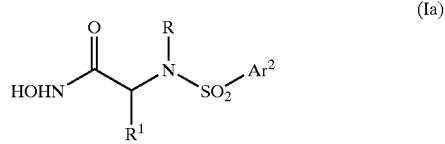

In addition, compounds of Formula (Ia) where $Ar^2$ is at least tetra or penta-substituted are surprisingly selective in inhibiting procollagen C-proteinase relative to other collagenases.

I. A preferred group of compounds is that wherein:
  R is —CH($R^2$)$Ar^1$ wherein $R^2$ is hydrogen.
  (a) Within this preferred group (I) a more preferred group of compounds of that wherein:
     $Ar^1$ is heteroaryl and $Ar^2$ is a phenyl ring of formula (a).
     (i) Within this more preferred group (I)(a), an even more preferred group of compounds is that wherein:
        $R^3$ and $R^7$ are, independently of each other, alkyl, alkylthio, or halo;
        $R^4$ is hydrogen, alkyl, or halo;
        $R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl; and
        $R^6$ is hydrogen.
     Within these preferred, more preferred and even more preferred groups of compounds, a particularly preferred group of compounds is that wherein:
        $Ar^1$ is a heteroaryl ring, preferably optionally substituted indolyl or imidazolyl, more preferably indol-5-yl, 1-methylindol-5-yl, 3-acetylindol-5-yl, 3-propionylindol-5-yl, 3-(2-methylpropionyl)indol-5-yl, imidazol-5-yl, 2-methylbenzimidazol-5-yl, or benzimidazol-5-yl;
        $R^3$ and $R^7$ are, independently of each other, alkyl or halo, more preferably methyl, chloro, or bromo;
        $R^4$ is hydrogen or alkyl, preferably methyl; and
        $R^5$ is alkyl, alkoxy, or halo, preferably methyl, methoxy, chloro, or bromo.
     Within these preferred, more preferred, and particularly preferred groups of compounds, an even more particularly preferred group of compounds is that wherein:
        $R^1$ is alkyl, aralkyl, heteroalkyl, or -(alkylene)-C(O)—X where X is alkyl, amino, monosubstituted amino, disubstituted amino, or heterocyclyl,
           more preferably 2-propyl, hydroxymethyl, tert-butoxymethyl, 2-hydroxyethyl, 2-hydroxypropyl, 2-amidopropyl, acetyloxymethyl, benzyl, methoxymethyl, or -(alkylene)-C(O)—X where X is 2- or 4-pyridylmethylamino, 1-alkoxycarbonylpyridin-4-ylamino, optionally substituted benzylamino, 4-optionally substituted benzyloxycarbonylpiperazin-1-yl, 4-optionally substituted phenylpiperazin-1-yl, 4-alkoxycarbonylpiperazin-1-yl, or 4-optionally substituted heteroarylpiperazin-1-yl,
           most preferably 2-propyl, hydroxymethyl, tert-butoxymethyl, 2-hydroxyethyl, 2-hydroxypropyl, 2-amidopropyl, acetyloxymethyl, benzyl, methoxymethyl, 2-(2- or 4-pyridylmethylaminocarbonyl)ethyl, 2-(1-ethoxycarbonylpyridin-4-ylaminocarbonyl)-ethyl, 2-(benzylaminocarbonyl) ethyl, 2-(4-benzyloxycarbonylpiperizin-1-ylcarbonyl)-ethyl, 2-(4-phenylpiperazin-1-ylcarbonyl)-ethyl, 2-(4-methoxycarbonylpiperazin-1-ylcarbonyl)ethyl, 2-(4-acetylpiperazin-1-ylcarbonyl)ethyl, or 2-(4-pyridin-2-ylpiperazin-1-ylcarbonyl)ethyl.

Within these preferred, more preferred, and particularly preferred groups of compounds, an alternative even more particularly preferred group of compounds is that wherein:

$R^1$ is heteroalkyl or -(alkylene)-C(O)—X where X is alkyl, amino, monosubstituted amino, disubstituted amino, or heterocyclyl, more preferably, methylsulfonylaminomethyl, phenylsulfonylaminomethyl, (3-nitrophenyl) $CH_2SO_2NHCH_2$, methylcarbonylaminomethyl, 4-(methoxycarbonyl)phenylcarbonylaminomethyl, 2-(pyrrol-1-yl)phenylcarbonylaminomethyl, 3-cyanophenylaminocarbonylaminomethyl, thien-2-ylcarbonylaminomethyl, phenylcarbonylaminomethyl, $(C_6H_5)CHCH_3NHCO(C_2H_4)CONHCH_2$, (4-methoxyphenyl) $COC_2H_4CONHCH_2$, 4-chlorophenylsulfonylaminocarbonylaminomethyl, 5-(acetyl)thien-2-ylcarbonylaminomethyl, pyridin-3-ylcarbonylaminomethyl, (3,4,5-trimethoxyphenyl) $C_2H_4CONHCH_2$, 3-methoxyphenylaminocarbonylaminomethyl, (phenoxy)$CH(CH_2CH_3)CONHCH_2$, 1-(ethoxycarbonyl)piperidin-4-yl-aminomethylcarbonylaminomethyl, 3-(benzyloxycarbonylamino)propyl, 2-[(diphenyl) methylaminocarbonyl]ethyl, 2-[2-(methyl) butylaminocarbonyl]ethyl, or 2-[$(C_6H_5)$ $CHCH_3NHCO$]ethyl.

(ii) Within this more preferred group (I)(a), another even more preferred group of compounds is that wherein:

$R^4$ and $R^6$ are hydrogen;

$R^3$ and $R^7$ are, independently of each other, alkyl, or halo; and $R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl.

Within these preferred, more preferred, and even more preferred groups of compounds, a particularly preferred group of compounds is that wherein:

$Ar^1$ is a heteroaryl ring, preferably optionally substituted indolyl or imidazolyl, more preferably indol-5-yl, 1-methylindol-5-yl, 3-acetylindol-5-yl, 3-propionylindol-5-yl, 3-(2-methylpropionyl)indol-5-yl, imidazol-5-yl, 2-methylbenzimidazol-5-yl, or benzimidazol-5-yl;

$R^3$ is alkyl, preferably methyl;

$R^5$ is alkyl, alkoxy, or halo, preferably methyl, methoxy, chloro, or bromo; and $R^7$ is alkyl or halo, preferably methyl, chloro, or bromo.

Within these preferred, more preferred, and particularly preferred group of compounds, an even more particularly preferred group of compounds is that wherein:

$R^1$ is alkyl, aralkyl, heteroalkyl, or -(alkylene)-C(O)—X where X is alkyl, amino, monosubstituted amino, disubstituted amino, or heterocyclyl, more preferably 2-propyl, hydroxymethyl, tert-butoxymethyl, 2-hydroxyethyl, 2-hydroxypropyl, 2-amidopropyl, acetyloxymethyl, benzyl, methoxymethyl, or -(alkylene)-C(O)—X where X is 2- or 4-pyridylmethylamino, 1-alkoxycarbonylpyridin-4-ylamino, optionally substituted benzylamino, 4-optionally substituted benzyloxycarbonylpiperazin-1-yl, 4-optionally substituted phenylpiperazin-1-yl, 4-alkoxycarbonylpiperazin-1-yl, or 4-optionally substituted heteroarylpiperazin-1-yl, most preferably 2-propyl, hydroxymethyl, tert-butoxymethyl, 2-hydroxyethyl, 2-hydroxypropyl, 2-amidopropyl, acetyloxymethyl, benzyl, methoxymethyl, 2-(2- or 4-pyridylmethylaminocarbonyl)ethyl, 2-(1-ethoxycarbonylpyridin-4-ylaminocarbonyl)ethyl, 2-(benzylaminocarbonyl)ethyl, 2-(4-benzyloxycarbonylpiperizin-1-ylcarbonyl)ethyl, 2-(4-phenylpiperazin-1-ylcarbonyl)ethyl, 2-(4-methoxycarbonylpiperazin-1-ylcarbonyl)ethyl, 2-(4-acetylpiperazin-1-yl-carbonyl)ethyl, or 2-(4-pyridin-2-ylpiperazin-1-ylcarbonyl)ethyl.

Within these preferred, more preferred, and particularly preferred groups of compounds, an alternative even more particularly preferred group of compounds is that wherein:

$R^1$ is heteroalkyl or -(alkylene)-C(O)—X where X is alkyl, amino, monosubstituted amino, disubstituted amino, or heterocyclyl, more preferably, methylsulfonylaminomethyl, phenylsulfonylaminomethyl, (3-nitrophenyl) $CH_2SO_2NHCH_2$, methylcarbonylaminomethyl, 4-(methoxycarbonyl)phenylcarbonylaminomethyl, 2-(pyrrol-1-yl)phenylcarbonylaminomethyl, 3-cyanophenylaminocarbonylaminomethyl, thien-2-ylcarbonylaminomethyl, phenylcarbonylaminomethyl, $(C_6H_5)CHCH_3NHCO(C_2H_4)CONHCH_2$, (4-methoxyphenyl) $COC_2H_4CONHCH_2$, 4-chlorophenylsulfonylaminocarbonylaminomethyl, 5-(acetyl)thien-2-ylcarbonylaminomethyl, pyridin-3-ylcarbonylaminomethyl, (3,4,5-trimethoxyphenyl) $C_2H_4CONHCH_2$, 3-methoxyphenylaminocarbonylaminomethyl, (phenoxy)$CH(CH_2CH_3)CONHCH_2$, 1-(ethoxycarbonyl)piperidin-4-yl-aminomethylcarbonylaminomethyl, 3-(benzyloxycarbonylamino)propyl, 2-[(diphenyl) methylaminocarbonyl]ethyl, 2-[2-(methyl) butylaminocarbonyl]ethyl, or 2-[$(C_6H_5)$ $CHCH_3NHCO$]ethyl.

(b) Within this preferred group (I), another more preferred group of compounds is that wherein:

$Ar^1$ is aryl and $Ar^2$ is a phenyl ring of formula (a).

(i) Within this more preferred group (I)(b), an even more preferred group of compounds is that wherein:

$R^3$ and $R^7$ are, independently of each other, alkyl, alkylthio, or halo;

$R^4$ is hydrogen, alkyl, or halo;

$R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl; and $R^6$ is hydrogen.

Within these preferred, more preferred and even more preferred groups of compounds, a particularly preferred group of compounds is that wherein:

Ar¹ is a phenyl ring substituted with one or two substituents selected from hydroxy, methylenedioxy, or methoxycarbonyl, more preferably, 3,4-methylenedioxyphenyl, 3,4-dihydroxyphenyl, or 4-methoxycarbonylphenyl;

$R^3$ and $R^7$ are, independently of each other, alkyl or halo, more preferably methyl, chloro, or bromo;

$R^4$ is alkyl, preferably methyl; and $R^5$ is alkyl, alkoxy, or halo, preferably methyl, methoxy, chloro, or bromo.

Within these preferred, more preferred, and particularly preferred group of compounds, an even more particularly preferred group of compounds is that wherein:

$R^1$ is alkyl, aralkyl, heteroalkyl, or -(alkylene)-C(O)—X where X is alkyl, amino, monosubstituted amino, disubstituted amino, or heterocyclyl,
   more preferably 2-propyl, hydroxymethyl, tert-butoxymethyl, 2-hydroxyethyl, 2-hydroxypropyl, 2-amidopropyl, acetyloxymethyl, benzyl, methoxymethyl, or -(alkylene)-C(O)—X where X is 2- or 4-pyridylmethylamino, 1-alkoxycarbonylpyridin-4-ylamino, optionally substituted benzylamino, 4-optionally substituted benzyloxycarbonylpiperazin-1-yl, 4-optionally substituted phenylpiperazin-1-yl, 4-alkoxycarbonylpiperazin-1-yl, or 4-optionally substituted heteroarylpiperazin-1-yl,
   most preferably 2-propyl, hydroxymethyl, tert-butoxymethyl, 2-hydroxyethyl, 2-hydroxypropyl, 2-amidopropyl, acetyloxymethyl, benzyl, methoxymethyl, 2-(2- or 4-pyridylmethylaminocarbonyl)ethyl, 2-(1-ethoxycarbonylpyridin-4-ylaminocarbonyl)ethyl, 2-(benzylaminocarbonyl)ethyl, 2-(4-benzyloxycarbonylpiperazin-1-ylcarbonyl)ethyl, 2-(4-phenylpiperazin-1-ylcarbonyl)ethyl, 2-(4-methoxycarbonylpiperazin-1-ylcarbonyl)ethyl, 2-(4-acetylpiperazin-1-yl-carbonyl)ethyl, or 2-(4-pyridin-2-ylpiperazin-1-ylcarbonyl)ethyl.

Within these preferred, more preferred, and particularly preferred groups of compounds, an alternative even more particularly preferred group of compounds is that wherein:

$R^1$ is heteroalkyl or -(alkylene)-C(O)—X where X is alkyl, amino, monosubstituted amino, disubstituted amino, or heterocyclyl,
   more preferably, methylsulfonylaminomethyl, phenylsulfonylaminomethyl, (3-nitrophenyl)CH₂SO₂NHCH₂, methylcarbonylaminomethyl, 4-(methoxycarbonyl)phenylcarbonylaminomethyl, 2-(pyrrol-1-yl)phenylcarbonylaminomethyl, 3-cyanophenylaminocarbonylaminomethyl, thien-2-ylcarbonylaminomethyl, phenylcarbonylaminomethyl, (C₆H₅)CHCH₃NHCO(C₂H₄)CONHCH₂, (4-methoxyphenyl)COC₂H₄CONHCH₂, 4-chlorophenylsulfonylaminocarbonylaminomethyl, 5-(acetyl)thien-2-ylcarbonylaminomethyl, pyridin-3-ylcarbonylaminomethyl, (3,4,5-trimethoxyphenyl)C₂H₄CONHCH₂, 3-methoxyphenylaminocarbonylaminomethyl, (phenoxy)CH(CH₂CH₃)CONHCH₂, 1-(ethoxycarbonyl)piperidin-4-yl-aminomethylcarbonylaminomethyl, 3-(benzyloxycarbonylamino)propyl, 2-[(diphenyl)methylaminocarbonyl]ethyl, 2-[2-(methyl)butylaminocarbonyl]ethyl, or 2-[(C₆H₅)CHCH₃NHCO]ethyl.

(ii) Another even more preferred group of compounds in group (I)(b), is that wherein:

$R^4$ and $R^6$ are hydrogen;

$R^3$ and $R^7$ are, independently of each other, alkyl, or halo; and $R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl.

Within these preferred, more preferred and even more preferred groups of compounds, a particularly preferred group of compounds is that wherein:

Ar¹ is a phenyl ring substituted with one or two substituents selected from hydroxy, methylenedioxy, or methoxycarbonyl, more preferably, 3,4-methylenedioxyphenyl, 3,4-dihydroxyphenyl, or 4-methoxycarbonylphenyl;

$R^3$ is alkyl, preferably methyl;

$R^5$ is alkyl, alkoxy, or halo, preferably methyl, methoxy, chloro, or bromo; and $R^7$ is alkyl or halo, preferably methyl, chloro, or bromo.

Within these preferred, more preferred, and particularly preferred group of compounds, an even more particularly preferred group of compounds is that wherein:

$R^1$ is alkyl, hydroxyalkyl, aralkyl, heteroalkyl, or -(alkylene)-C(O)—X where X is alkyl, amino, monosubstituted amino, disubstituted amino, or heterocyclyl,
   more preferably 2-propyl, hydroxymethyl, tert-butoxymethyl, 2-hydroxyethyl, 2-hydroxypropyl, 2-amidopropyl, acetyloxymethyl, benzyl, methoxymethyl, or -(alkylene)-C(O)—X where X is 2- or 4-pyridylmethylamino, 1-alkoxycarbonylpyridin-4-ylamino, optionally substituted benzylamino, N-(optionally substituted carbonyl)methylamino, N-(optionally substituted amido)methylamino, 4-optionally substituted benzyloxycarbonylpiperazin-1-yl, 4-optionally substituted phenylpiperazin-1-yl, 4-alkoxycarbonylpiperazin-1-yl, or 4-optionally substituted heteroarylpiperazin-1-yl, 4-methanesulfonyl-piperazin-1-yl, 4-acetylpiperazin-1-yl, 4-optionally substituted phenoxypiperazin-1-yl, most preferably 2-propyl, hydroxymethyl, tert-butoxymethyl, 2-hydroxyethyl, 2-hydroxypropyl, 2-amidopropyl, acetyloxymethyl, benzyl, methoxymethyl, 2-(2- or 4-pyridylmethylamino-carbonyl)ethyl, 2-(1-ethoxycarbonylpyridin-4-ylaminocarbonyl)-ethyl, 2-(benzylaminocarbonyl)ethyl, 2-(4-benzyloxycarbonylpiperazin-1-ylcarbonyl)-ethyl, 2-(4-phenylpiperazin-1-ylcarbonyl)-ethyl, 2-(4-methoxycarbonylpiperazin-1-ylcarbonyl)ethyl, 2-(4-acetylpiperazin-1-yl-carbonyl)ethyl, or 2-(4-pyridin-2-ylpiperazin-1-ylcarbonyl)ethyl.

Within these preferred, more preferred, and particularly preferred groups of compounds, an alternative even more particularly preferred group of compounds is that wherein:

$R^1$ is heteroalkyl or -(alkylene)-C(O)—X where X is alkyl, amino, monosubstituted amino, disubstituted amino, or heterocyclyl,
   more preferably, methylsulfonylaminomethyl, phenylsulfonylaminomethyl, (3-nitrophenyl)

$CH_2SO_2NHCH_2$, methylcarbonylaminomethyl, 4-(methoxycarbonyl)phenylcarbonylaminomethyl, 2-(pyrrol-1-yl)phenylcarbonylaminomethyl, 3-cyanophenylaminocarbonylaminomethyl, thien-2-ylcarbonylaminomethyl, phenylcarbonylaminomethyl, $(C_6H_5)CHCH_3NHCO(C_2H_4)CONHCH_2$, (4-methoxyphenyl)$COC_2H_4CONHCH_2$, 4-chlorophenylsulfonylaminocarbonylaminomethyl, 5-(acetyl)thien-2-ylcarbonylaminomethyl, pyridin-3-ylcarbonylaminomethyl, (3,4,5-trimethoxyphenyl)$C_2H_4CONHCH_2$, 3-methoxyphenylaminocarbonylaminomethyl, (phenoxy)$CH(CH_2CH_3)CONHCH_2$, 1-(ethoxycarbonyl)piperidin-4-yl-aminomethylcarbonylaminomethyl, 3-(benzyloxycarbonylamino)propyl, 2-[(diphenyl)methylaminocarbonyl]ethyl, 2-[2-(methyl)butylaminocarbonyl]ethyl, or 2-[$(C_6H_5)$CHCH$_3$NHCO]ethyl.

II. Another preferred group of compounds is that wherein:
R is —CH($R^2$)Ar$^1$ wherein $R^2$ is alkyl.

Within this group (II), a more preferred group of compounds is that wherein:

(a) Ar$^1$ is a heteroaryl ring, preferably optionally substituted indolyl or imidazolyl, more preferably indol-5-yl, 1-methylindol-5-yl, 3-acetylindol-5-yl, 3-propionylindol-5-yl, 3-(2-methylpropionyl)indol-5-yl, imidazol-5-yl, 2-methylbenzimidazol-5-yl, benzimidazol-5-yl; and
Ar$^2$ is a phenyl ring of formula (a).

Another more preferred group of compounds is that wherein:

(b) Ar$^1$ is aryl, preferably a phenyl ring substituted with one or two substituents selected from hydroxy, methylenedioxy, or methoxycarbonyl, more preferably, 3,4-methylenedioxyphenyl, 3,4-dihydroxyphenyl, or 4-methoxycarbonylphenyl; and
Ar$^2$ is a phenyl ring of formula (a).
Within the more preferred groups II (a) and (b), an even more preferred group of compounds is that wherein:
(i) $R^3$ and $R^7$ are, independently of each other, hydrogen, alkyl, alkylthio, or halo, preferably methyl, methylthio, chloro, or bromo, more preferably methyl, chloro, or bromo;
$R^4$ is hydrogen, alkyl or halo, preferably methyl, chloro, or bromo;
$R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl, preferably alkyl, alkoxy, or halo, more preferably methyl, methoxy, chloro, or bromo; and
$R^6$ is hydrogen.
(ii) Another even more preferred group of compounds within groups II(a) and (b) is that wherein:
$R^3$ and $R^6$ are hydrogen;
$R^4$ and $R^7$ are, independently of each other, alkyl, or halo, preferably methyl, chloro, or bromo; and
$R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl, preferably alkyl, alkoxy, or halo, more preferably methyl, methoxy, chloro, or bromo.

(iii) Another even more preferred group of compounds within groups II (a) and (b) is that wherein:
$R^4$ and $R^6$ are hydrogen
$R^3$ and $R^7$ are, independently of each other, alkyl, or halo; and
$R^5$ is alkyl, haloalkyl, alkylthio, alkoxy, alkyloxycarbonyl, aryloxy, hydroxy, halo, cyano, carboxy, nitro, amino, monoalkylamino, dialkylamino, or alkylsulfonyl.
Within the above preferred, more preferred and an even more preferred groups of (II)a and (II)b, a particularly preferred group of compounds is that wherein:
$R^1$ is alkyl, aralkyl, heteroalkyl, or -(alkylene)-C(O)—X where X is alkyl, amino, monosubstituted amino, disubstituted amino, or heterocyclyl,
more preferably 2-propyl, hydroxymethyl, tert-butoxymethyl, 2-hydroxyethyl, 2-hydroxypropyl, 2-amidopropyl, acetyloxymethyl, benzyl, methoxymethyl, or -(alkylene)-C(O)—X where X is 2- or 4-pyridylmethylamino, 1-alkoxycarbonylpyridin-4-ylamino, optionally substituted benzylamino, 4-optionally substituted benzyloxycarbonylpiperazin-1-yl, 4-optionally substituted phenylpiperazin-1-yl, 4-alkoxycarbonylpiperazin-1-yl, or 4-optionally substituted heteroarylpiperazin-1-yl,
most preferably 2-propyl, hydroxymethyl, tert-butoxymethyl, 2-hydroxyethyl, 2-hydroxypropyl, 2-amidopropyl, acetyloxymethyl, benzyl, methoxymethyl, 2-(2- or 4-pyridylmethylaminocarbonyl)ethyl, 2-(1-ethoxycarbonylpyridin-4-ylaminocarbonyl)ethyl, 2-(benzylaminocarbonyl)ethyl, 2-(4-benzyloxycarbonylpiperizin-1-ylcarbonyl)ethyl, 2-(4-phenylpiperazin-1-ylcarbonyl)ethyl, 2-(4-methoxycarbonylpiperazin-1-ylcarbonyl)ethyl, 2-(4-acetylpiperazin-1-yl-carbonyl)ethyl, or 2-(4-pyridin-2-ylpiperazin-1-ylcarbonyl)ethyl.
Within the above preferred, more preferred and even more preferred groups of (II), an alternative particularly preferred group of compounds is that wherein:
$R^1$ is heteroalkyl or -(alkylene)-C(O)—X where X is alkyl, amino, monosubstituted amino, disubstituted amino, or heterocyclyl,
more preferably, methylsulfonylaminomethyl, phenylsulfonylaminomethyl, (3-nitrophenyl)$CH_2SO_2NHCH_2$, methylcarbonylaminomethyl, 4-(methoxycarbonyl)phenylcarbonylaminomethyl, 2-(pyrrol-1-yl)phenylcarbonylaminomethyl, 3-cyanophenylaminocarbonylaminomethyl, thien-2-ylcarbonylaminomethyl, phenylcarbonylaminomethyl, $(C_6H_5)CHCH_3NHCO(C_2H_4)CONHCH_2$, (4-methoxyphenyl)$COC_2H_4CONHCH_2$, 4-chlorophenylsulfonylaminocarbonylaminomethyl, 5-(acetyl)thien-2-ylcarbonylaminomethyl, pyridin-3-ylcarbonylaminomethyl, (3,4,5-trimethoxyphenyl)$C_2H_4CONHCH_2$, 3-methoxyphenylaminocarbonylaminomethyl, (phenoxy)$CH(CH_2CH_3)CONHCH_2$, 1-(ethoxycarbonyl)piperidin-4-yl-aminomethylcarbonylaminomethyl, 3-(benzyloxycarbonylamino)propyl, 2-[(diphenyl)methylaminocarbonyl]ethyl, 2-[2-(methyl)butylaminocarbonyl]ethyl, or 2-[$(C_6H_5)$CHCH$_3$NHCO]ethyl.

III. A third preferred group of compounds is that wherein:
   R is —CH(R²)Ar¹ wherein R² is hydrogen;
   Ar¹ is heteroaryl; and
   Ar² is a naphthyl ring of formula (b).
IV. A fourth preferred group of compounds is that wherein:
   R is —CH(R²)Ar¹ wherein R² is hydrogen;
   Ar¹ is aryl; and
   Ar² is a naphthyl ring of formula (b).
V. A fifth preferred group of compounds is that wherein:
   R is —CH(R²)CH═CHAr¹ wherein R² is hydrogen;
   Ar¹ is heteroaryl; and
   Ar² is a phenyl ring of formula (a) or a naphthyl ring of formula (b).
IV. A sixth preferred group of compounds is that wherein:
   R is —CH(R²)CH═CHAr¹ wherein R² is hydrogen;
   Ar¹ is aryl; and
   Ar² is a phenyl ring of formula (a) or a naphthyl ring of formula (b).
   Within the broadest definition of this invention set forth in the Summary of the Invention, certain compounds of Formula (I) wherein Z is —OH are preferred as intermediates in the synthesis of compounds wherein Z is —NHOH.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA), Calbiochem-Novabiochem (San Diego, Calif.) or Indofine Chemical Co. (Bellemead, N.J., USA) or are prepared by methods known to those skilled in the art following procedures set forth in references such as *Fieser and Fieser's Reagents for Organic Synthesis*, Volumes 1–15 (John Wiley and Sons, 1991); *Rodd's Chemistry of Carbon Compounds*, Volumes 1–5 and Supplementals (Elsevier Science Publishers, 1989), *Organic Reactions*, Volumes 1–40 (John Wiley and Sons, 1991), *March's Advanced Organic Chemistry*, (John Wiley and Sons, 4th Edition), and *Larock's Comprehensive Organic Transformations* (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (Ia) and (Ib)

Schemes A, B, and C describe alternative methods to generate the compounds of Formulae (Ia) and (Ib).

A compound of Formula (Ia) or (Ib) wherein R is —CH(R²)Ar¹, R¹, and Ar² are as defined in the Summary of the Invention is prepared from a suitably N-protected α-amino 1 as shown in Scheme A.

Scheme A

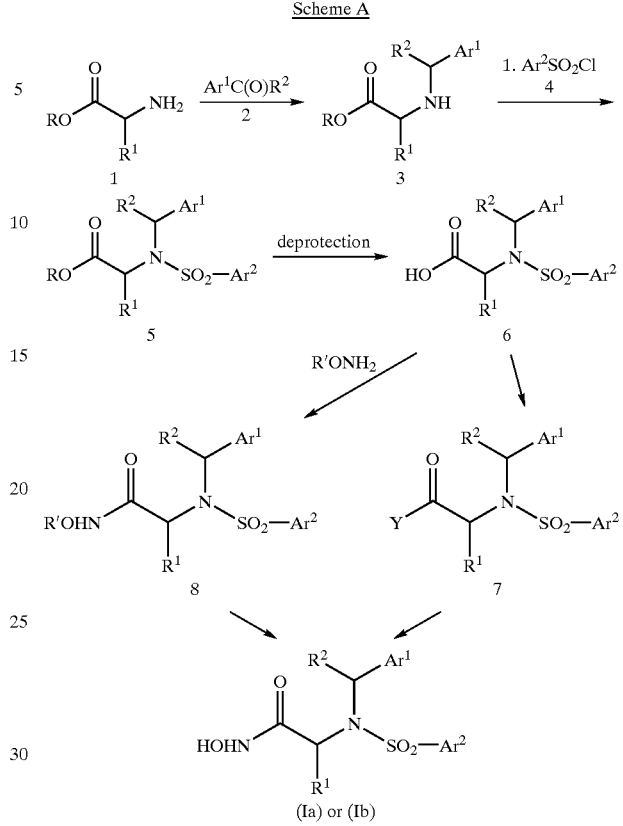

Treatment of an α-aminoacetate of formula 1 (where R is an alkyl such as methyl, ethyl, or tert-butyl or an aralkyl such as benzyl) with a compound of formula 2 where R² is hydrogen or alkyl under reductive amination reaction conditions i.e., in the presence of a suitable reducing agent (e.g., sodium cyanoborohydride, sodium triacetoxyborohydride, and the like) and an organic acid (e.g., glacial acetic acid, trifluoroacetic acid, and the like) provides an N-alkylated α-amino ester of formula 3. Suitable solvents for the reaction are halogenated hydrocarbons (e.g., 1,2-dichloroethane, chloroform, and the like).

Compounds of formula 1 are commercially available or they can be prepared by methods well known in the art. For example, esters of natural and unnatural amino acids such as D-valine benzyl ester p-tosylate salt, D-valine ethyl ester hydrochloride salt, D-valine tert-butyl ester hydrochloride salt, L-, D- or DL-serine methyl ester are commercially available. Alpha-thiomethyl amino acids can be prepared by following the procedures described in Arnold, L. D., Kalantar, T. H., Vederas, J. C. *J. Am. Chem. Soc.*, 107, 7108, (1985). Others can be prepared by esterification of N-protected α-amino acids (suitable amino-protecting group are tert-butoxycarbonyl, benzyloxycarbonyl, and the like), followed by deprotection of the amino group as described in Example 1.

Sulfonylation of 3 with an arylsulfonyl chloride of formula 4 provides a 2-(arylsulfonylamino)acetate of formula 5. The sulfonylation reaction can be carried out by methods well known in the art e.g., reacting 3 with a compound of formula 4 in the presence of trimethylsilylcyanide in acetonitrile. Compounds of formula 4 are commercially available or they can be prepared by methods well known in the art. For example, 4-methoxy-benzenesulfonyl chloride, 4-methoxy-2,3,6-trimethylbenzenesulfonyl chloride, 4-chloro-2,5-dimethylbenzenesulfonyl chloride, 2-dibenzofuransulfonyl chloride, 4-bromobenzenesulfonyl chloride, 2-naphthalenesulfonyl chloride, and 1-naphthalenesulfonyl chloride are commercially available. Others can be prepared by the procedures described in Bosshard, E. H. et. al., *Helv. Chim. Acta,* 42, 1653, (1959); Colter, A. K. and Turkos, R. E. C., *Canadian J. of Chem.,* 56, 585, (1978); Buchanan, G. W., et. al., *J. Org. Chem,* 40, 2357–2359 (1975) and Fujino, M, et. al., *Chem. Pharm. Bull.,* 10, 2825–2831 (1981). Typically, an unsulfonylated arene is treated with chlorosulfonic acid in dichloromethane at –5° C. to 10° C. to give the desired arenesulfonyl chloride.

Conversion of 5 to the corresponding carboxylic acid is dependent on the nature of the R group. For example, if R is a benzyl group then it is removed under hydrogenation reaction conditions. If R is an alkyl group such as methyl or ethyl group then it is removed under basic hydrolysis reaction conditions i.e., in the presence of an aqueous base (e.g., sodium hydroxide, lithium hydroxide, and the like) in an alcoholic organic solvent such as methanol, ethanol, and the like. If R is the tert-butyl group, then it is removed under acidic conditions.

Compound 6 can be converted to a compound of Formula (Ia) or (Ib) by converting 6 to an acyl derivative of formula 7 where Y is a leaving group under acylating conditions (e.g., chloro, succinimido, and the like). Treatment of 7 with N,O-bis-trimethylsilylhydroxylamine followed by acidic workup or upon the addition of methanol provides a compound of Formula (Ia) or (Ib) directly.

The acyl derivative 7 can be prepared by methods known to those of ordinary skill in the art. For example, compound 7 where Y is chloro can be prepared by reacting compound 5 with a chlorinating agent such as oxalyl chloride in a suitable organic solvent such as methylene chloride.

Alternatively, a compound of Formula (Ia) or (Ib) can be prepared from a compound of formula 6 via two steps by first reacting 6 with an O-substituted hydroxylamine (e.g., O-benzylhydroxylamine, O-tert-butylhydroxylamine, and the like) to give an O-protected hydroxamate of formula 8. The reaction is carried out in the presence of a coupling agent (e.g., N,N-dicyclohexylcarbodiimide, N-ethyl-N'-(3-dimethylamino-propyl)carbodiimide, and the like), an organic base (e.g., dimethylamino-pyridine, triethylamine, pyridine, N-methylmorpholine, and the like) and optionally hydroxybenzotriazole. Suitable solvents for the reaction are methylene chloride, dichloroethane, dimethylformamide, and the like. Removal of the O-protecting group then provides a compound of Formula (Ia) or (Ib). The reaction conditions utilized depend on the nature of the R' group e.g., if R' is tert-butyl, then the reaction is carried out in an inert solvent such as dichloromethane, in the presence of an acid (e.g., dry hydrogen chloride, trifluoroacetic acid, and the like). If R' is benzyl, then hydrogenolysis conditions utilizing a metal catalyst such as palladium in an inert solvent such as ethyl acetate or tetrahydrofuran are required. A compound of formula 5, 7, or 8 can also be converted to a compound of Formula (Ia) or (Ib) by the procedures described in PCT Application, Publication No. 98/32748.

A compound of Formula (Ia) or (Ib) where R is —CH(R²)Ar¹ and other groups are as defined in the Summary of the Invention can also be prepared from an α-amino acetate 1 as shown in Scheme B.

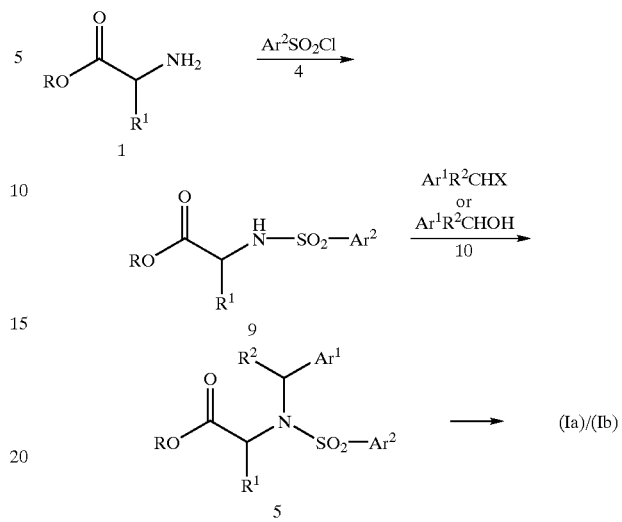

Sulfonylation of a compound of formula 1 with an arylsulfonyl chloride under the reaction conditions described in Scheme A above, provides 2-arylsulfonylacetate of formula 9 which is converted to a compound of formula 5 either:

(a) by reacting compound 9 where with an alkylating agent of formula Ar¹CHR²X (where X is a leaving group such as chloro, bromo, mesylate, triflate, and the like under alkylating conditions) in the presence of a base (e.g., sodium carbonate, potassium carbonate, cesium carbonate, and the like) and in a suitable solvents such as tetrahydrofuran, dioxane, N,N-dimethylformamide and the like; or (b) by reacting compound 9 with an alcohol of formula Ar¹CHR²OH in the presence of a trialkylphosphine or a triaryl phosphine, preferably tributylphosphine, triphenylphosphine, preferably tributylphosphine, and a dialkyl azodicarboxylate such as diethyl or diisopropyl azodicarboxylate or (1,1'-azodicarbonyl)dipiperidine, preferably (1,1'-azo-dicarbonyl)dipiperidine. Suitable solvents include aromatic hydrocarbons such as benzene, and the like.

Compound 5 is then converted to a compound of Formula (Ia) or (Ib) as described in Scheme A above.

A compound of Formula (Ia) or (Ib) where R is —CH(R²)Ar¹ and other groups are as defined in the Summary of the Invention can also be prepared from an α-aminoacid 11 as shown in Scheme C.

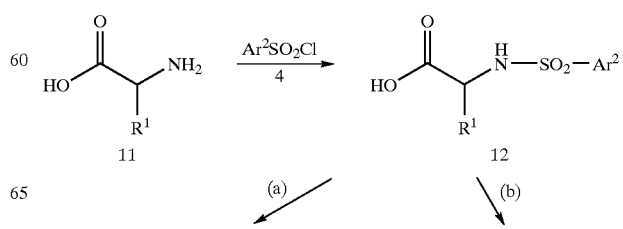

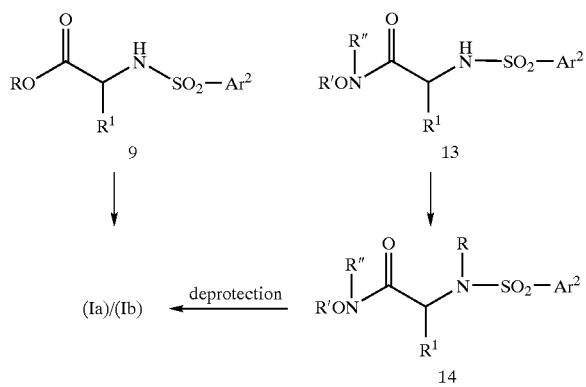

Sulfonylation of an α-amino acid 11 with an arylsulfonyl chloride of formula 4 in the presence of a base such as triethylamine provide 2-arylsulfonylamino acetic acid of formula 12. The reaction is carried out in an organic solvent and water mixture such as tetrahydrofuran and water. Compound 12 can be converted to a compound of Formula (Ia) or (Ib) by method (a) or (b).

In method (a), esterification of 12 provides a compound of formula 9 (where R is alkyl such as methyl, tert-butyl or aralkyl such as benzyl) which is then converted to a compound of Formula (Ia) or (Ib) by proceeding as described in Schemes A and B above.

In method (b), compound 12 is reacted with an N,O-protected hydroxylamine, such as O-(2,4-dimethoxybenzyl)-N-(2,4,6-trimethoxybenzyl)hydroxylamine, under the conditions described in Barlaam, B., et al., *Tet. Lett.*, Vol. 39, 7865, (1998) to give a compound of formula 13. Alkylation of 13 provides a compound of formula 14 which upon treatment with trifluoroacetic acid in methylene chloride in the presence of triethylsilane provides a compound of Formula (Ia) or (Ib) ((see., Barlaam, B., et al., *Tet. Lett.*, Vol.39, 7865, (1998)).

A compound of Formula (Ia) or (Ib) where R is —CH(R$^2$)CH=CHAr$^1$ and other groups are as defined in the Summary of the Invention can also be prepared from an α-amino acetate 1 as shown in Scheme D.

Scheme D

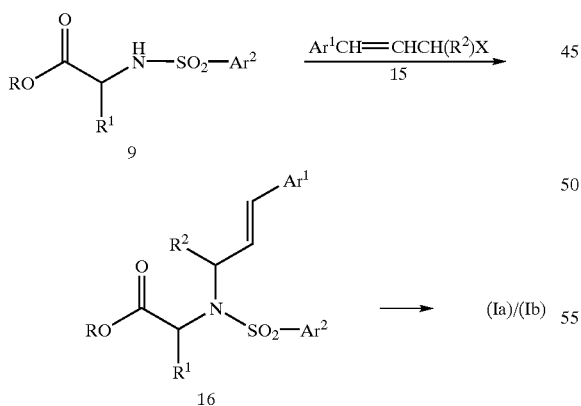

A compound of Formula (Ia) or (Ib) were R is —CH(R$^2$)CH=CHAr$^1$ is prepared by alkylating a compound of formula 9 (R cannot be benzyl) with an alkylating agent of formula 15 where X is a leaving group under alkylating conditions (e.g., chloro, bromo, mesylate, triflate, and the like) in the presence of a base (e.g., sodium carbonate, potassium carbonate, cesium carbonate, and the like) and in a suitable solvents such as tetrahydrofuran, dioxane, N,N-dimethylformamide and the like, to give a compound of formula 16. Hydrolysis of the ester group in 16 gives the corresponding acid which is then converted to a compound of Formula (Ia) or (Ib) by preparing the acid chloride derivative followed by treatment with N,O-bis-trimethylsilylhydroxylamine as described in Scheme A above.

A compound of formula 15 such as cinnamyl chloride is commercially available.

A compound of Formula (Ia) or (Ib) wherein Ar$^2$ is as defined in the Summary of the Invention, R is CH$_2$Ar$^1$ (wherein Ar$^1$ is 3,4-methylenedioxyphenyl), and R$^1$ is —CH$_2$NHCOOR" (wherein R" is hydrogen, alkyl, haloalkyl, cycloalkyl, cycloalkylalkyl, aryl, aralkyl, heteroaryl, heteroaralkyl, or heterocyclylalkyl) can be prepared from N-protected diaminopropionic acid 2, as shown in Scheme E and as described more fully in Example 16.

Scheme E

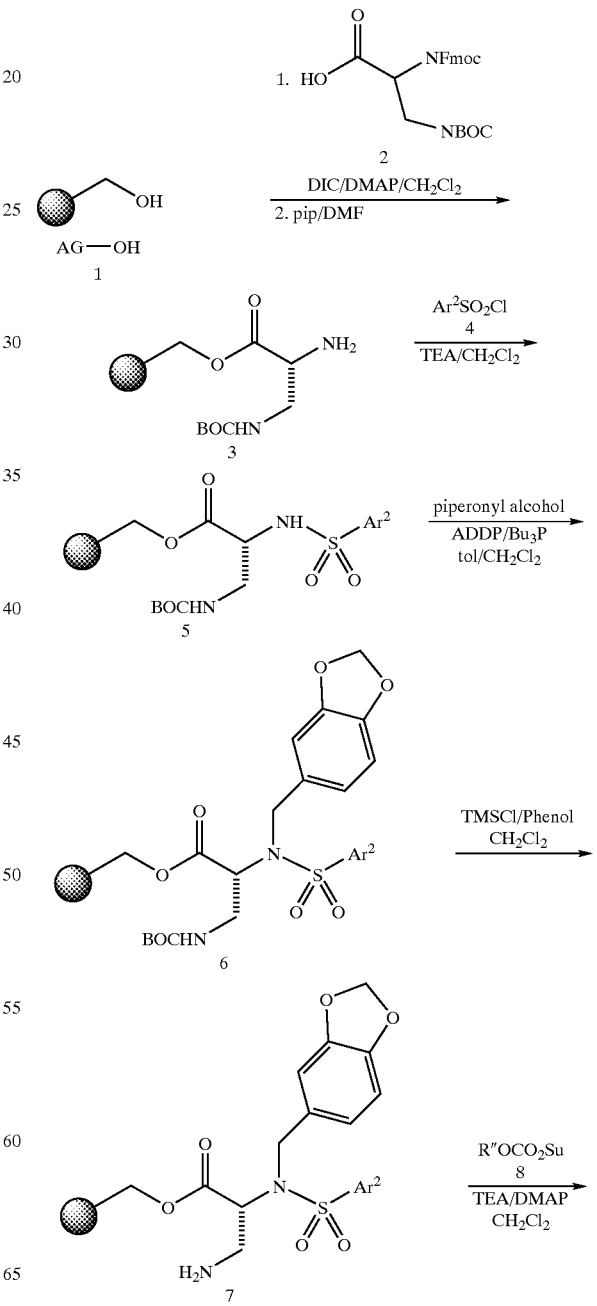

-continued

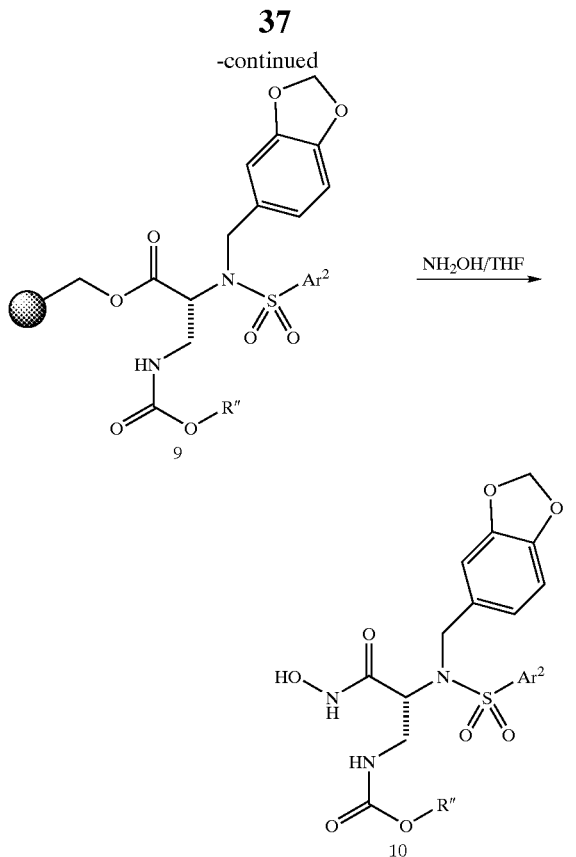

A compound of Formula (Ia) or (Ib) wherein $Ar^2$ is as defined in the Summary of the Invention, R is $CH_2Ar^1$ (wherein $Ar^1$ is 3,4-methylenedioxyphenyl), and $R^1$ is —$CH_2NHCONHAr$ can be prepared from the resin of formula 7 (of Scheme E) as shown in Scheme F and as described more fully in Example 17.

Scheme F

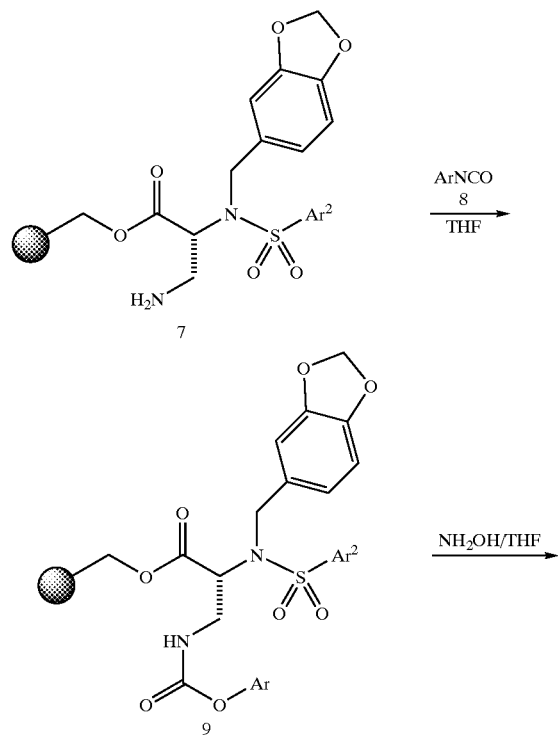

-continued

Utility, Testing, and Administration

Utility

Compounds of this invention are useful in the treatment of diseases associated with excessive deposition of interstitial collagens, exemplified by interstitial pulmonary fibrosis, pericentral fibrosis, Symmers' fibrosis, perimuscular fibrosis, kidney and liver fibrosis, idiopathic pulmonary fibrosis, endocardial sclerosis, hepatitis, acute respiratory distress syndrome, arthritis, cystic fibrosis, tendon surgery, surgical adhesions, corneal scarring, and restenosis.

Compounds of this invention are inhibitors of procollagen C-proteinase. Therefore, they inhibit C-terminal processing of types I, II, and III collagens necessary for their ability to form insoluble collagen fibrils. Furthermore, selected compounds of the invention selectively inhibit procollagen C-proteinase over other collagen degradating enzymes such as collagenase-1, collagenase-2, and collagenase-3. Therefore, the natural resorption of collagen mediated by collagenase-1, collagenase-2 and collagenase-3 is largely unaffected resulting in compounds of greater therapeutic efficacy. In particular, preferred compounds of this invention inhibit procollagen C-proteinase with greater than 100 fold selectivity over collagenase-1, collagenase-2, and collagenase-3. Selective inhibition of procollagen C-proteinase over collagenase-1, collagenase-2, and collagenase-3 was demonstrated by the assays described in the Examples. Thereby, this invention allows the treatment of fibrotic diseases by administering to a patient an agent that selectively inhibits procollagen C-proteinase over collagenase-1 collagenase-2, and collagenase-3.

Testing

The ability of the compounds of Formulae (Ia) and (Ib) to inhibit procollagen C-proteinase activity, may be demonstrated by a variety of in vitro assays known to those of ordinary skill in the art, such as the assay described in Example 21. The selectivity against collagenase enzymes may be determined by the assay described in Example 22.

The in vivo efficacy of compounds of Formulae (Ia) and (Ib) against fibrotic disease and the deposition of collagen may be shown by numerous animal models including the mouse bleomycin induced pulmonary fibrosis model ((Phan, S. H., et.al. "Bleomycin-induced Pulmonary Fibrosis," *Am. Rev. Respir. Dis.,* 124:428–434 (1981) and Piguet, P. F., et al. "Effective Treatment of the Pulmonary Fibrosis Elicited in Mice by Bleomycin or Silica with anti-CD-11 Antibodies," *Am. Rev. Resp. Dis.,* 147:435–441 (1993)), the sponge implant model ((Unemori, E. N., et al. "Human Relaxin Decreases Collagen Accumulation In Vivo in Two Rodent Models of Fibrosis," *J. Invest. Dermatol.,* 101:280–285 (1993)), the carbon tetrachloride or NDMU induced renal fibrosis model, as well as other animal models cited in WO 97/05865 ("C-Proteinase Inhibitors for the Treatment of Disorders Relating to the Overproduction of Collagen"), published Feb. 20, 1997.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula (Ia) or (Ib) may range from approximately 0.05–50 mg per kilogram body weight of the recipient per day; preferably about 0.3–20 mg/kg/day. Thus, for administration to a 70 kg person, the dosage range would most preferably be about 21 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is systemic using a convenient daily dosage regimen which can be adjusted according to the degree of affliction.

Intranasal delivery is typically accomplished with dry powder formulations, liquid solutions or suspensions suitable for nebulization or with aerosol propellants suitable for use in a metered dose inhaler. Alternatively, drug substance may be associated with microspheres made of materials such as gelatin, dextran, collagen or albumin The microspheres are conveniently delivered in freeze dried form with a nasal insufflator device or a pressurized aerosol cannister. Penetration enhancers such as amphiphilic steroids may also be used as additives to increase the systemic absorption of the drug into the tissue.

Effective administration may also be accomplished by pulmonary or respiratory delivery since polypeptides are readily absorbed through the cellular lining of the alveolar region of the mammalian lung. Advantageously, such administration frequently does not require the use of penetration enhancers as additives. Devices and methods for pulmonary delivery deep into the lung are described in U.S. Pat. No. 5,780,014, issued Jul. 14, 1998 and U.S. Pat. No. 5,814,607, issued Sep. 29, 1998.

Lastly, compounds may be systemically administered by transdermal delivery, which typically involves placing the drug on the surface of the skin and allowing it to permeate through the skin. Transdermal delivery devices employ a structure such as an adhesive patch or the like that serves as a reservoir for the drug and brings the drug into diffusive contact with the skin. In one general typ, the structure is a three dimensionally stable matrix known as a monolithic matrix. Such matrices are described in more detail in U.S. Pat. Nos. 5,804,214, 5,149,538 and 4,956,171 which describe matrices made of polymers and copolymers of acrylic latexes, acrylic esters, methacrylic esters and vinyl acetates.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (Ia) or (Ib) in combination with at least one pharmaceutically acceptable excipient. Acceptable excipients are non-toxic, aid administration, and do not adversely affect the therapeutic benefit of the compound of Formula (Ia) or (Ib). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of formula I based on the total formulation, with the balance being one or more suitable pharmaceutical excipients. Preferably, the compound is present at a level of about 1–80 wt %. Representative pharmaceutical formulations containing a compound of Formula (Ia) or (Ib) are described in Example 18.

EXAMPLES

The following preparations and examples are given to enable those skilled in the art to more clearly understand and to practice the present invention. They should not be considered as limiting the scope of the invention, but merely as being illustrative and representative thereof.

Example 1

N-hydroxy-2(R)-[(3,4-methylenedioxybenzyl)-(4-methoxy-2,3,6-trimethylbenzene-sulfonyl)amino]-3-methylbutyramide (Table I, Cmpd 12)

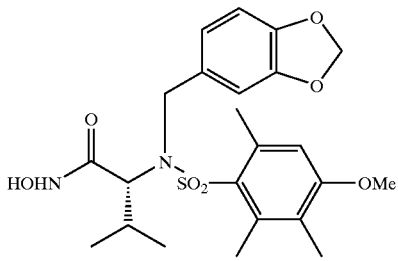

Step 1

N-Tert-butoxycarbonyl-D-valine (70 g, 0.32 mol) and cesium carbonate (200.2 g, 0.615 mol) were stirred in dry dimethylformamide (550 mL). Benzyl bromide (40.32 mL, 0.336 mol) was added and the reaction mixture was stirred overnight. The material was concentrated on the rotoevaporator and the residue was dissolved in methylene chloride (200 mL) and the methylene chloride layer was washed with water and brine, dried over magnesium sulfate and concentrated to give N-tert-butoxycarbonyl-D-valine benzyl ester (97 g) as a viscous oil.

Step 2

N-Tert-butoxycarbonyl-D-valine benzyl ester (70.7 g, 0.23 mol) was dissolved in a mixture of trifluoroacetic acid and methylene chloride (150 mL in 1:4 ratio) and the reaction mixture was heated at 50–60° C. After 6 h, the reaction mixture was concentrated to give D-valine benzyl ester trifluoroacetic acid salt (156.8 g) as a viscous oil which was converted to the free amine just prior to use.

Step 3

1 N Sodium hydroxide (80 mL) was added to a solution of D-valine benzyl ester trifluoroacetic acid salt (10 g, 31.1 mmol) in methylene chloride (80 mL) and the reaction mixture was stirred until all the starting material was converted to the free amine. The organic phase was collected and washed with brine, dried over magnesium sulfate, and concentrated to give D-valine benzyl ester (5.35 g) as a clear oil.

Step 4

To a solution of D-valine benzyl ester (4 g, 19.3 mmol) and trimethylsilylcyanide (7.2 mL, 57.9 mmol) in acetonitrile (40 mL) was added 4-methoxy-2,3,6-trimethylbenzenesulfonyl chloride (4.8 g, 19.3 mmol). After 3 h, the reaction mixture was diluted with ethyl acetate (100 mL) and transferred to a separatory funnel. Aqueous hydrochloric acid (120 mL, 2.5%) was added and the organic layer was separated and washed with 5% sodium bicarbonate and brine and then dried over magnesium sulfate. The organics were removed in vacuo to give 2(R)-(4-methoxy-2,3,6-trimethylbenzenesulfonylamino)-3-methylbutyric acid benzyl ester (8 g) as a brown oil.

Step 5

To a mixture of 2(R)-(4-methoxy-2,3,6-trimethylbenzenesulfonylamino)-3-methylbutyric acid benzyl ester (4.5 g, 10.72 mmol), 3,4-(methylenedioxy)phenylmethanol (2.04 g, 13.41 mmol), and tributylphosphine (3.35 mL, 13.4 mmol) in dry benzene (60 mL) cooled in an ice bath was added 1,1'-(azodicarbonyl)dipiperidine (3.38 g, 13.4 mmol). The reaction mixture was stirred overnight to room temperature and then flash chromatographed on a silica gel column (5–10% ethyl acetate/hexanes) to give 2(R)-[(3,4-methylenedioxy-benzyl)-(4-methoxy-2,3,6-trimethylbenzenesulfonyl)amino]-3-methylbutyric acid benzyl ester (4.8 g) as a white solid.

Step 6

To a solution of 2(R)-[(3,4-methylenedioxybenzyl)-(4-methoxy-2,3,6-trimethylbenzenesulfonyl)amino]-3-methylbutyric acid benzyl ester (4.7 g, 8.49 mmol) in a 4:1 mixture of ethanol/tetrahydrofuran (40 mL) was added 10% Pd/C (0.15 g). The reaction mixture was placed under a hydrogen balloon. After 3 h, the reaction mixture was filtered through Celite and the Celite cake was washed with ethanol. The filtrate was concentrated to give of 2(R)-[(3,4-methylenedioxybenzyl)-(4-methoxy-2,3,6-trimethylbenzenesulfonyl)amino]-3-methylbutyric acid (3.9 g) as a white foam.

Step 7

To a solution of 2(R)-[(3,4-methylenedioxybenzyl)-(4-methoxy-2,3,6-trimethyl-benzenesulfonyl)amino]-3-methylbutyric acid (3.82 g, 8.24 mmol) in dry methylene chloride (20 mL) was added oxalyl chloride (2.2 mL, 24.72 mmol) and a drop of dimethylformamide. The reaction mixture was stirred for 4 h and then concentrated. The residue was dissolved in methylene chloride (20 mL) and N,O-bis-trimethylsilylhydroxylamine (8.8 mL, 41.2 mmol) was added. After 4 h, methanol (1 mL) was added and the stirring was continued for 30 min. Silica gel (10 g) was added and the material was concentrated to dryness. The resultant powder was flash chromatographed on a silica gel column and eluted with 50% ethyl acetate/hexanes to give N-hydroxy-2(R)-[(3,4-methylenedioxybenzyl)-(4-methoxy-2,3,6-trimethylbenzenesulfonyl)amino]-3-methylbutyramide (2.46 g).

Example 2

N-Hydroxy-2(R)-[(4-methoxycarbonylbenzyl)-(4-methoxybenzenesulfonyl)amino]-3-methylbutyramide (Table I, Cmpd 21)

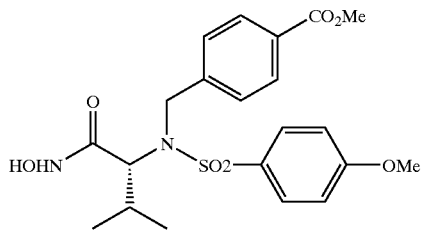

Step 1

To an ice-cooled solution of D-valine (50.5 g, 0.43 mol) and triethylamine (145 mL, 1.034 mol) in a 1:1 mixture of tetrahydrofuran and water (350 mL) was added 4-methoxybenzenesulfonyl chloride (88.2 g, 0.43 mmol). The reaction mixture was stirred and allowed to warm to room temperature overnight. The volatile organics were removed and the aqueous phase was extracted with diethyl ether. The aqueous phase was acidified to pH 3 with 10% hydrochloric acid and the product was extracted into ethyl acetate. The ethyl acetate layer was washed with brine, dried over magnesium sulfate, and then concentrated to give 2(R)-(4-methoxy-benzenesulfonylamino)-3-methylbutyric acid as a white solid (90.45 g).

Step 2

To a solution of 2(R)-(4-methoxybenzenesulfonylamino)-3-methylbutyric acid (40 g, 139.2 mmol) and cesium carbonate (85.7 g, 444 mmol) in dimethylformamide was added benzyl bromide (16.1 g, 135 mmol). The reaction mixture was stirred overnight. The dimethylformamide was removed on the rotoevaporator and the residue was dissolved in ethyl acetate (200 ml) and partitioned with an equal volume of water. The organic phase was collected and washed with an equal volume of brine. The aqueous phases were back extracted with ethyl acetate (2×150 ml), combined and dried over magnesium sulfate and condensed to provide 2(R)-(4-methoxybenzenesulfonylamino)-3-methylbutyric acid benzyl ester (42.6 g) as a white crystalline solid.
Step 3

To a solution of 2(R)-(4-methoxybenzenesulfonylamino)-3-methylbutyric acid benzyl ester (1 g, 2.65 mmol) and 4-carboxymethylbenzyl bromide (0.577 g, 2.52 mmol) in dry dimethylformamide (60 mL) was added potassium carbonate (0.55 g, 4 mmol). The reaction mixture was stirred overnight and then condensed on the rotoevaporator. Purification by flash chromatography on a silica gel column using (5%) ethyl acetate/hexanes as the eluant gave 2(R)-[(4-methoxycarbonylbenzyl)-(4-methoxybenzenesulfonyl)amino]-3-methylbutyric acid benzyl ester (0.965 g) which was converted to N-hydroxy-2(R)-[(4-methoxycarbonylbenzyl)-(4-methoxybenzene-sulfonyl)amino]-3-methylbutyramide by following Steps 6 and 7 in Example 1, above.

Example 3

N-Hydroxy-2(R)-[(1H-indol-5-ylmethyl)-(4-methoxybenzenesulfonyl)amino]-3-methylbutyramide (Table I, Cmpd 3)

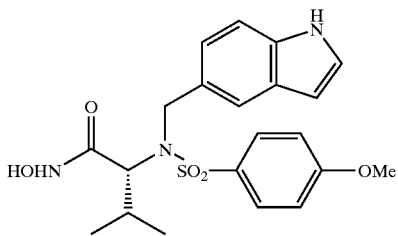

Step 1

To a solution of 5-indole carboxylic acid (5.08 g, 31.5 mmol) in a 1:1 mixture of methanol/methylene chloride (40 mL) was added (trimethylsilyl)diazomethane (33 mL, 2 M solution in hexanes) in portions over 15 min. The yellow colored solution was concentrated on the rotoevaporator to provide methyl-5-indole carboxylate as a white powder (5.5 g).
Step 2

To a solution of methyl-5-indole carboxylate (4.9 g, 27.97 mmol) in dry acetonitrile (45 mL) was added di-tert-butyl dicarbonate (6.41 g, 29.36 mmol) followed by 4-dimethylamino-pyridine (142 mg, 1.43 mmol). The reaction mixture was stirred for 3 h and then loaded onto a flash silica gel column and eluted with ethyl acetate/hexane (5%) to give methyl (N-tert-butoxycarbonyl)indole-5-carboxylate as a clear viscous oil (7.69 g).
Step 3

To a cooled solution (−78° C.) of methyl(N-tert-butoxycarbonyl)indole-5-carboxylate (7.6 g, 27.9 mmol) in dry tetrahydrofuran (75 mL) was added diisobutylaluminum hydride (57 mL, 1.5 M in toluene) via syringe over 5 min. After 1.5 h, the reaction mixture was quenched by careful addition of methanol (15 mL) and allowed to warm to room temperature over 45 min. Water (20 mL) and a saturated solution of ammonium chloride(10 mL) was added with vigorous stirring and the resultant inorganic precipitate was removed by filtration. The filtrate was condensed on the roto-evaporator and the residue was partitioned between a 1:1 mixture of ethyl acetate/water (160 mL). The ethyl acetate phase was washed with brine and the aqueous phases back extracted with ethyl acetate. The organic phase was combined, dried with magnesium sulfate, filtered and concentrated to provide (N-tert-butoxycarbonyl)indole-5-methanol (7.35 g) as a semi-viscous yellow oil which was used in the next step without further purification.
Step 4

To an ice-cooled mixture of 2(R)-(4-methoxybenzenesulfonylamino)-3-methylbutyric acid benzyl ester (5 g, 13.25 mmol) [prepared as described in Example 2 above], N-tert-butoxycarbonyl-5-indole methanol (3.8 g, 14.6 mmol) and tributylphosphine (3.6 mL, 14.6 mmol) in dry benzene (60 mL) was added [1,1'-azodicarbonyl]dipiperidine (3.68 g, 14.6 mmol). The reaction mixture was stirred overnight at room temperature and then chromatographed on a silica gel column eluting with (5–10%) ethyl acetate/hexanes to give of 2(R)-[(N-tert-butoxy-carbonylindol-5-ylmethyl)-(4-methoxybenzenesulfonyl)amino]-3-methylbutyric acid benzyl ester (6.5 g) as a white foamy semi-solid.
Step 5

A solution of 2(R)-[(N-tert-butoxycarbonylindol-5-ylmethyl)-(4-methoxybenzene-sulfonyl)amino]-3-methylbutyric acid benzyl ester (2.7 g. 4.45 mmol) and trifluoroacetic acid (5 mL) in methylene chloride (15 mL) was stirred for 2 h at room temperature. The organics were removed under vacuum and the residue was dissolved in ethyl acetate (80 mL) and the ethyl acetate layer was washed with 5% sodium bicarbonate and brine. The organic layer was dried over magnesium sulfate and concentrated to give a white foamy solid which was chromatographed on a silica gel column eluting with (5–100%) ethyl acetate/hexanes. This procedure gave 2(R)-[(1H-indol-5-yl-methyl)-(4-methoxybenzenesulfonyl)amino]-3-methylbutyric acid benzyl ester (1.7 g) as a white foamy semi-solid, which was converted to 2(R)-[(1H-indol-5-ylmethyl)-(4-methoxybenzenesulfonyl)amino]-3-methylbutyric acid by following the procedure described in Example 1, Step 6 above.
Step 6

To an ice-cooled solution of 2(R)-[(1H-indol-5-ylmethyl)-(4-methoxybenzene-sulfonyl)amino]-3-methylbutyric acid (0.32 g, 0.77 mmol), O-benzylhydroxyl amine (0.35 mL, 2.3 mmol), 1-hydroxybenzotriazole hydrate (0.118 g, 0.77 mmol), and N-methyl-morpholine (0.12 mL, 1.1 mmol) in anhydrous dimethylformamide was added 1-(3-dimethylaminopropyl)-3-ethyl carbodiimide hydrochloride salt (0.221 g, 1.2 mmol). The reaction mixture was stirred overnight and then concentrated. The residue was dissolved in ethyl acetate (80 mL) and washed with 1.5% hydrochloric acid, 5% sodium bicarbonate, and brine. Crystallization from hot CH$_2$Cl$_2$-hexanes of the residue followed by purification of the mother liquor by preparatory thin layer chromatography using 5% methanol/methylene chloride as the eluant gave 2(R)-N-benzyloxy-[(1H-indol-5-ylmethyl)-(4-methoxybenzenesulfonyl)amino]-3-methylbutyramide (0.31 g) as a tan crystalline powder.
Step 7

To a solution of 2(R)-N-benzyloxy-[(1H-indol-5-ylmethyl)-(4-methoxybenzene-sulfonyl)amino]-3-methylbutyramide (0.34 g, 0.58 mmol) in 1:1 mixture of ethanol/tetrahydrofuran (15 mL) was added 10% Pd/C (0.075 g). The reaction mixture was placed under hydrogen balloon. After 2.5 h, the reaction mixture was filtered through a pad of Celite (3.0 g) and the Celite pad was washed with ethanol (200 mL). The filtrate was concentrated to give a tan semi-solid. Purification with preparative thin layer chromatography (7% methanol/methylene chloride) gave N-hydroxy-2(R)-[(1H-indol-5-ylmethyl)-(4-methoxybenzenesulfonyl)amino]-3-methylbutyramide (200 mg) as a tan solid.

Example 4

N-Hydroxy-2(R)-[(3-nitro-4-methylbenzyl)-(4-methoxybenzenesulfonyl)amino]-3-methylbutyramide (Table I, Cmpd 23)

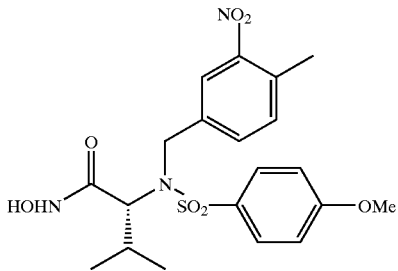

Step 1

To an ice-cooled solution of 2(R)-(4-methoxybenzenesulfonylamino)-3-methylbutyric acid (30 g, 104.4 mmol), [prepared as described in Example 2, step 1 above], in methylene chloride was added N,N'-diisopropyl-O-tert-butylisourea [can be prepared by the procedure described in Lon J. Mathias, Synthesis, 561–576, (1979)] (75 mL, 3.5 M solution) via additional funnel over 45 min. The reaction mixture was maintained at 0° C. for 2 h, and then allowed to warm to room temperature overnight. Purification by flash chromatography on a silica gel column using (10–20%) ethyl acetate/hexanes as the eluant gave of 2(R)-(4-methoxybenzenesulfonylamino)-3-methylbutyric acid tert-butyl ester (18 g) as a white crystalline solid.

Step 2

To a solution of 2(R)-(4-methoxybenzenesulfonylamino)-3-methylbutyric acid tert-butyl ester (0.15 g, 0.44 mmol) and potassium carbonate (0.32 g, 2.32 mmol) in dry dimethylformamide (15 mL) was added 3-nitro-4-methylbenzyl chloride (81.1 mg. 0.44 mmol). The reaction mixture was stirred overnight and then concentrated on the rotoevaporator. The residue was dissolved in a 1:1 ethyl acetate and brine (50 mL). The organic phase was isolated, dried over magnesium sulfate, and concentrated to give 2(R)-[(3-nitro-4-methylbenzyl)-(4-methoxybenzenesulfonyl)amino]-3-methylbutyric acid tert-butyl ester (0.196 g) as a yellow viscous oil which was converted to 2(R)-[(3-nitro-4-methylbenzyl)-(4-methoxy-benzenesulfonyl)amino]-3-methylbutyric acid by following the procedure described in Example 10, Step 8 below. 2(R)-[(3-nitro-4-methylbenzyl)-(4-methoxybenzenesulfonyl)-amino]-3-methylbutyric acid is then converted to N-hydroxy-2(R)-[(3-nitro-4-methylbenzyl)-(4-methoxybenzenesulfonyl)amino]-3-methylbutyramide by following Example 1, Steps 6 and 7 above.

Example 5

N-hydroxy-2(R)-[(3,4-methylenedioxybenzyl)-(4-methoxy-2,3,6-trimethylbenzenesulfonyl)amino]-3-hydroxypropionamide (Table I, Cmpd 5)

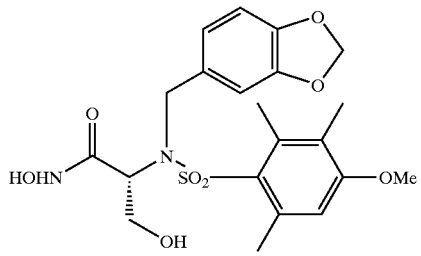

Step 1

To a suspension of D-serine (6.95 g, 66.1 mmol) in acetonitrile (100 mL) was added trimethylsilyl cyanide (40 mL, 298 mmol) and the resulting solution was heated to 80° C. After 1 h, 4-methoxy-2,3,6-trimethylbenzenesulfonyl chloride (17.3 g, 69.4 mmol) was added and the heating was continued. After 12 h, the reaction mixture was cooled to room temperature. Methanol (15 mL) was added, and the organics were removed in vacuo. The residue was diluted with diethyl ether (300 mL) and after cooling the reaction mixture to 0° C., the pH was adjusted to 8 with 6 N aqueous sodium hydroxide solution. The organic layer was collected and the aqueous layer was extracted with diethyl ether. The aqueous layer was adjusted to pH 4 and again extracted with ethyl acetate. The combined organic extracts were dried over magnesium sulfate and concentrated to afford 2(R)-(4-methoxy-2,3,6-trimethylbenzene-sulfonylamino)-3-hydroxypropionic acid (20.5 g) as a brown foam which was used without further purification.

Step 2

To a solution of 2(R)-(4-methoxy-2,3,6-trimethylbenzenesulfonylamino)-3-hydroxypropionic acid (27.9 g, 87.9 mmol) in dimethylformamide (280 mL) at 0° C., was added potassium carbonate (72.9 g, 527 mmol) and a solution of 3,4-methylenedioxybenzyl chloride ((60 g, 170.8 mmol, 50% (w/w)) in methylene chloride. After 2 h, lithium iodide (5.88 g, 44 mmol) was added and the reaction mixture was warmed to rt. over 2 h. After 6 h, the reaction mixture was partitioned between ethyl acetate (600 mL) and water (250 mL). The organic layer was separated, dried over magnesium sulfate and concentrated in vacuo. The crude residue was chromatographed (300 g SiO$_2$, 15% ethyl acetate-hexanes) to afford 2(R)-(4-methoxy-2,3,6-trimethylbenzenesulfonylamino)-3-hydroxypropionic acid 3,4-methylenedioxybenzyl ester (38.4 g) which was taken directly into the next reaction without further purification.

Step 3

2(R)-(4-methoxy-2,3,6-trimethylbenzenesulfonylamino)-3-hydroxypropionic acid 3,4-methylenedioxybenzyl ester (38.4 g) was dissolved in methylene chloride (140 mL) and dihydropyran (23 mL). The reaction mixture was cooled to 0° C. and p-toluenesulfonic acid monohydrate (0.78 g) was added. After 1 h, the reaction mixture was poured into saturated aqueous sodium bicarbonate (200 mL). The organic layer was separated, dried over magnesium sulfate, and concentrated in vacuo. This residue was chromatographed (300 g SiO$_2$, 15% ethyl acetate-hexanes) to afford 2(R)-(4-methoxy-2,6-dimethylbenzenesulfonyl-amino)-3-(tetrahydropyran-2-yloxy)propionic acid 3,4-methylenedioxybenzyl ester (41.4 g).

Step 4

To a solution of 2(R)-(4-methoxy-2,6-dimethylbenzenesulfonyl-amino)-3-(tetrahydropyran-2-yloxy)propionic acid 3,4-methylenedioxybenzyl ester (9.0 g, 16.8 mmol) in benzene (150 mL) at 0° C. was added 3,4-methylenedioxyphenyl methanol (3.8 g, 25.2 mmol), tri-n-butylphosphine (5.1 g, 25.2 mmol), followed by 1,1'-[azodicarbonyl]dipiperidine (6.35 g, 25.2 mmol). The reaction mixture was allowed to warm to room temperature over 4 h. After 16 h, the reaction mixture was diluted with an equal volume of hexanes, cooled to 0° C. for 2 h and filtered. The residue was chromatographed (300 g SiO$_2$, 15% ethyl acetate-hexanes) to afford 2(R)-[(3,4-methylenedioxybenzyl)-(4-methoxy-2,6-dimethylbenzenesulfonyl)amino]-3-(tetrahydropyran-2-yloxy)propionic acid 3,4-methylenedioxybenzyl ester (10.0 g) as a pale orange oil.

Step 5

To a solution of 2(R)-[(3,4-methylenedioxybenzyl)-(4-methoxy-2,6-dimethylbenzene-sulfonyl)amino]-3-(tetrahydropyran-2-yloxy)propionic acid 3,4-methylenedioxybenzyl ester (3.26 g, 4.57 mmol) in argon deoxygenated 80% ethanol-tetrahydrofuran (100 mL) was added 10% Pd—C (2 g) and the resulting reaction mixture was hydrogenated at atmospheric pressure for 45 min. The reaction mixture was degassed under argon, the slurry was filtered over Celite, and the Celite pad was washed with ample 80% ethanol-methylene chloride. The filtrate was concentrated and azeotroped with tetrahydrofuran (200 mL) and the residue was dissolved in dimethylformamide (25 mL). O-Benzyl hydroxylamine (1.78 g, 14.5 mmol), HOBT (0.71 g, 5.2 mmol), and EDAC (2.75 g) were added and the reaction mixture was stirred for 16 h. The reaction mixture was diluted with ethyl acetate and was washed with 2.4 N aqueous hydrochloric acid and saturated aqueous sodium bicarbonate. The mixture was then dried over magnesium sulfate and concentrated in vacuo to afford crude N-benzyloxy-2(R)-[(3,4-methylenedioxy-benzyl)-(4-methoxy-2,6-dimethylbenzenesulfonyl)amino]-3-(tetrahydropyran-2-yloxy)-propionamide (2.8 g,) which was taken directly into the next reaction without further purification.

Step 6

To a solution of N-benzyloxy-2(R)-[(3,4-methylenedioxybenzyl)-(4-methoxy-2,6-dimethylbenzenesulfonyl)amino]-3-(tetrahydropyran-2-yloxy)propionamide (1.7 g, 4.3 mmol) in methanol (100 mL) at 0° C. was added p-toluenesulfonic acid monohydrate (150 mg). After 12 h, the reaction mixture was warmed to room temperature and stirred for an additional 5 h. The reaction mixture was concentrated and the residue was chromatographed (Biotage 40M; 20% to 50% ethyl acetate-hexanes) to afford N-benzyloxy-2(R)-[(3,4-methylenedioxybenzyl)-(4-methoxy-2,6-dimethylbenzenesulfonyl)amino]-3-hydroxypropionamide (1.60 g).

Step 7

To a solution of N-benzyloxy-2(R)-[(3,4-methylenedioxybenzyl)-(4-methoxy-2,6-dimethylbenzenesulfonyl)amino]-3-hydroxypropionamide (3.0 g, 5.39 mmol) in argon deoxygenated 80% ethanol-tetrahydrofuran (160 mL) was added 10% Pd—C (1.3 g), and the resulting mixture was hydrogenated at atmospheric pressure for 45 min. The reaction mixture was degassed under argon and the slurry was filtered over Celite. The Celite cake was washed with ample 80% ethanol-methylene chloride and the filtrate was concentrated to almost dryness forcing the mixture to crystallize. The slurry was filtered, washing with 50% diethyl ether-hexanes to afford N-hydroxy-2(R)-[(3,4-methylenedioxybenzyl)-(4-methoxy-2,6-dimethylbenzenesulfonyl)amino]-3-hydroxypropionamide (2.38 g) as a white solid.

Example 6

N-hydroxy-3-acetoxy-2(R)-[(3,4-methylenedioxybenzyl)-(4-methoxy-2,3,6-trimethylbenzenesulfonyl)amino]propionamide
(Table I, Cmpd 14)

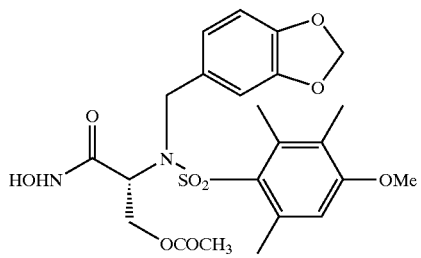

Step 1

To a solution of N-benzyloxy-2(R)-[(3,4-methylenedioxybenzyl)-(4-methoxy-2,6-dimethylbenzenesulfonyl)amino]-3-hydroxypropionamide (450 mg, 0.82 mmol) in pyridine (2 mL) at 0° C. was added acetic anhydride (0.09 mL, 0.98 mmol). The reaction mixture was allowed to warm to room temperature over 12 h and then partitioned between 2 N aqueous hydrochloric acid and methylene chloride (100 mL). The methylene chloride layer was separated, dried over magnesium sulfate, and concentrated. Purification of the residue by preparative TLC (30% ethyl acetate-hexanes) gave N-benzyloxy-2(R)-[(3,4-methylenedioxy-benzyl)-(4-methoxy-2,6-dimethylbenzenesulfonyl)amino]-3-acetoxypropionamide.

Step 2

To a solution of N-benzyloxy-2(R)-[(3,4-methylenedioxybenzyl)-(4-methoxy-2,6-dimethylbenzenesulfonyl)amino]-3-acetoxypropionamide dissolved in argon deoxygenated 80% ethanol-tetrahydrofuran (15 mL) was added 10% Pd—C (100 mg) and the resulting mixture was hydrogenated at atmospheric pressure for 45 min. The reaction mixture was degassed under argon and the slurry was filtered over Celite. The Celite cake was washed with ample 80% ethanol-methylene chloride and the filtrate was concentrated. The crude mixture was dissolved in ethyl acetate (1–2 mL) and added slowly to rapidly stirring hexanes (100 mL) to produce a precipitate. The precipitate was filtered and dried (50 °C.; 1 torr) to afford N-hydroxy-2(R)-[(3,4-methylenedioxybenzyl)-(4-methoxy-2,6-dimethylbenzenesulfonyl)amino]-3-acetoxypropionamide (171.3 mg) as a white powder.

Example 7

N-Hydroxy-2(R)-[(4-methoxy-2,5,6-trimethylbenzenesulfonyl)-(1H-indol-5-ylmethyl)amino]-3-tert-butoxypropionamide (Table I, Cmpd 15)

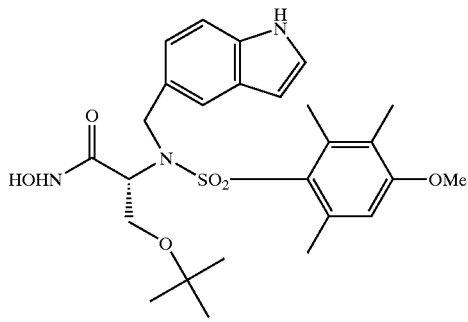

Step 1

To a solution of 1H-indole-5-carboxylic acid (5 g, 31.0 mmol) in 70% methanol/methylene chloride (105 mL) at 0° C. was added 1M trimethylsilyldiazomethane in hexanes (46 mL, 46 mmol). After 45 min., the reaction mixture was concentrated to afford 1H-indole-5-carboxylic acid methyl ester (5.2 g).

Step 2

To a solution of 1H-indole-5-carboxylic acid methyl ester (3.6 g, 20.6 mmol) in tetrahydrofuran (180 mL) at 0° C., was added sodium hydride (0.65 g, 21.9 mmol). After 10 min., 2-trimethylsilanylethanesulfonyl chloride (4.4 g, 21.9 mmol) was added and the reaction mixture was allowed to warm to room temperature. After 3 h, acetic acid (1.6 mL, 26.8 mmol) was added and the reaction mixture was concentrated. The crude product was chromatographed (Biotage 40M column, 2.5% ethyl acetate-hexanes) to afford 1-(2-trimethylsilanylethanesulfonyl)-indole-5-carboxylic acid methyl ester (5.43 g) as a white solid.

Step 3

To a solution of 1-(2-trimethylsilanylethanesulfonyl)indole-5-carboxylic acid methyl ester (7.4 g, 21.9 mmol) in tetrahydrofuran (100 mL) at −78° C. was added DIBALH® (44 mL, 1.5M, 65.5 mmol) in toluene. The reaction mixture was stirred for 45 min., at −78° C., 10 min. at 0° C., and 15 min. at room temperature. The reaction mixture was recooled to −78° C. and ethyl acetate (100 mL) and saturated aqueous ammonium chloride (50 mL) were added. The reaction mixture was allowed to warm to room temperature and a voluminous white precipitate was filtered over Celite. The biphasic mixture was extracted with ethyl acetate. The combined organic layers were washed with water, dried over magnesium sulfate, and concentrated. The solid residue was triturated with 30% diethyl ether-hexanes and filtered to afford [1-(2-trimethyl-silanylethanesulfonyl)indol-5-yl]methanol (6.7 g) which was used in step 6 below.

Step 4

To a suspension of O-tert-butyl D-serine (2.66 g, 16.5 mmol) in acetonitrile (25 mL) was added trimethylsilyl cyanide (10 mL, 74.5 mmol) and the reaction mixture was heated to 80° C. for 1 h. 4-methoxy-2,3,6-trimethylbenzenesulfonyl chloride (4.3 g, 17.4 mmol) was added and the heating was continued. After 12 h, the reaction mixture was cooled to room temperature and methanol (15 mL) was added. The reaction mixture was concentrated in vacuo and the residue was diluted with diethyl ether (100 mL). The reaction mixture was cooled to 0° C., and the pH adjusted to 8 using 6 N aqueous sodium hydroxide solution. The layers were partitioned and the aqueous layer was extracted with diethyl ether. The aqueous layer was then adjusted to pH 4 and extracted with ethyl acetate. The combined organic extracts were dried over magnesium sulfate and concentrated to afford 2(R)-2-(4-methoxy-2,3,6-trimethylbenzenesulfonylamino)-3-tert-butoxypropionic acid (5.1 g) as a brown foam which was used without further purification.

Step 5

To a solution of 2(R)-(4-methoxy-2,3,6-trimethylbenzenesulfonylamino)-3-tert-butoxypropionic acid (2.79 g, 7.5 mmol) in 70% methanol/methylene chloride (50 mL) at 0° C. was added 1M trimethylsilyldiazomethane in hexanes (22.5 mL, 23 mmol). After 45 min., the reaction mixture was concentrated and chromatographed using preparative chromatography (9% ethyl acetate-hexanes) to afford 2(R)-(4-methoxy-2,3,6-trimethylbenzenesulfonylamino)-3-tert-butoxypropionic acid methyl ester (2.4 g).

Step 6

To a solution of 2(R)-(4-methoxy-2,3,6-trimethylbenzenesulfonylamino)-3-tert-butoxypropionic acid methyl ester (1.1 g, 2.84 mmol) in benzene (50 mL) at 0° C. was added [1-(2-trimethylsilylethanesulfonyl)indol-5-yl]methanol (1.33 g, 4.26 mmol), tri-n-butylphosphine (1.07 mL, 4.26 mmol), followed by 1,1'-[azodicarbonyl]dipiperidine (1.08 g, 4.26 mmol). The reaction mixture was allowed to warm to room temperature over 4 h. After 16 h, the reaction mixture was diluted with an equal volume of hexanes, cooled to 0° C. for 2 h and filtered. The residue was purified by preparative chromatography (20% ethyl acetate-hexanes) to afford 2(R)-{(4-methoxy-2,3,6-trimethylbenzenesulfonyl)-[1-(2-trimethylsilylethanesulfonyl)indol-5-ylmethyl]amino-3-tert-butoxypropionic acid methyl ester (1.79 g) as a pale yellow oil.

Step 7

To a solution of 2(R)-{(4-methoxy-2,3,6-trimethylbenzenesulfonyl)-[1-(2-trimethylsilylethanesulfonyl)indol-5-ylmethyl]amino}-3-tert-butoxypropionic acid methyl ester (1.63 g, 2.55 mmol) in tetrahydrofuran (50 mL) was added 1M tetrabutylammonium fluoride (6.4 mL, 6.4 mmol) in tetrahydrofuran, and the mixture heated to 40° C. After 1 h, the reaction mixture was partitioned between ethyl acetate and 1M hydrochloric acid. The ethyl acetate layer was separated, dried over magnesium sulfate, and concentrated. The residue was purified by preparative chromatography (20% ethyl acetate-hexanes), to afford 2(R)-{(4-methoxy-2,3,6-trimethylbenzenesulfonyl)-[1H-indol-5-ylmethyl]amino}-3-tert-butoxypropionic acid methyl ester (1 g) which was taken directly into the next reaction.

Step 8

To a solution of 2(R)-{(4-methoxy-2,3,6-trimethylbenzenesulfonyl)-[1H-indol-5-ylmethyl]amino}-3-tert-butoxypropionic acid methyl ester (1.0 g, 1.94 mmol) in 50% methanol/tetrahydrofuran (10 mL) was added a solution of LiOH.H$_2$O (160 mg, 3.88 mmol) in water (1 mL). The reaction mixture was heated to 40° C. for 12 h and an additional amount of LiOH.H$_2$O (160 mg, 3.88 mmol) in water (1 mL) was added. After 3 h, the aqueous solution was acidified to pH 3 using 2 N aqueous hydrochloric acid and the product was extracted into ethyl acetate. The combined ethyl acetate layers were dried over magnesium sulfate and concentrated to afford 2(R)-[(1H-indol-5-ylmethyl)-(4-methoxy-2,3,6-trimethylbenzene-sulfonyl)amino]-3-tert-butoxypropionic acid (0.90 g).

Step 9

To a solution of 2(R)-[(1H-indol-5-ylmethyl)-(4-methoxy-2,3,6-trimethylbenzene-sulfonyl)amino]-3-tert-butoxypropionic acid (0.90 g, 1.8 mmol) was added O-benzyl hydroxylamine (0.67 g, 5.4 mmol), 1-hydroxybenzotriazole (0.31 g, 1.98 mmol), N-methylmorpholine (0.36 g, 3.6 mmol), and 1-(dimethylaminopropyl)-3-ethylcarbodiimide (1.04 g, 5.4 mmol). After 16 h, the reaction mixture was diluted with ethyl acetate (200 mL), washed with 2.4 N aqueous hydrochloric acid, saturated aqueous sodium bicarbonate, dried over magnesium sulfate, and concentrated. Purification by preparative chromatography (3% methanol/methylene chloride) gave 2(R)-N-benzyloxy-[(1H-indol-5-ylmethyl)-(4-methoxy-2,3,6-trimethylbenzenesulfonyl)amino]-3-tert-butoxypropionamide (0.85 g).

Step 10

To a solution of 2(R)-N-benzyloxy-[(1H-indol-5-ylmethyl)-(4-methoxy-2,3,6-trimethylbenzenesulfonyl)amino]-3-tert-butoxypropionamide (0.80 g, 1.32 mmol) dissolved in argon deoxygenated 80% ethanol-tetrahydrofuran (100 mL) was added 10% Pd—C (0.4 g), and the resulting mixture was hydrogenated at atmospheric pressure for 60 min. The reaction mixture was degassed under argon, and the slurry was filtered over Celite. The Celite cake was washed with 80% ethanol-methylene chloride, and the filtrate was concentrated. The crude mixture was dissolved in ethyl acetate (5 mL) and slowly added to a rapidly stirring hexanes (300 mL) to produce a precipitate which was filtered and dried (50° C.; 1 torr) to afford N-hydroxy-2(R)-[(1H-indol-5-ylmethyl)-(4-methoxy-2,3,6-trimethylbenzenesulfonyl)amino]-3-tert-butoxypropionamide as a white powder (500 mg).

Proceeding as described in Example 7 above, but substituting [1-(2-trimethylsilanyl-ethanesulfonyl)-1H-indol-5-yl] methanol with 3,4-(methylenedioxy)phenyl methanol, gave 2(R)-[(3,4-methylenedioxybenzyl)-(4-methoxy-2,3,6-trimethyl-benzenesulfonyl)amino]-3-tert-butoxypropionamide.

Example 8

N-hydroxy-2(R)-2-[(1H-indol-5-ylmethyl)-(4-methoxy-2,5-dimethylbenzenesulfonyl)-amino]-3-methylbutyramide (Table I, Cmpd 145)

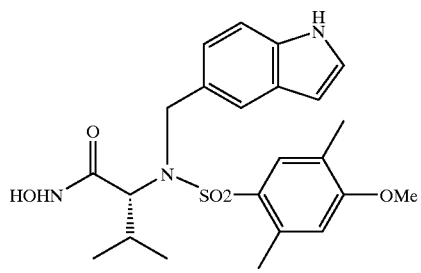

Step 1

To a solution of 1H-indole-5-carboxylic acid methyl ester (16.8 g, 95.9 mmol) in dry acetonitrile (150 mL) was added tert-butoxycarbonyl anhydride (22 g, 100.8 mmol) followed by 4-dimethylaminopyridine (0.58 g, 4.75 mmol). The reaction mixture was stirred for 3 h, then concentrated and chromatographed (300 g SiO$_2$, 5% ethyl acetate-hexanes) to afford N-tert-butoxycarbonylindole-5-carboxylic acid methyl ester (23.6 g) as a colorless oil.

Step 2

To a solution of N-tert-butoxycarbonylindole-5-carboxylic acid methyl ester (23.6 g, 85.7 mmol) in dry tetrahydrofuran (225 mL) at −78° C. was added 1.5 M DIBALH in toluene (171 mL, 257 mmol). After 2 h, the reaction mixture was quenched by the slow addition of methanol (45 mL), water (60 mL), and saturated aqueous NH$_4$Cl (30 mL). The cold bath was removed and after stirring for an additional 1 h, the reaction mixture was filtered over Celite. The Celite cake was washed with tetrahydrofuran and the filtrate was concentrated to remove the more volatile tetrahydrofuran. The biphasic mixture was extracted with ethyl acetate. The combined organic layers were washed with water and the aqueous layer back extracted with ethyl acetate. The combined organic layers were washed with brine, dried over magnesium sulfate, and concentrated to afford N-tert-butoxycarbonylindol-5-yl methanol (21.2 g).

Step 3

To a solution of N-tert-butoxycarbonylindol-5-yl methanol (2.56 g, 10.35 mmol) in dry methylene chloride (60 mL) was added manganese oxide (9 g, 103.5 mmol). The reaction mixture was stirred for 3 h at room temperature and then heated at reflux. After 3 h, the heterogeneous slurry was filtered through Celite and concentrated to afford N-tert-butoxycarbonyl-5-formylindole (2.5 g).

Step 4

To a solution of D-valine benzyl ester hydrochloride (2.49 g, 10.21 mmol) in dry methylene chloride (30 mL) was added N-tert-butoxycarbonyl-5-formylindole (2.5 g, 10.21 mmol) and sodium triacetoxyborohydride (3.24 g, 15.29 mmol). The reaction mixture was stirred for 15 h and then quenched with saturated aqueous sodium bicarbonate. The aqueous layer separated and extracted with methylene chloride. The combined methylene chloride layers were washed with brine, dried over magnesium sulfate, and concentrated. The residue was chromatographed (Biotage 40M column, 10% ethyl acetate-hexanes) to afford 2(R)-[(N-tert-butoxycarbonylindol-5-yl)amino]-3-methylbutyramide O-benzyl ester (3.32 g) as a colorless oil.

Step 5

To a solution of 2(R)-(N-tert-butoxycarbonylindol-5-yl)amino]-3-methylbutyramide O-benzyl ester (2.34 g, 5.36 mmol) in acetonitrile (15 mL) was added trimethylsilylcyanide (2.14 mL, 16.1 mmol). After 1 h, 4-methoxy-2,5-dimethylbenzenesulfonyl chloride (3.18 g, 10.69 mmol) was added and the reaction mixture was heated to 70° C. for 16 h. The reaction mixture was cooled to room temperature. Methanol (15 mL) was then added, and the reaction mixture was concentrated in vacuo. The residue was chromatographed (Biotage 40M column, 10% ethyl acetate-hexanes) to afford 2(R)-[(N-tert-butoxycarbonylindol-5-yl)-(4-methoxy-2,5-dimethylbenzenesulfonyl)amino]-3-methylbutyramide O-benzyl ester (1.56 g) as a colorless oil.

Step 6

To a solution of 2(R)-[(N-tert-butoxycarbonylindol-5-yl)-(4-methoxy-2,5-dimethyl-benzenesulfonyl)amino]-3-methylbutyramide O-benzyl ester (0.45 g, 0.71 mmol) at 0° C. in methylene chloride (10 mL) was added trifluoroacetic acid (2.5 mL). The reaction mixture was stirred 40 min., then warmed to room temperature and stirred for additional 2 h. The reaction mixture was diluted with ethyl acetate. This organic layer was separated and washed with saturated aqueous sodium bicarbonate, dried over magnesium sulfate, and concentrated. The residue was chromatographed (Biotage 40M column, 20% ethyl acetate-hexanes) to afford 2(R)-[(1H-indol-5-yl)-(4-methoxy-2,5-dimethyl-benzenesulfonyl)amino]-3-methylbutyramide O-benzyl ester (0.28 g) as a colorless oil.

Step 7

To solution of 2(R)-[(1H-indol-5-yl)-(4-methoxy-2,5-dimethylbenzenesulfonyl)-amino]-3-methylbutyramide O-benzyl ester (1.1 g, 2.06 mmol) in argon deoxygenated 50% ethanol/tetrahydrofuran (30 mL) was added 10% Pd/C (0.6 g), and the resulting mixture was hydrogenated at atmospheric pressure. After 1.5 h, the reaction mixture was degassed under argon and the slurry was filtered over Celite. The Celite cake was washed with ample 80% ethanol/methylene chloride. The filtrate was concentrated and azeotroped with tetrahydrofuran to give 2(R)-[(1H-indol-5-yl)-(4-methoxy-2,5-dimethylbenzenesulfonyl)-amino]-3-methylbutyric acid (1.014 g), which was used in the next step without further purification.

Step 8

To an ice cooled solution of 2(R)-[(1H-indol-5-yl)-(4-methoxy-2,5-dimethyl-benzenesulfonyl)amino]-3-methylbutyric acid in dimethylformamide (20 mL) was added 1-hydroxybenzotriazole monohydrate (384 mg, 2.51 mmol), O-benzylhydroxylamine (844 mg, 6.85 mmol), N-methylmorpholine (462 mg, 4.57 mmol), and 1-(dimethylaminopropyl)-3-ethylcarbodiimide (1.31 g, 6.85 mmol). The reaction mixture was warmed to room temperature. After 16 h, the reaction mixture was partitioned between ethyl acetate (300 mL) and 1.5% aqueous hydrochloric acid (50 mL). The ethyl acetate layer was washed with saturated aqueous sodium bicarbonate, dried over magnesium sulfate and concentrated. The residue was chromatographed (Biotage 40M column, 50% EtOAc-Hexanes) to afford N-benzyloxy-2-[(1H-indol-5-ylmethyl)-(4-methoxy-2,5-dimethylbenzenesulfonyl)amino]-3-methyl-butyramidehydroxamate (0.61 g).

Step 9

To a solution of N-benzyloxy-2-[(1H-indol-5-ylmethyl)-(4-methoxy-2,5-dimethylbenzenesulfonyl)amino]-3-methyl-butyramidehydroxamate (0.61 g, 1.1 mmol) in argon deoxygenated 50% ethanol/tetrahydrofuran mixture (20 mL) was added 10% Pd—C (600 mg). The resulting reaction mixture was hydrogenated at atmospheric pressure for 2 h. The reaction mixture was degassed under argon and the slurry was filtered over Celite. The Celite cake was washed with ample 80% ethanol/methylene chloride mixture and the filtrate was concentrated. The crude mixture was dissolved in ethyl acetate (1 mL). This solution was slowly added a rapidly stirring hexanes (100 mL) to produce a precipitate. The precipitate was filtered and dried (50 ° C.; 1 torr) to afford 2(R)-N-Hydroxy-2-[(1H-indol-5-ylmethyl)-(4-methoxy-2,5-dimethylbenzenesulfonyl)amino]-3-methylbutyramide (477 mg) as a white powder.

Example 9

N-hydroxy-2(R)-2-[(3,4-methylenedioxybenzyl)-(4-methoxy-2,6-dimethylbenzene-sulfonyl)amino]-3-methylbutyramide (Table I, Cmpd 40)

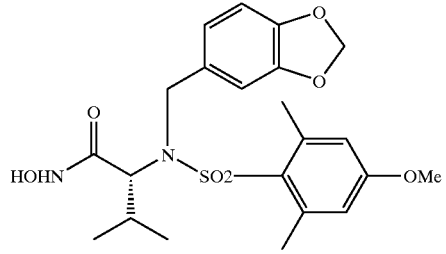

Step 1

To a solution of D-valine benzyl ester free base (12.92 g, 62 mmol) in dry methylene chloride (120 mL) was added 3,4-(methylenedioxy)phenyl methanol (9.45 g, 62 mmol) and sodium triacetoxyborohydride (18.50 g, 86.8 mmol). After 15 h, the reaction mixture was quenched with saturated aqueous sodium bicarbonate (120 mL) and the aqueous layer was separated and extracted with methylene chloride. The combined methylene chloride layers were washed with brine, dried over magnesium sulfate, and concentrated. The residue was chromatographed (300 g $SiO_2$, 5% ethyl acetate-hexanes) to afford 2(R)-(3,4-methylenedioxy-benzylamino)-3-methylbutyric acid benzyl ester (18 g) as a colorless oil.

Step 2

To a solution of 2(R)-(3,4-methylenedioxybenzylamino)-3-methylbutyric acid benzyl ester (3.0 g, 8.79 mmol) in acetonitrile (15 mL) was added trimethylsilyl cyanide (3.5 mL, 26.3 mmol). The reaction mixture was heated to 80° C. After 1 h, 4-methoxy-2,6-dimethylbenzenesulfonyl chloride (3.14 g, 10.55 mmol) was added and heating was continued. After 36 h, the reaction mixture was cooled to room temperature. Methanol was added (15 mL), and the solution was concentrated in vacuo. The residue was chromatographed (Biotage 40M column, 10% ethyl acetate-hexanes) to afford 2(R)-2-[(3,4-methylenedioxybenzyl)-(4-methoxy-2,6-dimethylbenzenesulfonyl)amino]-3-methylbutyric acid benzyl ester (4.33 g) as a colorless oil.

Step 3

To solution of 2(R)-2-[(3,4-methylenedioxybenzyl)-(4-methoxy-2,6-dimethyl-benzenesulfonyl)amino]-3-methylbutyric acid benzyl ester (2.6 g, 4.81 mmol) in argon deoxygenated 50% ethanol/tetrahydrofuran mixture (20 mL) was added 10% Pd/C (2 g). The resulting mixture was hydrogenated at atmospheric pressure for 3 h. The reaction mixture was degassed under argon and the slurry filtered over Celite and washed with ample 80% ethanol/methylene chloride mixture. The filtrate was concentrated and azeotroped with tetrahydrofuran (22 mL) and the residue was dissolved in methylene chloride (20 mL). The solution was cooled to 0° C. and oxalyl chloride (0.8 mL, 9.17 mmol) and 4 drops of dimethylformamide were added. The reaction mixture was warmed to room temperatuer, stirred 4 h and then concentrated. The crude acid chloride was then dissolved in methylene chloride (20 mL), cooled to 0° C., and N,O-bis-trimethylsilylhydroxylamine (4 mL, 18.7 mmol) was added. The reaction mixture was warmed to room temperatuer and after 3 h methanol (20 mL) was added. After 30 min. the reaction mixture was concentrated and chromatographed using preparative TLC plates (5% methanol/methylene chloride) to afford N-hydroxy-2(R)-2-[(3,4-methylenedioxy-benzyl)-(4-methoxy-2,6-dimethylbenzenesulfonyl)amino]-3-methylbutyramide (1.0 g).

Example 10

N-Hydroxy-2(R)-[(4-methoxybenzenesulfonyl)-(1H-benzimidazol-5-ylmethyl)amino]-3-methylbutyramide (Table I, Cmpd 35)

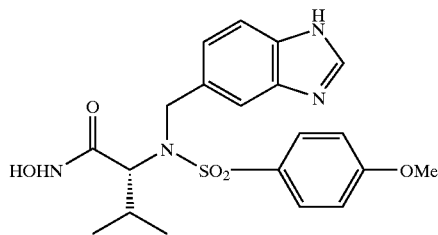

Step 1

To an ice-cooled solution of 2(R)-(4-methoxybenzenesulfonylamino)-3-methylbutyric acid (7.0 g, 21.25 mmol) in dry methylene chloride was added N,N'-diisopropyl-O-tert-butylisourea (12.1 mL, 3.5M) via addition funnel over 45 min. The reaction mixture was maintained at 0° C. for 2 h and then allowed to warm to room temperature overnight. The reaction mixture was loaded onto a flash silica gel column and eluted with ethyl acetate/hexane (5%) to give 2(R)-(4-methoxybenzenesulfonylamino)-3-methylbutyric acid tert-butyl ester (7.02 g) as a white crystalline solid.

Step 2

To a mixture of 4-amino-3-nitrobenzoic acid (10 g, 54.9 mmol) and trimethylsilyl cyanide (20.6 mL, 3 equiv.) in dry acetonitrile (120 mL) was added o-phthaloyl-dichloride (7.9 mL, 54.9 mmol) and the material was heated to reflux. After 8 h, an additional amount of o-phthaloyl dichloride (1 mL, 6.94 mmol) was added. After 16 h, the reaction mixture was cooled to room temperature and ethyl acetate (100 mL) was added. The organic layer was separated and washed consecutively with equal volumes of 5% hydrochloric acid and then brine. The aqueous phases were back extracted with ethyl acetate (150 mL). The residue was crystallized from hot ethyl acetate/hexane to give 3-nitro-4-(aminophthaloyl)benzoic acid (5.85 g) as a crystalline brown solid.

Step 3

To a mixture of 3-nitro-4-(aminophthaloyl)benzoic acid (5.85 g, 18.74 mmol) and diisopropylethylamine (3.9 mL, 22.49 mmol) in tetrahydrofuran (120 mL) was added benzotriazol-1-yloxy-tris-(dimethylamino)phosphonium hexafluorophosphate (9.95 g, 22.49 mmol). The material was stirred for 5 min. Sodium borohydride (744 mg, 19.7 mmol) was added in three portions over 5 min. and the reaction mixture was stirred for 0.5 h. Ethyl acetate (100 mL) was added and the organic phase was washed consecutively with equal volumes of 5% hydrochloric acid, 5% sodium bicarbonate, and brine and back extracted with ethyl acetate (150 mL). The organic phase was condensed on the rotoevaporator and the residue was purified by flash silica gel chromatography using ethyl acetate/hexane (50%) as eluant, to provide 3-nitro-4-(aminophthaloyl)benzyl alcohol as a yellow solid (4.61 g).

Step 4

To a mixture of 2(R)-(4-methoxybenzenesulfonylamino)-3-methylbutyric acid tert-butyl ester (1.91 g, 5.6 mmol), 3-nitro-4-(aminophthaloyl)benzyl alcohol (1.75 g, 5.87 mmol) and tributylphophine (1.5 mL, 5.87 mmol) in dry benzene (40 mL) was added (1,1'-azo-dicarbonyl)dipiperidine (1.48 g, 5.87 mmol). The reaction mixture was stirred overnight and then loaded onto a flash silica gel column. The column was eluted with ethyl acetate/hexane (5–15%) to give 2(R)-{[(3-nitro-4-(aminophthaloyl)benzyl]-(4-methoxybenzenesulfonyl)-amino}-3-methylbutyric acid tert-butyl ester (437 mg).

Step 5

To a solution of 2(R)-{[(3-nitro-(4-aminophthaloyl)benzyl]-(4-methoxybenzene-sulfonyl)amino}-3-methylbutyric acid tert-butyl ester (420 mg, 0.673 mmol) in ethanol/tetrahydrofuran (15 mL of 1:1 ratio) was added 10% Pd/C (40 mg). The reaction mixture was placed under a hydrogen balloon and stirred for 4 h. The reaction mixture was filtered through a short plug of Celite (2 g, on a sintered glass funnel) and washed well with ethanol (100 mL). The filtrate was concentrated to give 2(R)-{[(3-amino-(4-aminophthaloyl)benzyl]-(4-methoxybenzenesulfonyl)amino}-3-methylbutyric acid tert-butyl ester (375 mg).

Step 6

To a solution of 2(R)-{[(3-amino-4-(aminophthaloyl)benzyl]-(4-methoxybenzene-sulfonyl)amino}-3-methylbutyric acid tert-butyl ester (370 mg, 0.623 mmol) in methanol/methylene chloride (12 mL, ratio of 1:1) is added hydrazine (0.39 mL, 20 equiv.). The reaction mixture was stirred for 16 h. The reaction mixture was filtered and the filtrate concentrated on a rotoevaporator. A residue was filtered and the filtrate was again concentrated on the rotoevaporator to provide 2(R)-{[(3,4-diamino)benzyl]-(4-methoxy-benzenesulfonyl)amino}-3-methylbutyric acid tert-butyl ester (288 mg).

Step 7

To a mixture of 2(R)-{[(3,4-diamino)benzyl]-(4-methoxybenzenesulfonyl)amino}-3-methylbutyric acid tert-butyl ester (90 mg, 0.194 mmol) and trimethyl orthoformate (0.022 mL, 1.05 equiv.) in dry toluene (10 mL) was added KSF montmorillonite clay (25 mg). The reaction mixture was heated at reflux for 6.5 h and then cooled to room temperature. After reaching room temperature, the mixture was condensed in vacuo and the residue was loaded onto a preparatory thin layer chromatography plate. Elution with methanol/methylene chloride (10%) provided 2(R)-[(benzimidazol-5-ylmethyl)-(4-methoxy-benzenesulfonyl)amino]-3-methylbutyric acid tert-butyl ester (79 mg).

Step 8

A solution of 2(R)-[(benzimidazol-5-ylmethyl)-(4-methoxybenzenesulfonyl)amino]-3-methylbutyric acid tert-butyl ester (74 mg, 0.156 mmol) in a 1:4 trifluoroacetic acid/methylene chloride mixture (5 mL) was stirred for 2 h. The reaction mixture was concentrated on a roto-evaporator and then on high-vac pump to give 2(R)-[(benzimidazol-5-ylmethyl)-(4-methoxy-benzenesulfonyl)amino]-3-methylbutyric acid (approx. 0.135 mmol).

Step 9

To a solution of 2(R)-[(benzimidazol-5-ylmethyl)-(4-methoxybenzenesulfonyl)-amino]-3-methylbutyric acid (0.13 mmol), O-benzylhydroxylamine (0.1 mL, 0.52 mmol), 1-hydroxybenzotriazole hydrate (24 mg, 0.16 mmol), and N-methylmorpholine (0.05 mL, 0.39 mmol) in anhydrous dimethylformamide (10 mL) was added 1-ethyl-3(3- dimethylamino)-propyl carbodiimide hydrochloride salt (45 mg, 0.24 mmol). The reaction mixture was stirred overnight and then condensed on the roto-evaporator. The residue was taken up in ethyl acetate (40 mL) and washed consecutively with equal volumes of 2% aqueous ammonium chloride, 5% sodium bicarbonate, and brine and then concentrated in vacuo. The residue was purified by preparative thin layer chromatography using methanol/methylene chloride (10%) as eluant to give 2(R)-N-benzyloxy-[(benzimidazol-5-ylmethyl)-(4-methoxybenzene-sulfonyl)amino]-3-methylbutyramide (48 mg, 71%).

Step 10

To a solution of 2(R)-N-benzyloxy-[(benzimidazol-5-ylmethyl)-(4-methoxybenzene-sulfonyl)amino]-3-methylbutyramide (42 mg, 0.08 mmol), in a 3:1 mixture of ethanol/tetrahydrofuran (10 mL), was added 10% Pd/C (40 mg). The reaction mixture was placed under a hydrogen balloon. After 2 h, the reaction mixture was filtered through a short plug of Celite (1 g on a sintered glass funnel) and the Celite pad was washed with ethanol (100 mL). The filtrate was concentrated on a roto-evaporator and the residue was purified by preparative thin layer chromatography using methanol/methylene chloride (10%) as the eluent to give N-hydroxy-2(R)-[(benzimidazol-5-ylmethyl)-(4-methoxybenzenesulfonyl)amino]-3-methylbutyramide (23 mg).

Example 11

N-hydroxy-2(R)-[(1H-3-acetyl-indol-5-ylmethyl)-(4-methoxy-2,3,6-trimethylbenzenesulfonyl)amino]-3-methylbutyramide (Table I, Cpd. 126)

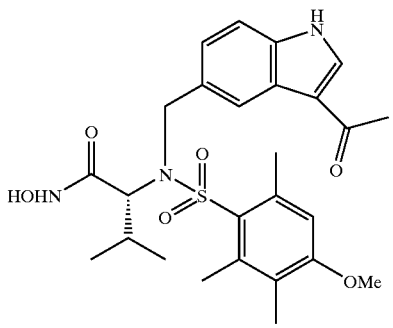

Step 1

To an oven dried flask, under nitrogen atmosphere containing 2(R)-[(1H-indol-5-ylmethyl)-(4-methoxy-2,3,6-trimethylbenzenesulfonyl)amino]-3-methylbutyric acid methyl ester, (1.41 g, 2.98 mmol), [prepared by the method of Example 2, Step 1, and instead of Example 2, Step 2 (alkylation of the carboxylic acid with benzyl bromide), the methyl ester is formed using trimethylsilydiazomethane (see Example 3, Step 1)], was added N,N-dimethylacetamide (1.75 ml, 14.9 mmol) followed by dropwise addition of phosphorus oxychloride (1.4 ml, 11.92 mmol), with vigorous stirring. After complete addition the mixture was heated (80–90° C., oil bath) for 3.5 hours. The material was cooled to ambient temperature and 1 $\underline{N}$ sodium hydroxide was added with vigorous mechanical stirring. After five minutes methylene chloride and water (1:1; 120 ml) were added and the material was partitioned and the organic phase collected. The methylene chloride phase was then washed consecutively with equal volumes of water and brine and the aqueous phases were back extracted with methylene chloride (2×60 ml). The combined organic phases were dried with magnesium sulfate, filtered and condensed. The residue was purified by preparative thin layer chromatography on silica gel using 3% methanol-methylene chloride as eluant, providing 2(R)-[(1H-3-acetyl-indol-5-ylmethyl)-(4-methoxy-2,3,6-trimethylbenzenesulfonyl)amino]-3-methylbutyric acid methyl ester (815 mg) as a golden viscous oil.

Step 2

To a solution of 2(R)-[(1H-3-acetyl-indol-5-ylmethyl)-(4-methoxy-2,3,6-trimethylbenzenesulfonyl)amino]-3-methylbutyric acid methyl ester (805 mg, 1.56 mmol), in methanol (30 ml) was added a aqueous solution of 1.0 $\underline{N}$ lithium hydroxide (3.1 ml). The mixture was heated under reflux for 12 hours. Extra 1.0 $\underline{N}$ lithium hydroxide (3.1 ml) was added and the mixture heated for an additional eight hours. The material was cooled to ambient temperature and concentrated in vacuo and the residue taken up in water-ether (1:1, 50 ml). The layers were partitioned and the aqueous layer was collected and acidified (5% aqueous HCl to pH=3) in the presence of an equal volume of ethyl acetate. The ethyl acetate phase was collected and washed with an equal volume of brine. The aqueous phases were back extracted with ethyl acetate (2×80 ml), combined, dried with magnesium sulfate, filtered and condensed to provide 2(R)-[(1H-indol-3-acetyl-5-ylmethyl)-(4-methoxy-2,3,6-trimethylbenzenesulfonyl)amino]-3-methylbutyric acid, (586 mg) as a tan colored solid powder.

Step 3

To a mixture of 2(R)-[(1H-3-acetyl-indol-5-ylmethyl)-(4-methoxy-2,3,6-trimethylbenzenesulfonyl)amino]-3-methylbutyric acid (580 mg, 1.16 mmol), 2,4-dimethoxybenzyl hydroxylamine (255 mg, 5.15 mmol), 1-hydroxybenzotriazole hydrate (178 mg, 1.16 mmol), and N-methyl morpholine (0.2 ml, 1.74 mmol) in dry dimethyl formamide was added 1-(3-dimethylaminopropyl)-3-ethylcarbodiimide hydrochloride salt (333 mg, 1.74 mmol). The reaction mixture was stirred overnight and then concentrated on the rotary evaporator-pump. The residue was taken up in ethyl acetate (80 ml) and a 2% aqueous solution of ammonium chloride (80 ml) and partitioned. The organic phase was collected and washed consecutively with equal volumes of 5% aqueous sodium bicarbonate and brine. The aqueous phases were back extracted with ethyl acetate (2×80 ml) and the combined organic phases were dried over magnesium sulfate and concentrated in vacuo to afford crude N-(2,4-dimethoxy)benzyloxy-2(R)-[(1H-3-N-(2,4-dimethoxybenzyloxyiminoacetyl)-indol-5-ylmethyl)-(4-methoxy-2,3,6-trimethylbenzenesulfonyl)amino]-3-methylbutyramide, which was taken directly into the next step without further purification.

Step 4

To a solution of N-(2,4-dimethoxy)benzyloxy-2(R)-[(1H-3-N-(2,4-dimethoxybenzyloxyiminoacetyl)-indol-5-ylmethyl)-(4-methoxy-2,3,6-trimethylbenzenesulfonyl)amino]-3-methylbutyramide (assumed 1.1 mmol) in 5% trifluoroacetic acid-tetrahydrofuran (15 ml) and water (2 ml) was added triethylsilane (0.7 ml, 3.9 mmol). The mixture was stirred for one hour at ambient temperature and then extra trifluoroacetic acid (0.5 ml) was added. The material was heated (60–70° C.) under nitrogen atmosphere. After 0.5 hour additional trifluoroactic acid (0.5 ml) was added and heating was maintained for a total of four hours. The mixture was cooled to ambient temperature and diluted with water (60 ml) and ethyl acetate (60 ml). The material was partitioned and the organic phase collected and washed with an equal volume of brine. The aqueous phases were back extracted with ethyl acetate (2×60 ml), combined and dried with magnesium sulfate. The material was condensed and the residue purified by preparative thin layer chromatography on silica gel, using 10% methanol-methylene chloride as eluant, providing N-hydroxy-2(R)-[(1H-3-acetylindol-5-ylmethyl)-(4-methoxy-2,3,6-trimethylbenzenesulfonyl) amino]-3-methylbutyramide (320 mg) as a tan solid powder.

Example 12

N-hydroxy-2(R)-[(3,4-methylendioxybenzyl)-(2,6-dimethyl-4-methoxybenzenesulfonyl)amino]-3-(methanesulfonyl)amino-propionamide (Table 1, Cpd. 128)

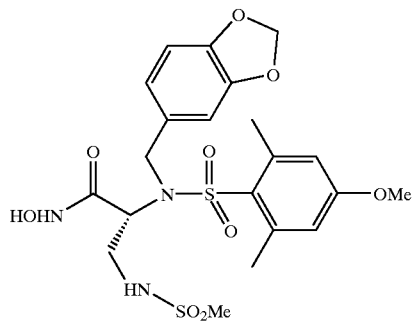

Step 1

To an ice-cooled solution of N-BOC-D-serine (10 g, 48.7 mmol) in methylene chloride (50 ml) was added N,N'-diisopropyl-O-tert-butylisourea (35 ml, 3.5 M) via addition funnel, over 30 min. The reaction mixture was maintained at 0° C. for 2 hrs and then warmed to room temperature over night. The material was again cooled to 0° C. and a second portion of N,N'-diisopropyl-O-tert-butylisourea (28 ml, 3.5 M) was added. The material was stirred for 2 hrs at 0° C. and then warmed again to room temperature over night. Purification by flash silica gel chromatography using (20%) ethyl acetate/hexanes as eluant gave O-tert-butyl-N-BOC-D-serine (7.97 g) as a viscous oil which solidified on standing.

Step 2

To a solution of O-tert-butyl-N-BOC-D-serine (4 g, 15.31 mmol), phthalimide (3.38 g, 22.9 mmol) and triphenyl phosphine (6.03 g, 22.9 mmol) in tetrahydrofuran (120 ml, anhydrous) was added diisopropyl azodicarboxylate (4.5 ml, 22.9 mmol). The mixture was stirred under nitrogen atmosphere over night. The tetrahydrofuran was removed on the roto-evaporator and the remainder was taken up in methylene chloride (60 ml) and loaded onto a flash silica gel column. Elution with ethyl acetate/hexanes (19%) gave tert-butyl-2(R)-[(tert-butoxycarbonyl)amino]-3-phthalimido-propionate (3.74 g) as a white powder.

Step 3

Tert-butyl-2(R)-[(tert-butoxycarbonyl)amino]-3-phthalimido-propionate (8.58 g, 21.8 mmol) was taken up in a anhydrous solution of hydrochloric acid in dioxane (100 ml, 4% wt/wt). The reaction flask was fitted with a rotovap trap, which was topped with a teflon stopper and the mixture was heated to 80° C. (use a plexiglass shield for safety). After 1.5 hours the material was cooled to ambient temperature and all volatiles removed on the rotary evaporator. The white solid was taken up in methylene chloride (100 ml) and transferred to a seperatory funnel. The solution was partitioned with an equal volume of aqueous sodium hydroxide (1.0 N) and the organic phase collected. This was subsequently shaken with brine solution (2×100 ml, consecutively) and the aqueous phases back extracted with methylene chloride (3×100 ml). The organic phases were combined, dried (MgSO$_4$), filtered and condensed to provide tert-butyl-2(R)-amino-3-phthalimido-propionate (5.7 g) as a white powder.

Step 4

To a stirred solution of tert-butyl-2(R)-amino-3-phthalimido-propionate (5.7 g, 19.63 mmol) in dry acetonitrile (60 ml) was added trimethylsilylcyanide (8.6 ml, 68.7 mmol). After 5 minutes 2,6-dimethyl-4-methoxybenzenesulfonyl chloride (4.84 g, 20.6 mmol) was added in one portion. The material was stirred at ambient temperature for 1 hour and then ethyl acetate (80 ml) was added and the mixture was transferred to a seperatory funnel. The organic phase was partioned with aqueous hydrochloric acid (1.5%, 100 ml), collected and washed with an equal volume of brine. The aqueous phases were back extracted with ethyl acetate (2×80 ml) and the organic phases combined, dried (magnesium sulfate), filtered and condensed. The residue was chromatographed (flash silica gel, 30% ethyl acetate-hexanes) to provide tert-butyl 2(R)-(2,6-dimethyl-4-methoxybenzene sulfonylamino)-3-phthalimido-propionate as white semi-solid (6.9 g).

Step 5

To a cooled (ice bath) solution of tert-butyl 2(R)-(2,6-dimethyl-4-methoxybenzene sulfonylamino)-3-phthalimido-propionate (6.9 g, 14.12 mmol) in dry benzene (150 ml) with piperonyl alcohol (3.22 g, 21.2 mmol) and tributyl phosphine (5.3 ml, 21.2 mmol) was added 1,1'-(azodicarbonyl)-dipiperidine (5.35 g, 21.2 mmol). The mixture was allowed to warm to ambient temperature overnight. The material was loaded onto a flash silica gel column using ethyl acetate-hexanes (30%) as eluant, providing tert-butyl 2(R)-[(3,4-methylendioxybenzyl)-(2,6-dimethyl-4-methoxybenzenesulfonyl)amino]-3-phthalimido-propionate as a white solid (8.59 g).

Step 6

To a stirred solution of tert-butyl 2(R)-[(3,4-methylendioxybenzyl)-(2,6-dimethyl-4-methoxybenzenesulfonyl)amino]-3-phthalimido-propionate (3.9 g, 6.2 mmol) in a mixture of 78% methylene chloride/methanol (47 ml) was added hydrazine hydrate (3.9 ml, 125 mmol) and the mixture was stirred for five hours, at which time a solid precipitate of phthalhydrazide was observed to form. The material was filtered, washing with methylene chloride, to remove the precipitate. The filtrate was then evaporated on the rotovap and taken up in methylene chloride (80 ml) and transferred to a separatory funnel. After partitioning with an equal volume of water, the organic phase was collected and washed with an equal volume of brine. The aqueous phases were back extracted with methylene chloride (2×80 ml). The methylene chloride phases were combined, dried (MgSO$_4$), filtered and condensed to provide tert-butyl 2(R)-[(3,4-methylendioxybenzyl)-(2,6-dimethyl-4-methoxybenzenesulfonyl)amino]-3-amino-propionate as a white semi-solid (3.0 g).

Step 7

To a mixture of tert-butyl 2(R)-[(3,4-methylendioxybenzyl)-(2,6-dimethyl-4-methoxybenzenesulfonyl)amino]-3-amino-propionate (1.02 g, 2.0 mmol), with trimethylsilyl cyanide (0.7 ml, 5.2 mmol) in dry acetonitrile (15 ml) was added methanesulfonyl chloride (0.18 ml, 2.3 mmol) and the material was stirred overnight. Ethyl acetate (80 ml) was added and the material was partitioned with aqueous hydrochloric acid (1.5%, 80 ml). The organic phase was collected and washed with an equal volume of brine. The aqueous phases were back extracted with ethyl acetate (2×80 ml) and the organic phases combined, dried (MgSO₄), filtered and condensed to provide tert-butyl 2(R)-[(3,4-methylendioxybenzyl)-(2,6-dimethyl-4-methoxybenzenesulfonyl)amino]-3-methanesulfonylamino-propionate as a pale yellow semi-viscous oil (1.4 g).

Step 8

A solution of tert-butyl 2(R)-[(3,4-methylendioxybenzyl)-(2,6-dimethyl-4-methoxybenzenesulfonyl)amino]-3-methanesulfonylamino-propionate (1.37 g, 2 mmol) in 20% trifluoracetic acid-methylene chloride (15 ml) was stirred for 1 hour. Extra trifluoroacetic acid (0.5 ml) was added and stirring continued for two hours. The material was then condensed on the rotary evaporator and the residue was taken up in toluene (40 ml) and again condensed. This procedure was repeated twice (2×40 ml toluene, to remove traces of trifluoracetic acid) to provide 2(R)-[(3,4-methylendioxybenzyl)-(2,6-dimethyl-4-methoxybenzenesulfonyl)amino]-3-methanesulfonylamino-propionic acid as a tan green foamy solid (1.02 g).

Step 9

To a mixture of 2(R)-[(3,4-methylendioxybenzyl)-(2,6-dimethyl-4-methoxybenzenesulfonyl)amino]-3-methanesulfonylamino-propionic acid (1 g, 1.9 mmol), O-benzylhydroxylamine (0.95 ml, 6 mmol) and 1-hydroxybenzotriazole hydrate (370 mg, 1.9 mmol), and N-methylmorpholine (0.7 ml, 5.7 mmol) in anhydrous dimethylformamide (20 ml) was added 1-ethyl-3(3-dimethylamino)-propyl carbodiimide hydrochloride salt. The mixture was stirred overnight and then condensed on the roto-evaporator. The remainder was taken up in ethyl acetate (60 ml) and partitioned with an equal volume of 5% aqueous hydrochloric acid. The ethyl acetate phase was collected and washed consecutively with equal volumes of 5% sodium bicarbonate and brine. The aqueous phases were back extracted with ethyl acetate (2×60 ml) and the organic layers combined, dried with magnesium sulfate, filtered and condensed. The residue was purified by preparative thin layer chromatography using 65% ethyl acetate-hexanes as eluant providing N-benzyloxy 2(R)-[(3,4-methylendioxybenzyl)-(2,6-dimethyl-4-methoxybenzenesulfonyl)amino]-3-methanesulfonylamino-propionamide as a yellow viscous oil (591 mg).

Step 10

To a solution of N-benzyloxy-2(R)-[(3,4-methylendioxybenzyl)-(2,6-dimethyl-4-methoxybenzenesulfonyl)amino]-3-methanesulfonylamino-propionamide (580 mg, 0.94 mmol) in a 3:1 mixture of ethanol/tetrahydrofuran (30 ml) was added 10% palladium on charcoal (60 mg). The reaction mixture was placed under a hydrogen balloon and stirred for 6 hours. The material was filtered through a short plug of silica, rinsing with ethanol (200 ml). The filtrate was condensed on the roto-evaporator and the residue was purified by preparative thin layer chromatography using 8.5% methanol-methylene chloride as eluant providing N-hydroxy-2(R)-[(3,4-methylendioxybenzyl)-(2,6-dimethyl-4-methoxybenzenesulfonyl)amino]-3-methanesulfonylamino-propionamide as a tan powder (223 mg).

Replacement of methanesulfonyl chloride in Step 7 with:
benzenesulfonyl chloride,
acetyl chloride,
benzoyl chloride,
4-methoxycarbonyl-benzoyl chloride, and
methyl chloroformate; gave
N-hydroxy-2(R)-[(3,4-methylendioxybenzyl)-(2,6-dimethyl-4-methoxybenzenesulfonyl)amino]-3-benzenesulfonylamino-propionamide, (Table 1, Cpd. 129)

N-hydroxy-2(R)-[(3,4-methylendioxybenzyl)-(2,6-dimethyl-4-methoxybenzenesulfonyl)amino]-3-acetylamino-propionamide, (Table 1, Cpd. 130)

N-hydroxy-2(R)-[(3,4-methylendioxybenzyl)-(2,6-dimethyl-4-methoxybenzenesulfonyl)amino]-3-benzoylamino-propionamide, Table I, Cpd. 138)

N-hydroxy-2(R)-[(3,4-methylendioxybenzyl)-(2,6-dimethyl-4-methoxybenzenesulfonyl)amino]-3-(4-methoxycarbonyl-benzoyl)amino-propionamide, (Table I, Cpd. 133) and N-hydroxy-2(R)-[(3,4-methylendioxybenzyl)-(2,6-dimethyl-4-methoxybenzenesulfonyl)amino]-3-methoxycarbonylamino-propionamide (Table I, Cpd. 131).

Example 13

N-hydroxy-2(R)-[(3,4-methylendioxybenzyl)-(2,6-dimethyl-4-methoxybenzenesulfonyl)amino]-3-[(2-pyrrol-1-yl)-phenylcarbonylamino]-propionamide
(Table I, Cmpd. 143)

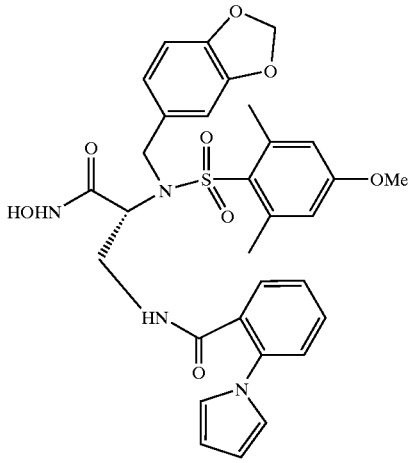

Step 1

To a mixture of tert-butyl-2(R)-[(3,4-methylendioxybenzyl)-(2,6-dimethyl-4-methoxybenzenesulfonyl)amino]-3-amino-propionate (1.02 g, 2.0 mmol), 1-(2-carboxyphenyl)pyrrole (581 mg, 3.1 mmol), 1-hydroxybenzotriazole hydrate (279 mg, 2.0 mmol), N-methylmorpholine (0.8 ml, 7.3 mmol) and 4-dimethylaminopyridine (30 mg; 0.25 mmol) in dry dimethylformamide (25 ml) was added 1-ethyl-3,3-dimethylamino)-propyl carbodiimide hydrochloride salt (600 mg, 3.1 mmol) and the material was stirred overnight. The dimethylformamide was removed on the rotary evaporator and the residue was taken up in ethyl acetate (80 ml) and partitioned with an equal volume of aqueous hydrochloric acid (1.5%, 80 ml). The organic phase was collected and washed with equal volumes of 5% aqueous sodium bicarbonate and then brine. The aqueous phases were back extracted with ethyl acetate (2×80 ml) and the organic phases combined, dried over magnesium sulfate, filtered and condensed to provide a residue. This material was chromatographed using preparative TLC plates (45% ethyl acetate/hexanes) to afford tert-butyl-2(R)-[(3,4-methylendioxybenzyl)-(2,6-dimethyl-4-methoxybenzenesulfonyl)amino]-3-[(2-pyrrol-1-yl) phenylcarbonylamino]-propionate) as a pale yellow foamy solid (927 mg).

Step 2

A solution of tert-butyl-2(R)-[(3,4-methylendioxybenzyl)-(2,6-dimethyl-4-methoxybenzenesulfonyl)amino]-3-[(2-pyrrol-1-yl) phenylcarbonylamino]-propionate (915 mg, 1.3 mmol) in 20% trifluoracetic acid-methylene chloride (15 ml) was stirred for 1 hour. Extra trifluoroacetic acid (0.5 ml) was added and stirring continued for 1.5 hours. The material was then condensed on the rotary evaporator and the residue was taken up in toluene (40 ml) and again condensed. This procedure was repeated twice (2×40 ml toluene, to remove traces of trifluoracetic acid) to provide 2(R)-[(3,4-methylendioxybenzyl)-(2,6-dimethyl-4-methoxybenzenesulfonyl)amino]-3-[(2-pyrrol-1-yl) phenylcarbonylamino]-propionic acid as a golden tan solid (896 mg).

Step 3

To a mixture of 2(R)-[(3,4-methylendioxybenzyl)-(2,6-dimethyl-4-methoxybenzenesulfonyl)amino]-3-[(2-pyrrol-1-yl)phenylcarbonylamino]-propionic acid (approximately 1.3 mmol), O-benzylhydroxylamine (0.6 ml, 3.9 mmol) and 1-hydroxybenzotriazole hydrate (199 mg, 1.3 mmol), and N-methylmorpholine (0.44 ml, 3.9 mmol) in anhydrous dimethylformamide (20 ml) was added 1-ethyl-3(3-dimethylamino)-propyl carbodiimide hydrochloride salt (375 mg, 1.95 mmol). The mixture was stirred overnight and then condensed on the roto-evaporator. The remainder was taken up in ethyl acetate (60 ml) and partitioned with an equal volume of 1.5% aqueous hydrochloric acid. The ethyl acetate phase was collected and washed consecutively with equal volumes of 5% sodium bicarbonate and then brine. The aqueous phases were back extracted with ethyl acetate (2×60 ml) and the organic layers combined, dried with magnesium sulfate, filtered and condensed. The residue was purified by preparative TLC (2% methanol-methylene chloride) providing N-benzyloxy-2(R)-[(3,4-methylendioxybenzyl)-(2,6-dimethyl-4-methoxybenzenesulfonyl)amino]-3-[(2-pyrrol-1-yl) phenylcarbonylamino]-propionamide as a light yellow foamy solid (490 mg).

Step 4

To a solution of benzyloxy-2(R)-[(3,4-methylendioxybenzyl)-(2,6-dimethyl-4-methoxybenzenesulfonyl)amino]-3-(2'pyrrolo)benzamido-propionamide (480 mg, 0.675 mmol) in a 3:1 mixture of ethanol/tetrahydrofuran (30 ml) was added 10% palladium on charcoal (60 mg). The reaction mixture was placed under a hydrogen balloon and stirred for 8 hours during which time additional catalyst (2×60 mg) was added. The material was filtered through a short plug of silica, rinsing with ethanol (200 ml). The filtrate was condensed on the roto-evaporator and the residue was purified by preparative TLC (7% methanol-methylene chloride) providing a mixture of N-hydroxy-2(R)-[(3,4-methylendioxybenzyl)-(2,6-dimethyl-4-methoxybenzenesulfonyl)amino]-3-[(2-pyrrol-1-yl)phenylcarbonylamino]-propionamide and N-hydroxy-2(R)-[(3,4-methylendioxybenzyl)-(2,6-dimethyl-4-methoxybenzenesulfonyl)amino]-3-[(2-pyrrolidin-1-yl) phenylcarbonylamino]-propionamide (82:18) as a tan powder (216 mg).

Example 14

N-hydroxy-2(R)-[(3,4-methylenedioxybenzyl)-(4-methoxy-2,3,6-trimethylbenzenesulfonyl)amino]-3 (S)-hydroxybutyramide (Table I, Cmpd. 94)

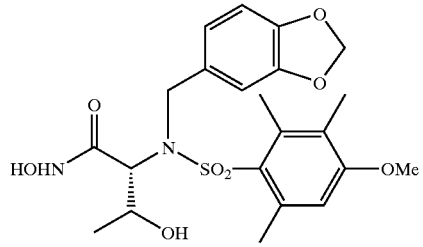

Step 1

To a suspension of D-threonine (7.87 g, 66.1 mmol) in acetonitrile (100 mL) was added trimethylsilyl cyanide (40 mL, 298 mmol) and the resulting solution was heated to 80° C. After 1 h, 4-methoxy-2,3,6-trimethylbenzenesulfonyl chloride (17.3 g, 69.4 mmol) was added and the heating was continued. After 12 h, the reaction mixture was cooled to room temperature. Methanol (15 mL) was added, and the organics were removed in vacuo. The residue was diluted with diethyl ether (300 mL) and after cooling the reaction mixture to 0° C., the pH was adjusted to 8 with 6 N aqueous sodium hydroxide solution. The organic layer was collected and the aqueous layer was extracted with diethyl ether. The aqueous layer was adjusted to pH 4 and again extracted with ethyl acetate. The combined organic extracts were dried over magnesium sulfate and concentrated to afford 2(R)-(4-methoxy-2,3,6-trimethylbenzenesulfonylamino)-3(S)-hydroxybutyric acid (22 g) as a brown foam which was used without further purification.

Step 2

To a solution of 2(R)-(4-methoxy-2,3,6-trimethylbenzenesulfonylamino)-3(S)-hydroxybutyric acid (29.13 g, 87.9 mmol) in dimethylformamide (280 mL) at 0° C., was added potassium carbonate (72.9 g, 527 mmol) and a solution of 3,4-methylenedioxybenzyl chloride ((60 g, 170.8 mmol, 50% (w/w)) in methylene chloride. After 2 h, lithium iodide (5.88 g, 44 mmol) was added and the reaction mixture was warmed to rt. over 2 h. After 6 h, the reaction mixture was partitioned between ethyl acetate (600 mL) and water (250 mL). The organic layer was separated, dried over magnesium sulfate and concentrated in vacuo. The crude residue was chromatographed (300 g $SiO_2$, 15% ethyl acetate-hexanes) to afford 2(R)-(4-methoxy-2,3,6-trimethylbenzenesulfonylamino)-3(S)-hydroxybutyric acid 3,4-methylenedioxybenzyl ester (40.4 g), a portion which was taken directly into the next reaction without further purification.

Step 3

2(R)-(4-methoxy-2,3,6-trimethylbenzenesulfonylamino)-3(S)-hydroxybutyric acid 3,4-methylenedioxybenzyl ester (10.9 g, 23.41 mmol) and imidazole (2.07 g, 30.43 mmol was dissolved in tetrahydrofuran (28 mL). The reaction mixture was cooled to 0° C. and 1 M triethylsilyl chloride in tetrahydrofuran (28 mL, 28 mmol) was added. After 1 h, the reaction mixture was concentrated and chromatographed over a Biotage 40L column (eluted with 10% ethyl acetate-hexanes) to afford 2(R)-(4-methoxy-2,3,6-trimethylbenzenesulfonyl-amino)-3(S)-(triethylsilyloxy) butyric acid 3,4-methylenedioxybenzyl ester (13.5 g).

Step 4

To a solution of 2(R)-(4-methoxy-2,3,6-trimethylbenzenesulfonyl-amino)-3(S)-(triethylsilyloxy) butyric acid 3,4-methylenedioxybenzyl ester (3.3 g, 5.7 mmol) in benzene (100 mL) at 0° C. was added 3,4-methylenedioxyphenyl methanol (1.3 g, 8.5 mmol), tri-n-butylphosphine (2.1 mL, 8.5 mmol), followed by 1,1'-[azodicarbonyl]dipiperidine (2.2 g, 8.5 mmol). The reaction mixture was allowed to warm to room temperature over 4 h. After 72 h, the reaction mixture was diluted with an equal volume of hexanes, cooled to 0° C. for 2 h and filtered. The residue was concentrated and chromatographed (300 g SiO$_2$, 15% ethyl acetate-hexanes) to afford 2(R)-[(3,4-methylenedioxybenzyl)-(4-methoxy-2,3,6-trimethylbenzenesulfonyl)amino]-3(S)-(triethylsilyloxy) butyric acid 3,4-methylenedioxybenzyl ester (3.3 g) as a yellow oil.

Step 5

To a solution of 2(R)-[(3,4-methylenedioxybenzyl)-(4-methoxy-2,3,6-trimethylbenzenesulfonyl)amino]-3(S)-(triethylsilyloxy)butyric acid 3,4-methylenedioxybenzyl ester (3.3 g, 4.62 mmol) in argon deoxygenated 80% ethanol-tetrahydrofuran (100 mL) was added 10% Pd—C (2 g) and the resulting reaction mixture was hydrogenated at atmospheric pressure for 45 min. The reaction mixture was degassed under argon, the slurry was filtered over Celite, and the Celite pad was washed with ample 80% ethanol-methylene chloride. The filtrate was concentrated and azeotroped with tetrahydrofuran (200 mL) and the residue was dissolved in dimethylformamide (25 mL). O-Benzyl hydroxylamine (2.0 g, 16.2 mmol), HOBT (0.71 g, 5.2 mmol), and EDAC (3.1 g, 16.2 mmol) were added and the reaction mixture was stirred for 16 h. The reaction mixture was diluted with ethyl acetate and was washed with 2.4 N aqueous hydrochloric acid and saturated aqueous sodium bicarbonate. The mixture was then dried over magnesium sulfate and concentrated in vacuo to afford crude N-benzyloxy-2(R)-[(3,4-methylenedioxy-benzyl)-(4-methoxy-2,3,6-trimethylbenzenesulfonyl)amino]-3(S)-hydroxybutyramide (1.25 g) which was taken directly into the next reaction without further purification.

Step 6

To a solution of N-benzyloxy-2(R)-[(3,4-methylenedioxybenzyl)-(4-methoxy-2,3,6-trimethylbenzenesulfonyl)amino]-3(S)-hydroxybutyramide (1.25 g, 2.19 mmol) in argon deoxygenated 80% ethanol-tetrahydrofuran (100 mL) was added 10% Pd—C (0.7 g), and the resulting mixture was hydrogenated at atmospheric pressure for 60 min. The reaction mixture was degassed under argon and the slurry was filtered over Celite. The Celite cake was washed with ample 80% ethanol-methylene chloride and the filtrate was concentrated to almost dryness. The mixture was dissolved in 4 mL of ethyl acetate which was added slowly dropwise to 100 mL of vigorously stirring hexanes. The slurry was filtered to afford N-hydroxy-2(R)-[(3,4-methylenedioxybenzyl)-(4-methoxy-2,3,6-trimethylbenzenesulfonyl)amino]-3(S)-hydroxybutyramide (0.67 g) as a white solid.

Example 15

N-hydroxy-2(R)-[(1H-benzimidazole-5-ylmethyl)(4-methoxy-2,3,6-trimethylbenzenesulfonyl)amino]-3 (R)-hydroxybutyramide (Table I, Cmpd. 136)

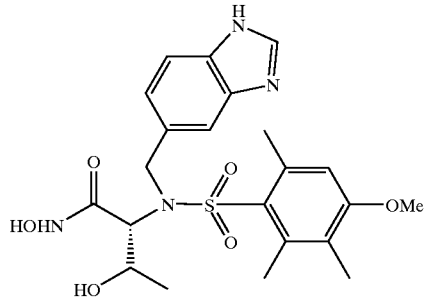

Step 1

The conditions for the esterification of N-carbobenzyloxy-D-threonine with N,N'-diisopropyl-O-tert-butylisourea to provide O-tert-butyl-N-carbobenzyloxy-D-threonine are the same as those described in Example 12, step 1 above.

Step 2

To a mixture of O-tert-butyl-N-carbobenzyloxy-D-threonine (2.74 g, 8.86 mmol), triethylamine (1.9 ml, 13.29 mmol) and 4-dimethylaminopyridine (50 mg) in dry dimethylformamide (20 ml) was added tert-butyldimethylsilyl chloride (1.47 g, 9.8 mmol). The mixture was stirred overnight under argon atmosphere. Additional triethylamine (1 ml) and tert-butyldimethsilyl chloride (500 mg) were added, and the mixture was heated at 80° C. for six hours. The material was cooled to ambient temperature and condensed on the rotary evaporator. The residue was taken up in methylene chloride (80 ml) and partitioned with an equal volume of brine. The organic phase was collected and the aqueous phase was back extracted with methylene chloride (2×80 ml). The methylene chloride phases were combined, dried with magnesium sulfate and condensed. The residue was purified by chromatography (flash silica gel, 15% ethyl acetate-hexanes) to provide O-tert-butyl-N-carbobenzyloxy-β-O-tert-butyldimethylsilyl-D-threonine (3.27 g) as a clear viscous oil.

Step 3

To a solution of O-tert-butyl-N-carbobenzyloxy-β-O-tertbutyldimethylsilyl-D-threonine (3.26 g, 7.7 mmol) in a 3:1 mixture of ethanol/tetrahydrofuran (30 ml) was added 10% palladium on charcoal (80 mg). The mixture was placed under a hydrogen balloon and stirred for 1.5 hours. The material was filtered through a short plug of celite and rinsed with ethanol (200 ml). The filtrate was condensed on the rotary evaporator providing α-O-tert-butyl-β-O-tertbutyldimethylsilyl-D-threonine (2.2 g) as a clear viscous oil.

Step 4

To a stirred solution (α-O-tert-butyl-(β-O-tertbutyldimethylsilyl-D-threonine (2.15 g, 7.65 mmol) in dry acetonitrile (30 ml) was added trimethylsilylcyanide (2.9 ml, 22.9 mmol). After five minutes 2,3,6-trimethyl-4-methoxybenzenesulfonyl chloride (2.02 g, 8.1 mmol) was added and the mixture was stirred for two hours. Ethyl acetate (80 ml) was added and the material was partitioned with an equal volume of aqueous 1.5% hydrochloric acid. The organic phase was collected and shaken with an equal volume of brine. The ethyl acetate phase was isolated and the aqueous phases were back extracted with ethyl acetate (2×80 ml). The organic phases were combined, dried with magnesium sulafate and condensed to provide tert-butyl-2 (R)-(4-methoxy-2,3,6-trimethylbenzenesulfonyl)amino]-3-[(R)-tert-butyldimethylsilyloxy]-butyrate (3.85 g) as a foamy semi-solid material.

Step 5

To a solution of tert-butyl-2(R)-(4-methoxy-2,3,6-trimethylbenzenesulfonyl)amino]-3-[(R)-tert-butyldimethylsilyloxy]-butyrate (3.83 g, 7.63 mmol) and 3-nitro-4-(N-phthaloyl)benzyl bromide (3.03 g, 8.4 mmol) in dry dimethylformamide (30 ml) was added potassium carbonate (1.7 g, 12.3 mmol) (Note: the synthesis for 3-nitro-4(N-phthaloyl)benzyl bromide is shown below in Step 5A). The mixture was stirred for 12 hours and additional 3-nitro-4-(N-phthaloyl)benzyl bromide (1.0 g) was added. After another 6 hours the mixture was condensed on the rotary evaporator. Purification by chromatography (silica gel, 10% to 15% ethyl acetate-hexanes) provided tert-butyl-2(R)-[(3-nitro-4-(N-phthalamido)benzyl)-(4-methoxy-2,3,6-trimethylbenzenesulfonyl)amino)]-3-[(R)-tert-butyldimethylsilyloxy]-butyrate as a white powder (4.36 g).

Step 5A

Preparation of 3-nitro-4-(aminophthaloyl)benzyl bromide:

To a cooled (ice bath) solution of 3-nitro-4-(aminophthaloyl)benzyl alcohol (5.94 g, 19.92 mmol) [the synthesis of this alcohol was described in example 10, steps 2 & 3] and triphenylphosphine (7.83 g, 29.9 mmol) in dry methlylene chloride (90 ml) was added carbon tetrabromide (9.92 g, 29.9 mmol). The mixture was stirred for 1 hour at 0° C. and then warmed to ambient temperature over 1 hour. The entire mixture was then loaded onto a flash silica gel column, eluting with 30% ethyl acetate-hexanes to provide 3-nitro-4-(aminophthaloyl)benzyl bromide as a yellow-white powder (5.03 g).

Step 6

The conditions for the reduction of tert-butyl-2(R)-[(3-nitro-4-(N-phthalamido)benzyl)-(4-methoxy-2,3,6-trimethylbenzenesulfonyl)amino))]-3-[(R)-tert-butyldimethylsilyloxy]-butyrate to provide tert-butyl-2(R)-[(3-amino-4-(N-phthalamido)benzyl)-(4-methoxy-2,3,6-trimethylbenzenesulfonyl)amino))]-3-[(R)-tert-butyldimethylsilyloxy]-butyrate are the same as those described in Example 10, step 5 above.

Step 7

The conditions for the de-pthaloylation of tert-butyl-2(R)-[(3-amino-4-(N-phthalamido)benzyl)-(4-methoxy-2,3,6-trimethylbenzenesulfonyl)amino))]-3-[(R)-tert-butyldimethylsilyloxy]-butyrate to provide tert-butyl-2(R)-[3,4-diamino-benzyl)-(4-methoxy-2,3,6-trimethylbenzenesulfonyl)amino))]-3-[(R)-tert-butyldimethylsilyloxy]-butyrate are similar to those described in Example 10, step 6 above.

Step 8

The conditions for the clay catalyzed conversion of tert-butyl-2(R)-[3,4-diamino-benzyl)-(4-methoxy-2,3,6-trimethylbenzenesulfonyl)amino))]-3-[(R)-tert-butyldimethylsilyloxy]-butyrate to provide tert-butyl-2(R)-[benzimidazol-5-yl-methyl)-(4-methoxy-2,3,6-trimethylbenzenesulfonyl)amino))]-3-[(R)-tert-butyldimethylsilyloxy]-butyrate are similar to those described in Example 10, step 7 above.

Step 9

To a cooled (ice bath) flask containing neat tert-butyl 2 (R)-[benzimidazol-5-yl-methyl)-(4-methoxy-2,3,6-trimethylbenzenesulfonyl)amino))]-3-[(R)-tert-butyldimethylsilyloxy]-butyrate(2.53 g, 4.0 mmol), under argon was added a 1.0 M solution of tetra-N-butylammonium fluoride (16 ml) via syringe. The mixture was stirred for 15 minutes at 0° C. and then warmed to ambient temperature. After 30 minutes additional tetra-N-butylammonium fluoride (5 ml) was added and stirring continued for 2 hours. To the mixture was added a saturated solution of aqueous ammonium chloride (80 ml) followed by ethyl acetate (60 ml). The material was partitioned and the organic phase collected and washed subsequently with three equal volumes of brine solution. The aqueous phases were back extracted with ethyl acetate (2×80 ml). The organic phases were combined, dried with magnesium sulfate and condensed. The residue was purified by chromatography (silica gel, ethyl acetate 100% as eluant) providing tert-butyl-2(R)-[benzimidazol-5-yl-methyl)-(4-methoxy-2,3,6-trimethylbenzenesulfonyl)amino)]-3(R)-hydroxy-butyrate as a viscous clear oil.

Step 10

Tert-butyl-2(R)-[benzimidazol-5-yl-methyl)-(4-methoxy-2,3,6-trimethylbenzenesulfonyl)amino))]-3(R)-hydroxy-butyrate was converted to 2(R)-[benzimidazol-5-yl-methyl)-(4-methoxy-2,3,6-trimethylbenzenesulfonyl)amino)]-3(R)-hydroxy-butyric acid by following the procedure described in Example 10, step 8 above.

Step 11

2(R)-[benzimidazol-5-yl-methyl)-(4-methoxy-2,3,6-trimethylbenzenesulfonyl)amino)]-3(R)-hydroxy-butyric acid was then converted to N-hydroxy-2(R)-[benzimidazol-5-yl-methyl)-(4-methoxy-2,3,6-trimethylbenzenesulfonyl) amino)]-3(R)-hydroxybutyamide by following the procedure as described in Example 3, steps 6 and 7 above.

Example 16

Synthesis of Compounds of the Following Formula, as Shown in Scheme E

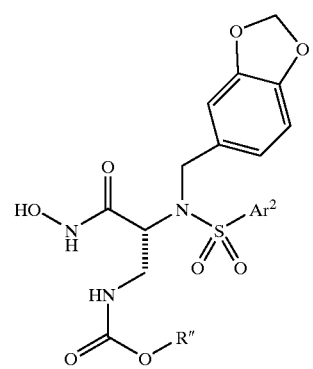

Step 1

To ArgoGel-OH (formula 1) in a empty solid phase extraction vial, fitted with a stopcock is added 3 eq. of a compound of formula 2 (Fmoc-D-Dpr(BOC)), 3 eq. of diisopropylcarbodiimide (DIC), and 0.05 eq. of a 0.116 M solution of dimethylaminopyridine (DMAP) in THF. Sufficient $CH_2Cl_2$ is added to swell the resin (~12.5 mL/gr of resin). The reaction is then placed on a spinner and rotated overnight. The reaction is then filtered by suction filtration and washed 3 times with $CH_2Cl_2$, 3 times with MeOH, once with 1:1 $HOAc/CH_2Cl_2$, 3 times with MeOH and then lastly 3 times with $CH_2Cl_2$ and dried to give a resin AG-D-Dpr (BOC)-Fmoc.

The resulting resin (AG-D-Dpr(BOC)-Fmoc) is treated with a solution of 20% piperidine in DMF (pip/DMF) for 20 min. The reaction is then filtered by suction filtration and washed 3 times with CH₂Cl₂, 3 times with MeOH, once with 1:1 HOAc/CH₂Cl₂, 3 times with MeOH and then lastly 3 times with CH₂Cl₂. To give a resin of formula 3 (AG-D-Dpr(BOC)—NH₂).

Step 2

To a resin of formula 3 (AG-D-Dpr(BOC)—NH₂) is added sufficient CH₂Cl₂ to swell the resin (~12.5 mL/gr of resin). Then 3 eq. of a sulfonyl chloride of formula 4 (Ar²SO₂Cl) and 3 eq. of triethylamine (TEA) are added. The reaction is then placed on a spinner and rotated overnight. The reaction is then filtered by suction filtration and washed 3 times with CH₂Cl₂, 3 times with MeOH, once with 1:1 HOAc/CH₂Cl₂, 3 times with MeOH and then lastly 3 times with CH₂Cl₂ to give a resin of formula 5 (AG-D-Dpr(BOC)-NHSO₂Ar²).

Step 3

To the resin of formula 5 (AG-D-Dpr(BOC)-NHSO₂Ar²) is added sufficient 1:1 toluene/CH₂Cl₂ to swell the resin (~12.5 mL/gr of resin). Then 10 eq. of 1,1'-(azodicarbonyl)dipiperidine (ADDP), 10 eq. of Bu₃P, followed by 10 eq. of piperonyl alcohol (ROH) are added. The reaction is then placed on a spinner and rotated overnight. The reaction is then filtered by suction filtration and washed 3 times with CH₂Cl₂, 3 times with MeOH, once with 1:1 HOAc/CH₂Cl₂, 3 times with MeOH and then lastly 3 times with CH₂Cl₂ to give a resin of formula 6 (AG-D-Dpr(BOC)-NRSO₂Ar²).

Step 4

The resin of formula 6 (AG-D-Dpr(BOC)-NRSO₂Ar²) is treated with a solution of 1M chlorotrimethylsilane in 3M phenol/CH₂Cl₂ for 30 minutes. The reaction is then filtered by suction filtration and washed 3 times with CH₂Cl₂, 3 times with MeOH, once with 1:1 HOAc/CH₂Cl₂, 3 times with MeOH and then lastly 3 times with CH₂Cl₂ to give a resin of formula 7 (AG-D-Dpr—NRSO₂Ar²).

Step 5

To a resin of formula 7 (AG-D-Dpr—NRSO₂Ar²) is added 3 eq. of a succinimidylcarbonate of formula 8 (R"OCO₂Su), 3 eq. Et₃N (TEA) and 0.05 eq. of a 0.116 M solution of 4-dimethylaminopyridine (DMAP) in THF. Sufficient CH₂Cl₂ is added to swell the resin (~12.5 mL/gr of resin). The reaction is then placed on a spinner and rotated overnight. The reaction is then filtered by suction filtration and washed 3 times with CH₂Cl₂, 3 times with MeOH, once with 1:1 HOAc/CH₂Cl₂, 3 times with MeOH and then lastly 3 times with CH₂Cl₂ to give a resin of formula 9 (AG-D-Dpr(COOR")-NRSO₂Ar²).

Step 6

A resin of formula 9 (AG-D-Dpr(COOR")-NRSO₂Ar²) is first washed with THF. Sufficient THF is added to swell the resin (~12.5 mL/gr of resin). Then 25 eq. of 50% aq. NH₂OH is added and the reaction is rotated for two days. The reaction is then filtered by suction filtration and washed with CH₂Cl₂, MeOH, and then CH₂Cl₂. The filtrate is concentrated on a Speed Vac to obtain a compound of formula 10 (HONH-Dpr(COOR")NRSO₂Ar²), which is purified by RP-HPLC.

Using the appropriate sulfonyl chloride of formula 4 and the appropriate succinimidylcarbonate of formula 8, the following compounds of Table I were made:

Compound 139, Compound 140, Compound 141, Compound 146, Compound 148, and Compound 149.

Example 17

Synthesis of Compounds of the Following Formula, as Shown in Scheme F

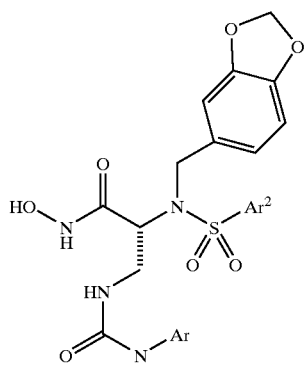

Step 1

A resin of formula 7 (AG-D-Dpr—NRSO₂Ar²) is first washed with THF, then 15 eq. of the isocyanate of formula 8 (ArNCO) is added. Sufficient THF is added to swell the resin (~12.5 mL/gr of resin). The reaction is then placed on a spinner and rotated overnight. The reaction is then filtered by suction filtration and washed 3 times with CH₂Cl₂, 3 times with MeOH, once with 1:1 HOAc/CH₂Cl₂, 3 times with MeOH and then lastly 3 times with CH₂Cl₂ to give a resin of formula 9 (AG-D-Dpr(CONHAr)-NRSO₂Ar²).

Step 2

A resin of formula 9 (AG-D-Dpr(CONHAr)-NRSO₂Ar²) is first washed with THF. Sufficient THF is added to swell the resin (~12.5 mL/gr of resin) then 25 eq. of 50% aq. NH₂OH is added and the reaction is rotated for two days. The reaction is then filtered by suction filtration and washed with CH₂Cl₂, MeOH, and then CH₂Cl₂. The filtrate is concentrated on a Speed Vac to obtain a compound of formula 10 (HONH-Dpr(CONHAr)NRSO₂Ar²), which is purified by RP-HPLC.

Using the appropriate isocyanate of formula 8 the following compound of Table I was made:

Compound 147.

Example 18

Formulation Examples

The following are representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Liposomal Formulation

The following ingredients are mixed to form a liposomal formulation.

| Ingredient | Amount |
| --- | --- |
| compound of this invention | 10 mg |
| L-α-phosphatidylcholine | 150 mg |
| tert-butanol | 4 ml |

Freeze dry the sample and lyopholize overnight. Reconstitute the sample with 1 ml 0.9% saline solution. Liposome size can be reduced by sonication.

Example 19

Isolation and Preparation of Procollagen C-Proteinase

Cloning of Human PCP and Construction of the HT-1080 Vector

Human Procollagen C-Proteinase (PCP, also known as Bone Morphogenetic Protein-1 or BMP-1) was cloned from a human fibroblast cDNA library (Stratagene, San Diego, Calif.). Cloning was performed by PCR based on the reported nucleotide sequence (Wozney, J. M., Rosen, V., Celeste, A. J., Mitsock, L. M., Whitters, M. J., Kriz, R. W., Hewick, R. M., and Wang, E. A. (1989) direct GenBank submission accession M22488, locus HUMBMP1) using Taq polymerase, the 5' primer GCGCGCGGTACCCGC-CCCGCCAGCATGCCCGGCGTGGCCCGC-CTGCCGCTGCTGC TCGGGCTGCTGCTGCTC-CCGCGTCCCGGCCGGCCGCTGGACTTGGCCGACT ACAC CTATGACCTGGC (SEQ ID NO:1) (Oligo Therapeutics, Inc., Wilsonville, Oreg.), and the 3' reverse strand primer CCGCTCGAGCCTCACTGGGGGGTCCG-GTTTCTTTTCTGCACTCGGAATTTGAGCTG GTG (SEQ ID NO:2) (Gibco) to yield the entire full-length nucleotide encoding the signal sequence, propeptide, catalytic domain, and all C-terminal domains to the natural translation termination site. The PCR product was purified by gel electrophoresis using the Wizard DNA Purification Kit (Promega, Madison, Wis.) and ligated directly into the mammalian expression vector pCR3.1 (Invitrogen, Carlsbad, Calif.) by the TA cloning method. Ligated product was used to transform E coli strain TOP10F' (Invitrogen, Carlsbad, Calif.) by a standard heat-shock method, and transformants were selected by restriction analysis of purified plasmid using the enzymes HindIII and BamHI. Transformants testing positive for the PCP insert were submitted for sequencing using the Perkin-Elmer/ABI system. Two clones were selected that, when combined, encoded the entire amino acid sequence identical to the one predicted by Wozney et al. The two clones were recombined by restriction using the enzymes BbrI, which cleaved at a naturally occurring internal site, and EcoRV, which cleaved at the junction of the insert and vector. The excised fragments were religated into EcoRV-treated pCR3.1. The resulting construct contained the entire coding sequence identical to that reported by Wozney et al. with the exception of two silent mutations in the signal sequence, G->A at both positions 39 and 45 counting from the translation initiation site (ATG). The completed plasmid construct was amplified in E. coli DH5a and purified using anion exchange chromatography (MaxiPrep columns from Qiagen (Valencia, Calif.) catalog #12162).

Transfection of HT-1080 and Selection of the PCP-Expressing Clone

The human fibrosarcoma line HT-1080 (ATCC) was grown in high glucose DEEM (DMEM-HG) supplemented with 10% heat-inactivated fetal bovine serum (HI-FBS) in 100 mm culture dishes (Falcon, Becton Dickenson, Franklin, N.J.) and transfected with 2 μg of purified plasmid using the standard method for Lipofectamine (Gibco, Bethesda, Md.) in serum free medium. Stable transfectants were selected by treating the plated culture with 400 μg/ml G418 (Gibco). After selection for 10 days, the adherent single colonies were picked from the plate, replated in 12-well plates and grown until confluent. Individual stable colonies were screened for PCP expression by TaqMan (Perkin-Elmer, Foster City, Calif.) analysis using equivalent amounts of total RNA, the 5' primer GACGAAGAGGAC-CTGAGGGCCTT (SEQ ID NO:3) (Perkin-Elmer, Foster City, Calif.), the 3' reverse strand primer TTCCTGGAACT-GCAGCTTTGA (SEQ ID NO:4) (Perkin-Elmer, Foster City, Calif.), and the reverse strand probe TGCCGTCT-GAGATCCACAGCCTGCT (SEQ ID NO:5) (Perkin-Elmer). A stable line, HT-1080/hPCP-23, was chosen based on the highest PCP mRNA expression level in the TaqMan screen. Stocks of the HT-1080/hPCP-23 stable line were transferred to DMEM-HG supplemented with 5% HI-FBS and 10% DMSO (no G 418 added) and were slowly frozen at −70° C. overnight, then transferred to a liquid nitrogen bath for long-term storage. Revitalized HT-1080/hPCP-23 were maintained in DMEM-HG supplemented with 10% HI-FBS and 250 μg/ml G418 for no more than 7 passages. Expression of PCP for harvest was carried out by replating and growing HT-1080/hPCP-23 on rat tail type I collagen-coated plates (Falcon) in OptiMEM (Gibco) serum free medium without G418 for 24 hr.

Production of PCP in HT1080 Cells

The HT1080 cells that were transformed to produce PCP were adapted to grow in suspension in optiMEM medium (GIBCO) supplemented with 5% fetal bovine serum and 4 ml/L G418 (GIBCO). The culture was maintained at 37 C. and the dissolved oxygen at 30%. Typically batch sizes of 10 liters were produced. When the cell density reached $4-6 \times 10^5$ cells/ml, the culture fluid was collected and filtered through 0.2 μm membranes. Alternatively, the cell culture was perfused with fresh media at the rate of 0.8 to 1.0 culture volume/day. The density of the perfused cultures reached $1-2.5 \times 10^6$ cells/ml and were maintained up to two weeks with continuous harvests.

Purification of PCP from HT1080 Cells

A column packed with Dyematrex Gel Green A (Millipore, Bedford, Mass.) was equilibrated against 50 mM HEPES, pH7.2, containing 6 mM $CaCl_2$ and 0.3M NaCl. After the HT1080 cell culture fluid was loaded, the column was washed with 10 column volumes of the equilibration buffer containing 1.0 M NaCl. PCP was eluted with 50 mM HEPES pH 7.2 containing 3 M NaCl, 2 M urea and 6 mM $CaCl_2$. Eluate fractions were pooled and concentrated to 150–200 ml and dialyzed against 4.0 liters of 50 mM HEPES, 6 mM $CaCl_2$, pH 7.2 overnight. The material was then centrifuged at 5,000 g for 15 minutes to remove precipitates. The PCP containing sample were stored at −20° C. until ready for further processing.

The PCP containing sample was thawed and diluted with 50 mM HEPES pH 7.2 containing 6 mM $CaCl_2$, if necessary to bring the NaCl concentration to 0.1–0.15 M. The pH was adjusted to 6.7 with 2 N HCl. The protein solution was filtered through a 0.45 μm filter to remove any precipitate. This preparation was then loaded onto a column packed with Q-Sepharose High Performance (Pharmacia, Piscataway, N.J.) which had been equilibrated with 50 mM HEPES pH 6.7 containing 6 mM $CaCl_2$ and 0.15 M NaCl. The PCP was not retained in the column and was therefore in the flow through fractions. The PCP was concentrated to 1 mg/ml and used for screening.

Production of PCP in Drosophila Cells

Drosophila cells which had been transformed to produce PCP were grown in bioreactors at a typical batch volume of 10 liters in SF900 II SF medium (GIBCO). The temperature was maintained at 30° C. and the dissolved oxygen at 30%. Periodically the cells were fed a cocktail consisting of glutamine, lipids and yeastolate. When cell densities reached $30-50 \times 10^6$ cells/ml, supernatants were harvested by centrifugation and concentrated by ultrafiltration using a 30 Kd membrane.

Purification of PCP from Culture Fluid from Drosophila Cells

Culture fluid from the drosophila cells was concentrated 8 fold and the pH adjusted to 7.1–7.2 if necessary. The culture fluid was centrifuged at 3000 g for 10 minutes and filtered through 0.45 μm filters. The culture fluid was then loaded onto columns packed with carboxy-sulfone packing material (J. T. Baker/Mallinckrodt, Phillipsburg, N.J.) which had been equilibrated with 0.1 M NaCl, 50 mM HEPES, 6 mM $CaCl_2$, pH 7.2. After being loaded, the column was washed with 10 column volumes of the equilibration buffer. Retained proteins were eluted with a gradient of 0.1 to 1.0 M NaCl in 9 column volumes. Fractions that had PCP activity were pooled for further purification.

The PCP eluted off the carboxy-sulfone column was loaded onto a Dyematrex Gel Green A (Millipore, Bedford, Mass.) column that had been equilibrated with 50 mM HEPES, pH 7.4 containing 0.3 M NaCl and 6 mM $CaCl_2$. The column was then washed with the equilibration buffer containing 1 M NaCl. Retained proteins were eluted with 50 mM HEPES, pH 7.4, 3 M NaCl, 2 M urea, 6 mM $CaCl_2$. The elution peak was concentrated and dialyzed against 50 mM HEPES, pH 7.4 containing 0.3 M NaCl, 6 mM $CaCl_2$. The preparation was centrifuged at 3000 g for 10 minutes. Brij 35 (Sigma, Madison, Wis.) was added to the supernatant to a final concentration of 0.02%. This preparation was used for screening.

Example 20

Isolation of Collagenase Enzymes

The catalytic domain of human collagenase-1 was expressed as a fusion protein with ubiquitin in *E. Coli* as described in Gehring, E. R. et al., *J. Biol. Chem.*, 270, 22507, (1995). After purification of the fusion protein, the collagenase-1 catalytic domain was released by treatment with 1 mM of aminophenylmercuric acetate (APMA) for 1 hour at 37° C. and then purified by zinc chelate chromatography.

Human collagenase-2 and gelatinase B were isolated in active form from buffy coats as described in Mookhtiar, K. A. et al., *Biochemistry*, 29, 10620, (1990).

The propeptide and catalytic domain portion of human collagenase-3 was expressed in *E. Coli* as an N-terminal fusion protein with ubiquitin. After purification, the catalytic domain was released by treatment with 1 mM APMA for 1 hour at 37° C., and then purified by zinc chelate chromatography.

Rat collagenase-3 was purified in active form from the culture media of uterine smooth muscle cells as described in Roswit, W. T. et al., *Arch. Biochem. Biophys.*, 225, 285–295 (1983).

Example 21

Inhibition of Procollagen C-Proteinase Activity

The ability of the compounds to inhibit PCP has been demonstrated in the following in vitro assays utilizing a synthetic peptide as the substrate.

Assay A

A continuous assay was performed using 20 μM substrate (Dabcyl-Pro-Tyr-Tyr-Gly-Asp-Glu-Pro-n-Leu-Edans) (SEQ ID NO:6). The final assay conditions were 20 μM substrate, 50 mM HEPES pH 7.5, 50 mM NaCl, 3% DMSO, 30° C. and PCP enzyme. Product formation was monitored by fluorescence spectroscopy, Ex.=335 nm, Em.=490 nm. The $IC_{50}$ was calculated from the dose response of the compounds.

Assay B

Eighty μL of buffer A (20 mM HEPES) containing the desired concentrations of the test compound in DMSO or carrier vehicle was mixed with 10 μL of approx. 1 mg/mL PCP enzyme and 10 μL of 0.1 mM substrate both in 20 mM HEPES. The contents are mixed, incubated at room temperature for 1–2 hours and fluorescent readings taken with a Victor plate reader (Ex. 405 nm, Em. 460 nM at 2000–40, 000 lamp energy, 0.1–1 sec/well). The substrate was DACM-Cys-Pro-Tyr-Gly-Asp-Glu-Pro-nLeu-Lys-FITC-OH. (SEQ ID NO:7) (DACM=dimethylaminocoumarylmaleimide, FITC=fluorescein isothiocyanate). The $IC_{50}$ was calculated from plots of the initial velocity vs. compound concentration.

Additional in vitro assays using native procollagen as the substrate may also be used and these assays are described in more detail in WO 97/05865 ("C-Proteinase Inhibitors for the Treatment of Disorders Relating to the Overproduction of Collagen"), published Feb. 20, 1997.

The compounds in Table I had $IC_{50}$'s in the range of 0.01 to 2 μM.

Example 22

Measurement of Collagenase Activity

The collagenase-1, collagenase-2 and collagenase-3 inhibitory activity of compounds of this invention in vitro was determined based on the hydrolysis of MCA-Pro-Leu-Gly-Leu-DPA-Ala-Arg-$NH_2$ (SEQ ID NO:8) (Bachem, Inc.) at 37° C. as described in Knight, C. G., et al., *FEBS Lett.*, 296(3): 263–266 (1992).

The collagenase enzyme was diluted with assay buffer (50 mM Tricine pH 7.5, 200 mM NaCl, 10 mM $CaCl_2$, and 0.005% Brij-35) containing 10 μmole of above substrate dissolved in DMSO. Compounds of the invention dissolved in DMSO or only DMSO (control samples) were added such that the final DMSO concentration in all assays was 2.5%. The fluorescence changes were monitored with a Perkin-Elmer LS-50B flourimeter using an excitation wavelength of 328 nm and an emission wavelength of 393 nm.

Selected compounds from Tables I were 100–1000 more selective for PCP inhibition than for the collagenase-1 and collagenase-3 enzymes and 50–500 more selective for PCP inhibition than for the collagenase-1 and collagenase-2 enzymes.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound selected from the compounds of Formula (I):

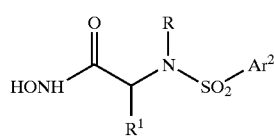

wherein:

$R^1$ is alkyl, haloalkyl, cycloalkyl, optionally substituted aryl, aralkyl, aralkenyl, heteroaryl, heteroaralkyl, heteroaralkenyl, heterocyclylalkyl, cycloalkylalkyl, or —C(=NR')$NHSO_2R''$ (where R' is hydrogen or alkyl, and R" is alkyl, haloalkyl, cycloalkyl, cycloalkylalkyl, optionally substituted, aryl, aralkyl, heteroaryl, heteroaralkyl, heterocyclylalkyl), —$CH_2CO_2CH_3$, hydroxymethyl, 2-hydroxyethyl, tert-butoxymethyl, —$CH_2NHCOPh$, methoxymethyl, —$CHNHSO_2Ph$, 2-[4-(benzyloxy-carbonyl)-piperazin-1-yl-carbonyl]-ethyl, 2-(pyridin-3-yl-methylamino-carbonyl]-ethyl, 2-[4-phenyl-piperazin-1-yl-carbonyl]-ethyl, 2-[4-methoxy-carbonyl)-piperazin-1-yl-carbonyl]-ethyl, 2-[4-acetyl-piperazin-1-yl-carbonyl]-ethyl, 2-[4-(ethoxy-carbonyl)-piperazin-1-yl-carbonyl]-ethyl, 2-[1-(ethoxy-carbonyl)-piperidin-4-yl-aminocarbonyl]-ethyl, 2-(thiomorpholin-4-yl-carbonyl)-ethyl, 2-(benzylamino-carbonyl)-ethyl, 2-[4-(pyridin-2-yl)-piperazin-1-yl-carbonyl]-ethyl, 2-(4-pyridin-4-yl-methylamino-carbonyl)-ethyl, 2-(benzylamino-carbonyl)-ethyl, 2-(4-acetylpiperazin-1-yl-carbonyl)-ethyl, hydroxyethyl, 2-[4-(4-methylphenyl-aminocarbonyl)-piperazin-1-yl-carbonyl]-ethyl, 2-[4-(3-methoxyphenyl-aminocarbonyl)-piperazin-1-yl-carbonyl]-ethyl, 2-(N-methylethylamino-carbonyl)-ethyl, 2-[4-(phenoxymethyl-carbonyl)-piperazin-1-yl-carbonyl]-ethyl, methoxymethyl, 2-[4-(methanesulfonyl)-piperazin-1-yl-carbonyl-ethyl, 2-(cyclopropylamino-carbonyl)-ethyl, 4-(methoxycarbonyl)-phenyl-carbonylamino-methyl, 3-(benzyloxy-carbonylamino)-propyl, 2-(pyrrol-1-yl)-phenylcarbonyl-aminomethyl, 2-[(diphenyl)-methylaminocarbonyl]-ethyl, 3-cyanophenyl-aminocarbonyl-aminomethyl, thien-2-yl-carbonyl-aminomethyl, phenylcarbonyl-aminomethyl, $(C_4H_5)CHCH_3NHCO(C_2H_4)CONHCH_2$—, (4-methoxyphenyl)$COC_2H_4CONHCH_2$—, 4-chlorophenyl-sulfonylamino-carbonyl-aminomethyl, 5-(acetyl)-thien-2-yl-carbonyl-aminomethyl, pyridin-3-yl-carbonylamino-methyl, 2-[2-(methyl)-butyl-aminocarbonyl]-ethyl, (3,4,5-trimethoxyphenyl)$C_2H_4CONHCH_2$—, 3-methoxyphenyl-aminocarbonyl-aminomethyl, 2-[($C_6H_5$)$CHCH_3NHCO$]-ethyl, (phenoxy)$CH(CH_2CH_3)CONHCH_2$—, (3-nitrophenyl)$CH_2SO_2NHCH_2$—, 1-(ethoxycarbonyl)-piperidin-4-yl-aminomethyl-carbonylamino-methyl, 4-ethoxyphenyl-aminocarbonyl-aminomethyl, 2-chloropyridin-5-ylcarbonyl-aminomethyl, 2-[N,N(ethylcyano)(benzyl)-aminocarbonyl]-ethyl, 4-(methylthio)-phenylaminocarbonyl-aminomethyl, 2,4-difluorophenyl-carbonylamino-methyl, 2-propyl-2-[4-(phenylcarbonyl)-piperazin-1-ylcarbonyl]-ethyl, (4-hydroxyphenoxy)$CH(CH_3)CONHCH_2$—, 2-[4-(furan-2ylcarbonyl)-piperidin-1-ylcarbonyl]-ethyl, N-(3,5-(dimethoxy)phenylcarbonyl-aminomethyl, methylsulfonyl-aminomethyl, phenylsulfonyl-aminomethyl, acetylaminomethyl, methoxy-carbonyl-aminomethyl, 4-carboxyphenyl-carbonylamino-methyl, 4-methylbenzoate-carboxamido-methyl, (2-pyrrol-1-yl)-phenylcarbonyl, 4-(methoxy-carbonyl)-phenylcarbonyl-aminomethyl, (imidazol-4-yl)-methyl, N-(phenylcarbonyl)-aminomethyl), 2-chlorophenylmethoxy-carbonylamino-methyl, 3-nitrophenyl-methoxy-carbonylamino-methyl, 3,5-dichlorophenyl-methoxy-carbonylamino-methyl, 2-(pyrrol-1-yl)-benzamido-methyl, benzyloxy-carbonylamino-methyl, 4-methoxyaniline-carbonylamino-methyl, 4-nitrobenzyloxycarbonylamino-methyl, 2-bromobenzyloxy-carbonylamino-methyl, N-[4-(methoxycarbonyl)-phenylcarbonyl]-aminomethyl, N-(benzyloxycarbonyl)-aminopropyl, N-[2-(pyrrol-1-yl)-phenylcarbonyl]-aminomethyl, 2-[(diphenyl) methyl-aminocarbonyl]-ethyl, N-[3-(cyano)phenyl-aminocarbonyl]-aminomethyl, N-(thien-2-ylcarbonyl)-aminomethyl, N-(phenylcarbonyl)-aminomethyl, $(C_4H_5)CHCH_3NHCO(C_2H_4)CONHCH_2$—, $(4\text{methoxyphenyl})COC_2H_4CONHCH_2$—, N-(4-chlorophenylsulfonyl-aminocarbonyl)-aminomethyl, N-(5-(acetyl)thien-2-ylcarbonyl)-aminomethyl, N-(pyridin-3-ylcarbonyl)-aminomethyl, 2-[2-(methyl)-butyl-aminocarbonyl]-ethyl, (3,4,5-trimethoxyphenyl) $C_2H_4CONHCH_2$—, N-(3-(methoxy)phenyl-aminocarbonyl)-aminomethyl, 2-[$(C_6H_5)$ CHCH$_3$NHCO]-ethyl, (phenoxy)CH(CH$_2$CH$_3$) CONHCH$_2$—, (3-nitrophenyl)-CH$_2$SO$_2$NHCH$_2$—, N-[1-(ethoxycarbonyl)-piperidin-4-yl-aminomethyl-carbonyl]-aminomethyl, N-(4-(ethoxy)phenyl-aminocarbonyl)-aminomethyl, or N-(2-chloropyridin-5-ylcarbonyl)-aminomethyl;

R is —CH(R$^2$)Ar$^1$ or —CH(R$^2$)CH=CHAr$^1$ where R$^2$ is hydrogen or alkyl; and Ar$^1$ is optionally substituted aryl;

Ar$^2$ is 2,3,6-trimethoxy-4-methoxyphenyl; and their pharmaceutically acceptable salts, prodrugs, individual isomers, and mixtures of isomers.

2. The compound of claim 1 wherein R is —CH(R$^2$)Ar$^1$ wherein R$^2$ is hydrogen.

3. A compound selected from the compounds of Formula (I):

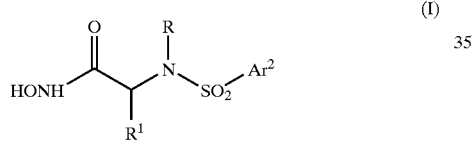

(I)

wherein:

R$^1$ is (alkylene)-C(O)—X where X is alkyl, haloalkyl, cycloalkyl, cycloalkylalkyl, amino, monosubstituted amino, disubstituted amino, optionally substituted aryl, aralkyl, heteroaryl, heteroaralkyl, heterocyclyl, heterocyclylalkyl, hydroxy, alkoxy, cycloalkoxy, cycloalkylalkoxy, heteroalkyloxy, aralkyloxy, or heteroaralkyloxy), or wherein —CH$_2$CO$_2$CH$_3$, hydroxymethyl, 2-hydroxyethyl, tert-butoxymethyl, —CH$_2$NHCOPh, methoxymethyl, —CHNHSO$_2$Ph, 2-[4-(benzyloxy-carbonyl)-piperazin-1-yl-carbonyl]-ethyl, 2-(pyridin-3-yl-methylamino-carbonyl)-ethyl, 2-[4-phenyl-piperazin-1-yl-carbonyl]-ethyl, 2-[4-methoxy-carbonyl]-piperazin-1-yl-carbonyl]-ethyl, 2-[4-acetyl-piperazin-1-yl-carbonyl]-ethyl, 2-[4-(ethoxy-carbonyl)-piperazin-1-yl-carbonyl]-ethyl, 2-[1-(ethoxy-carbonyl)-piperidin-4-yl-aminocarbonyl]-ethyl, 2-(thiomorpholin-4-yl-carbonyl)-ethyl, 2-(benzylamino-carbonyl)-ethyl, 2-[4-(pyridin-2-yl)-piperazin-1-yl-carbonyl]-ethyl, 2-(4-pyridin-4-yl-methylamino-carbonyl)-ethyl, 2-(benzylamino-carbonyl)-ethyl, 2-(4-acetylpiperazin-1-yl-carbonyl)-ethyl, hydroxyethyl, 2-[4-(4-methylphenyl-aminocarbonyl)-piperazin-1-yl-carbonyl]-ethyl, 2-[4-(3-methoxyphenyl-aminocarbonyl)-piperazin-1-yl-carbonyl]-ethyl, 2-(N-methylethylamino-carbonyl)-ethyl, 2-[4-(phenoxymethyl-carbonyl)-piperazin-1-yl-carbonyl]-ethyl, methoxymethyl, 2-[4-(methanesulfonyl)-piperazin-1-yl-carbonyl-ethyl, 2-(cyclopropylamino-carbonyl)-ethyl, 4-(methoxycarbonyl)-phenyl-carbonylamino-methyl, 3-(benzyloxy-carbonylamino)-propyl, 2-(pyrrol-1-yl)-phenylcarbonyl-aminomethyl, 2-[(diphenyl)-methylaminocarbonyl]-ethyl, 3-cyanophenyl-aminocarbonyl-aminomethyl, thien-2-yl-carbonyl-aminomethyl, phenylcarbonyl-aminomethyl, $(C_6H_5)CHCH_3NHCO(C_2H_4)CONHCH_2$—, $(4\text{-methoxyphenyl})COC_2H_4CONHCH_2$—, 4-chlorophenyl-sulfonylamino-carbonyl-aminomethyl, 5-(acetyl)-thien-2-yl-carbonyl-aminoethyl, pyridin-3-yl-carbonylamino-methyl, 2-[2-(methyl)-butyl-aminocarbonyl]-ethyl, (3,4,5-trimethoxyphenyl) $C_2H_4CONHCH_2$—, 3-methoxyphenyl-aminocarbonyl-aminomethyl, 2-[$(C_6H_5)$CHCH$_3$NHCO]-ethyl, (phenoxy)CH(CH$_2$CH$_3$)CONHCH$_2$—, (3-nitrophenyl) CH$_2$SO$_2$NHCH$_2$—, 1-(ethoxycarbonyl)-piperidin-4-yl-aminomethyl-carbonylamino-methyl, 4-ethoxyphenyl-aminocarbonyl-aminomethyl, 2-chloropyridin-5-ylcarbonyl-aminomethyl, 2-[N,N (ethylcyano)(benzyl)-aminocarbonyl]-ethyl, 4-(methylthio)-phenylaminocarbonyl-aminomethyl, 2,4-difluorophenyl-carbonylamino-methyl, 2-propyl-2-[4-(phenylcarbonyl)-piperazin-1-ylcarbonyl]-ethyl, (4-hydroxyphenoxy)CH(CH$_3$)CONHCH$_2$—, 2-[4-(furan-2-ylcarbonyl)-piperidin-1-ylcarbonyl]-ethyl, N-(3,5-(dimethoxy)phenylcarbonyl-aminomethyl, methylsulfonyl-aminomethyl, phenylsulfonyl-aminomethyl, acetylaminomethyl, methoxy-carbonyl-aminomethyl, 4-carboxyphenyl-carbonylamino-methyl, 4-methylbenzoate-carboxamido-methyl, (2-pyrrol-1-yl)-phenylcarbonyl, 4-(methoxy-carbonyl)-phenylcarbonyl-aminomethyl, (imidazol-4-yl)-methyl, N-(phenylcarbonyl)-aminomethyl, 2-chlorophenylmethoxy-carbonylamino-methyl, 3-nitrophenyl-methoxy-carbonylamino-methyl, 3,5-dichlorophenyl-methoxy-carbonylamino-methyl, 2-(pyrrol-1-yl)-benzamido-methyl, benzyloxy-carbonylamino-methyl, 4-methoxyaniline-carbonylamino-methyl, 4-nitrobenzyloxy-carbonylamino-methyl, 2-bromobenzyloxy-carbonylamino-methyl, N-[4-(methoxycarbonyl)-phenylcarbonyl]-aminomethyl, N-(benzyloxycarbonyl)-aminopropyl, N-[2-(pyrrol-1-yl)-phenylcarbonyl]-aminomethyl, 2-[(diphenyl) methyl-aminocarbonyl]-ethyl, N-[3-(cyano)phenyl-aminocarbonyl]-aminomethyl, N-(thien-2-ylcarbonyl)-aminomethyl, N-(phenylcarbonyl)-aminomethyl, $(C_6H_5)CHCH_3NHCO(C_2H_4)CONHCH_2$—, $(4\text{methoxyphenyl})COC_2H_4CONHCH_2$—, N-(4-chlorophenylsulfonyl-aminocarbonyl)-aminomethyl, N-(5-(acetyl)thien-2-ylcarbonyl)-aminomethyl, N-(pyridin-3-ylcarbonyl)-aminomethyl, 2-[2-(methyl)-butyl-aminocarbonyl]-ethyl, (3,4,5-trimethoxyphenyl) $C_2H_4CONHCH_2$—, N-(3-(methoxy)phenyl-aminocarbonyl)-aminomethyl, 2-][$(C_6H_5)$ CHCH$_3$NHCO]-ethyl, (phenoxy)CH(CH$_2$CH$_3$) CONHCH$_2$—, (3-nitrophenyl)-CH$_2$SO$_2$NHCH$_2$—, N-[1-(ethoxycarbonyl)-piperidin-4-yl-aminomethyl-carbonyl]-aminomethyl, N-(4-(ethoxy)phenyl-aminocarbonyl)-aminomethyl, or N-(2-chloropyridin-5-ylcarbonyl)-aminomethyl;

R is —CH(R$^2$)Ar$^1$ or —CH(R$^2$)CH=CHAr$^1$ where R$^2$ is hydrogen or alkyl; and Ar$^1$ is optionally substituted aryl;

$Ar^2$ is 2,3,6-trimethoxy-4-methoxyphenyl; and their pharmaceutically acceptable salts, prodrugs, individual isomers, and mixtures of isomers.

4. The compound of claim 1 wherein $R^1$ is alkyl or aralkyl.

5. The compound of claim 4 wherein $R^1$ is 2-propyl or benzyl.

6. The compound of claim 1 wherein R is —$CN(R^2)Ar^1$ and wherein $R^2$ is alkyl.

7. The compound of claim 1 wherein R is —$CH(R^2)$CH=CHAr$^1$ and wherein $R^2$ is hydrogen.

8. A pharmaceutical composition comprising a therapeutically effective amount of a compound of claim 1 and a pharmaceutically acceptable excipient.

9. A pharmaceutical composition comprising a therapeutically effective amount of a compound of claim 2 and a pharmaceutically acceptable excipient.

10. A method of treatment of a disease selected from interstitial pulmonary fibrosis, idiopathic pulmonary fibrosis, acute respiratory distress syndrome and arthritis, said method comprising administering to a subject in need thereof a therapeutically effective amount of a compound of claim 1.

11. A process for preparing a compound of Formula (I) selected from compounds of claim 1, which process comprises:

(i) reacting a compound of formula 1:

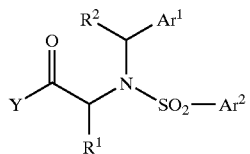

Y is hydroxy, halo, alkyl or succinimido ester with a hydroxylamine of formula NHR'OR" where R' is hydrogen or a nitrogen protecting group and R" is an O-protecting group, followed by *removal of the protecting group(s) to provide a compound of Formula (1); or (ii) reacting a compound of formula 2 where $R^a$ and $R^b$ are suitable O- and N-protecting groups:

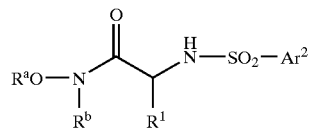

with an alkylating agent of formula $Ar^1CHR^2X$ or $Ar^1CH=CHCHR^2X$ where $Ar^1$, $R^2$ is as defined in claim 1 and X is a leaving group under alkylating reaction conditions, or an alcohol of formula $Ar^1CHR^2OH$ in the presence of a coupling agent and trialkylphosphine followed by removal of the protecting groups to provide a compound of Formula (I); and (iii) optionally converting the compound of Formula (I) prepared in Step (i)–(ii) above, to the corresponding acid addition salt by treatment with an acid;

(iv) optionally converting the compound of Formula (I) prepared in Steps (i)–(ii) above, to the corresponding free base by treatment with a base; and (v) optionally separating a mixture of stereoisomers of a compound of Formula (I) prepared in Steps (I)–(iv) above, to give a single stereoisomer.

* * * * *